(12) United States Patent
McGee et al.

(10) Patent No.: US 10,851,103 B2
(45) Date of Patent: *Dec. 1, 2020

(54) VALBENAZINE SALTS AND POLYMORPHS THEREOF

(71) Applicant: Neurocrine Biosciences, Inc., San Diego, CA (US)

(72) Inventors: Kevin McGee, San Diego, CA (US); Scott E. Zook, San Diego, CA (US); Andrew Carr, Cambridge (GB); Thierry Bonnaud, Cambridge (GB); Bin-Feng Li, Suzhou Industrial Park (CN)

(73) Assignee: Neurocrine Biosciences, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/899,645

(22) Filed: Jun. 12, 2020

(65) Prior Publication Data

US 2020/0339575 A1 Oct. 29, 2020

Related U.S. Application Data

(63) Continuation of application No. 16/662,346, filed on Oct. 24, 2019, now abandoned, which is a continuation of application No. 16/293,728, filed on Mar. 6, 2019, now abandoned, which is a continuation of application No. 16/043,059, filed on Jul. 23, 2018, now abandoned, which is a continuation of application No. 15/338,214, filed on Oct. 28, 2016, now Pat. No. 10,065,952.

(60) Provisional application No. 62/249,074, filed on Oct. 30, 2015.

(51) Int. Cl.
C07D 471/04 (2006.01)
A61K 31/4375 (2006.01)

(52) U.S. Cl.
CPC ........ C07D 471/04 (2013.01); *C07B 2200/13* (2013.01)

(58) Field of Classification Search
CPC .................... C07D 471/04; C07B 2200/13
See application file for complete search history.

(56) References Cited

U.S. PATENT DOCUMENTS

| | | |
|---|---|---|
| 3,536,809 A | 10/1970 | Norman |
| 3,598,123 A | 8/1971 | Zaffaroni |
| 3,845,770 A | 11/1974 | Takeru et al. |
| 3,916,899 A | 11/1975 | Takeru et al. |
| 4,008,719 A | 2/1977 | Theeuwes et al. |
| 4,328,245 A | 5/1982 | Yu et al. |
| 4,409,239 A | 10/1983 | Yu et al. |
| 4,410,545 A | 10/1983 | Yu et al. |
| 5,059,595 A | 10/1991 | Le Grazie |
| 5,073,543 A | 12/1991 | Marshall et al. |
| 5,120,548 A | 6/1992 | McClelland et al. |
| 5,354,556 A | 10/1994 | Sparks et al. |
| 5,591,767 A | 1/1997 | Mohr et al. |
| 5,612,059 A | 3/1997 | Cardinal et al. |
| 5,639,476 A | 6/1997 | Oshlack et al. |
| 5,639,480 A | 6/1997 | Bodmer et al. |
| 5,674,533 A | 10/1997 | Santus et al. |
| 5,698,220 A | 12/1997 | Cardinal et al. |
| 5,709,874 A | 1/1998 | Hanson et al. |
| 5,733,566 A | 3/1998 | Lewis |
| 5,739,108 A | 4/1998 | Mitchell |
| 5,759,542 A | 6/1998 | Gurewich |
| 5,798,119 A | 8/1998 | Herbig et al. |
| 5,840,674 A | 11/1998 | Yatvin et al. |
| 5,891,474 A | 4/1999 | Busetti et al. |
| 5,900,252 A | 5/1999 | Calanchi et al. |
| 5,922,356 A | 7/1999 | Koseki et al. |
| 5,972,366 A | 10/1999 | Haynes et al. |
| 5,972,891 A | 10/1999 | Karnei et al. |
| 5,980,945 A | 11/1999 | Ruiz |
| 5,985,307 A | 11/1999 | Hanson et al. |
| 5,993,855 A | 11/1999 | Yoshimoto et al. |
| 6,004,534 A | 12/1999 | Langer et al. |
| 6,039,975 A | 3/2000 | Shah et al. |
| 6,045,830 A | 4/2000 | Igari et al. |
| 6,048,736 A | 4/2000 | Kosak |
| 6,060,082 A | 5/2000 | Chen et al. |
| 6,071,495 A | 6/2000 | Unger et al. |
| 6,087,324 A | 7/2000 | Igari et al. |
| 6,113,943 A | 9/2000 | Okada et al. |
| 6,120,751 A | 9/2000 | Unger et al. |
| 6,131,570 A | 10/2000 | Schuster et al. |
| 6,139,865 A | 10/2000 | Friend et al. |
| 6,197,350 B1 | 3/2001 | Yamagata et al. |
| 6,248,363 B1 | 6/2001 | Patel et al. |
| 6,253,872 B1 | 7/2001 | Neumann |
| 6,264,970 B1 | 7/2001 | Hata et al. |
| 6,267,981 B1 | 7/2001 | Okamoto et al. |
| 6,271,359 B1 | 8/2001 | Norris et al. |
| 6,274,552 B1 | 8/2001 | Tamarkin et al. |
| 6,316,652 B1 | 11/2001 | Stelliou |

(Continued)

FOREIGN PATENT DOCUMENTS

| | | |
|---|---|---|
| EP | 1716145 | 11/2006 |
| JP | 57-077697 | 5/1982 |

(Continued)

OTHER PUBLICATIONS

Bastin et al., "Salt Selection and Optimisation Procedures for Pharmaceutical New Chemical Entities," Organic Process Res. Dev., 2000, 4(5):427-435.

(Continued)

*Primary Examiner* — John M Mauro
(74) *Attorney, Agent, or Firm* — Fish & Richardson P.C.

(57) ABSTRACT

Provided herein are salts of (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester in amorphous and crystalline forms, and processes of preparation, and pharmaceutical compositions thereof. Also provided are methods of their use for treating, preventing, or ameliorating one or more symptoms of neurological disorders and diseases including hyperkinetic movement disorders or diseases.

27 Claims, 18 Drawing Sheets

(56) References Cited

U.S. PATENT DOCUMENTS

| | | | |
|---|---|---|---|
| 6,350,458 B1 | 2/2002 | Modi et al. | |
| 6,376,461 B1 | 4/2002 | Igari et al. | |
| 6,419,961 B1 | 7/2002 | Igari et al. | |
| 6,589,548 B1 | 7/2003 | Oh et al. | |
| 6,613,358 B2 | 9/2003 | Randolph et al. | |
| 6,699,500 B2 | 3/2004 | Okada et al. | |
| 8,039,627 B2 | 10/2011 | Gano | |
| 8,357,697 B2 | 1/2013 | Gano | |
| 8,524,733 B2 | 9/2013 | Gant et al. | |
| 9,714,246 B2 | 7/2017 | Ashweek et al. | |
| 9,782,398 B2 | 10/2017 | Hoare | |
| 10,065,952 B2 | 9/2018 | McGee et al. | |
| 10,160,757 B2 | 12/2018 | McGee et al. | |
| 10,689,380 B1 * | 6/2020 | Lopez | C07D 471/04 |
| 2006/0051345 A1 | 3/2006 | Frohna | |
| 2006/0241082 A1 | 10/2006 | Fleckenstein et al. | |
| 2008/0108645 A1 | 5/2008 | Tridgett et al. | |
| 2008/0167337 A1 | 7/2008 | Gano | |
| 2009/0209755 A1 | 8/2009 | Suzuki et al. | |
| 2010/0076087 A1 | 3/2010 | Gant et al. | |
| 2011/0053866 A1 | 3/2011 | Duffield et al. | |
| 2012/0003330 A1 | 1/2012 | Gant et al. | |
| 2012/0077839 A1 | 3/2012 | Gano et al. | |
| 2014/0187505 A1 | 7/2014 | Pollard | |
| 2014/0341994 A1 | 11/2014 | Sommer et al. | |
| 2015/0004231 A1 | 1/2015 | Sommer et al. | |
| 2015/0025086 A1 | 1/2015 | Dressman et al. | |
| 2016/0030414 A1 | 2/2016 | Gant et al. | |
| 2016/0339011 A1 | 11/2016 | Hoare et al. | |
| 2016/0346200 A1 | 12/2016 | Sommer et al. | |
| 2016/0346270 A1 | 12/2016 | Stamler | |
| 2017/0071932 A1 | 3/2017 | O'Brien | |
| 2017/0145008 A1 | 5/2017 | McGee et al. | |
| 2017/0183346 A1 | 6/2017 | McGee et al. | |
| 2018/0085364 A1 | 3/2018 | Hoare | |
| 2019/0381016 A1 | 12/2019 | O'Brien et al. | |
| 2019/0381029 A1 | 12/2019 | Hoare et al. | |
| 2020/0078352 A1 | 3/2020 | O'Brien et al. | |
| 2020/0093808 A1 | 3/2020 | O'Brien et al. | |
| 2020/0101063 A1 | 4/2020 | O'Brien et al. | |
| 2020/0179352 A1 | 6/2020 | O'Brien | |
| 2020/0181140 A1 | 6/2020 | McGee et al. | |
| 2020/0206215 A1 | 7/2020 | Hoare et al. | |
| 2020/0230127 A1 | 7/2020 | O'Brien et al. | |
| 2020/0268724 A1 | 8/2020 | O'Brien et al. | |
| 2020/0268725 A1 | 8/2020 | O'Brien et al. | |
| 2020/0268743 A1 | 8/2020 | O'Brien et al. | |
| 2020/0268744 A1 | 8/2020 | O'Brien et al. | |
| 2020/0268745 A1 | 8/2020 | O'Brien et al. | |
| 2020/0276184 A1 | 9/2020 | Moore, Jr. et al. | |

FOREIGN PATENT DOCUMENTS

| | | | |
|---|---|---|---|
| JP | 57-209225 | 12/1982 | |
| WO | WO 1991/019498 | 12/1991 | |
| WO | WO 1998/011897 | 3/1998 | |
| WO | WO 2000/024399 | 5/2000 | |
| WO | WO 2002/017918 | 3/2002 | |
| WO | WO 2005/077946 | 8/2005 | |
| WO | WO 2007/017654 | 2/2007 | |
| WO | WO 2008/058261 | 5/2008 | |
| WO | WO-2008058261 A1 * | 5/2008 | C07D 471/04 |
| WO | WO 2009/056885 | 5/2009 | |
| WO | WO 2010/018408 | 2/2010 | |
| WO | WO 2010/026435 | 3/2010 | |
| WO | WO 2010/026436 | 3/2010 | |
| WO | WO 2010/044961 | 4/2010 | |
| WO | WO 2010/044981 | 4/2010 | |
| WO | WO 2011/019956 | 2/2011 | |
| WO | WO 2011/153157 | 12/2011 | |
| WO | WO 2014/047167 | 3/2014 | |
| WO | WO 2014/120654 | 8/2014 | |
| WO | WO 2015/077521 | 5/2015 | |
| WO | WO 2015/112707 | 7/2015 | |
| WO | WO 2015/120110 | 8/2015 | |
| WO | WO 2015/120317 | 8/2015 | |
| WO | WO 2015/171802 | 11/2015 | |
| WO | WO 2016/127133 | 8/2016 | |
| WO | WO 2016/144901 | 9/2016 | |
| WO | WO 2016/210180 | 12/2016 | |
| WO | WO 2017/112857 | 6/2017 | |
| WO | WO 2018/102673 | 6/2018 | |
| WO | WO 2018/140092 | 8/2018 | |
| WO | WO 2018/140093 | 8/2018 | |
| WO | WO 2018/140094 | 8/2018 | |
| WO | WO 2018/140095 | 8/2018 | |
| WO | WO 2018/140096 | 8/2018 | |
| WO | WO 2018/200605 | 11/2018 | |
| WO | WO 2019/060322 | 3/2019 | |
| WO | WO 2019/074492 | 4/2019 | |
| WO | WO 2019/241555 | 12/2019 | |
| WO | WO 2020/037022 | 2/2020 | |

OTHER PUBLICATIONS

U.S. Appl. No. 16/899,641, filed Jun. 12, 2020, McGee et al.
U.S. Appl. No. 16/899,654, filed Jun. 12, 2020, McGee et al.
Bauer, "Pharmaceutical Solids—The Amorphous Phase," J Validation Tech., 2009, 15(3):63-68.
Caira et al., "Crystalline Polymorphism of Organic Compounds," Topics in Current Chemistry, 1998, 198(36):163-208.
Erickson et al., "Reserpine-and tetrabenazine-sensitive transport of (3)H-histamine by the neural isoform of the vesicular monoamine transporter," Journal of Molecular Neuroscience, 1995, 6(4):277-287.
Foster et al., "Deuterian isotope effects in studies of drug metabolism," Adv. Drug Res., 1985, 14:1-36.
Gately et al., "Deuterioglucose: alteration of biodistribution by an isotope effect," J. Nucl. Med., 1986, 27:388-394.
Gordon et al., "The Metabolism of the abortifacient terpene, (R)-(+)-pulegone, to a proximate toxin menthofuran," Drug Metab Dispos., 1987, 15:589-594.
Jacq et al., "Development and validation of an automated static headspace gas chromatography—mass spectrometry (SHS-GC-MS) method for monitoring the formation of ethyl methane sulfonate from ethanol and methane sulfonic acid," J Pharm. Biomed Anal., 2008, 48(5):1339-1344.
Jankovic, J., "Dopamine depleters in the treatment of hyperkinetic movement disorders," Expert Opinion on Pharmacotherapy, 17.18, 2016, 2461-2470.
Kenney et al., "Long-Term Tolerability of Tetrabenazine in the Treatment of Hyperkinetic Movement Disorders," Movement Disorders, 2007, 22(2):193-197.
Kenney et al., "Tetrabenazine in the treatment of hyperkinetic movement disorders," Expert Review Neurotherapeutics, 2006, 6(1):7-17.
Kilbourn et al., "In vivo binding of (+)-α-[3H]dihydrotetrabenazine to the vesicular monoamine transporter of rat brain: bolus vs. equilibrium studies," European Journal of Pharmacology, 1997, 331(2-3):161-168.
Kilbourn et al., "Absolute configuration of (+)-alpha-dihydrotetrabenazine, an active metabolite of tetrabenazine," Chirality, 1997, 9:59-62.
Kilbourn et al., "Binding of alpha-dihydrotetrabenazine to the vesicular monoamine transporter is stereospecific," European Journal of Pharmacology, 1995, 278(3):249-252.
Kilbourn et al., "In vivo measures of dopaminergic radioligands in the rat brain: equilibrium infusion studies," Synapse, 2002, 43(3):188-194.
Kushner et al., "Pharmacological uses and perspectives of heavy water and deuterated compounds," Can. J. Physiol. Pharmacol., 1999, 77(2):79-88.
Lee et al., "In vitro and in vivo studies of benzisoquinoline ligands for the brain synaptic vesicle monoamine transporter," J. Med. Chem., 1996, 39(1):191-196.
Lijinsky el. al., "Dose-response studies with nitrosoheptamethyleneimine and its alpha-deuterium-labeled derivative in F344 rats," Nat. Cancer Inst., 1982, 69(5):1127-1133.

(56) References Cited

OTHER PUBLICATIONS

Lijinsky et al., "Dose-Response Studies in Carcinogenesis by Nilroso-N-Methyl-N-(2-Phenyl)elhylamine in Rats and he Effects of Deuterium Substitution," Food Cosmet. Toxicol., 1982, 20:393-399.
Mangold el. al., "Effects of deuterium labeling on azido amino acid mutagenicity in *Salmonella typhimurium*," Mutation Res., 1994, 308(1):33-42.
Muller, "Valbenazine granted breakthrough drug status for treating tardive dyskinesia," Expert Opin. Investig. Drugs, 2015, 24:(6)737-742.
O'Brien et al., "NBI-98854, a selective monoamine transport inhibitor for the treatment of tardive dyskinesia: a randomized, double-blind, placebo-controlled study," Movement Disorders, 2015, 30(12):1681-1687.
Santus and Baker, "Osmotic drug delivery: a review of the patent literature," J. Controlled Release, 1995, 35:1-21.
Sawant, "Necessity of Establishing Chemical Integrity of Polymorphs of Drug Substance Using a Combination of NMR, HPLC, Elemental Analysis, and Solid-State Characterization Techniques: Case Studies," Organic Process Research & Development 17.3, 2013, :519-532.
Scherman et al., "[3H]dihydrotetrabenazine, a new in vitro monoaminergic probe for human brain," Journal of Neurochemistry, 1988, 50(4):1131-1136.
Teasdale et al., "Mechanism and Processing Parameters Affecting the Formation of Methyl Methanesulfonate from Methanol and Methanesulfonic Acid: An Illustrative Example for Sulfonate Ester Impurity Formation," Org Process Res. Dev., 2009, 15:13429-433.
Teasdale, "Sulfonate Esters—How Real is the Risk? Summary of Key Findings from PQRI Studies of the Reaction Between Sulfonic acids and Alcohols," 42 pages.
Teasdale, "Sulphonate esters: a real or imagined risk? PQRI studies to determine actual risk," British Pharmaceutical Conference, Manchester Sep. 10-12, 2007, J Pharmacy Pharmacol. A-78, Abstract 218.
Verma et al., "Formulation aspects in the development of osmotically controlled oral drug delivery systems," J. Controlled Release, 2002, 79(1-3):7-27.
Verma et al., "Osmotically controlled oral drug delivery," Drug Development and Industrial Pharmacy, 2000, 26(7):695-708.
Wade, D., "Deuterium isotope effects on noncovalent interactions between molecules," Chem. Biol. Interact., 1999, 117(3):191-217.
Zello et. al., "Plasma and urine enrichments following infusion of L[1-13C]phenylalanine and L-[ring-2H5] phenylalanine in humans evidence for an isotope effect in renal tubular reabsorption," Metabolism, 1994, 43(4):487-491.
U.S. Appl. No. 16/481,033, filed Jul. 25, 2019, O'Brien et al.
U.S. Appl. No. 16/481,034, filed Jul. 25, 2019, O'Brien et al.
U.S. Appl. No. 16/481,037, filed Jul. 25, 2019, O'Brien et al.
U.S. Appl. No. 16/509,552, filed Jul. 12, 2019, McGee et al.
U.S. Appl. No. 16/608,521, filed Oct. 25, 2019, O'Brien.
U.S. Appl. No. 16/646,866, filed Mar. 12, 2020, Moore Jr. et al.
U.S. Appl. No. 16/651,887, filed Mar. 27, 2020, O'Brien et al.
U.S. Appl. No. 16/662,346, filed Oct. 24, 2019, McGee et al.
U.S. Appl. No. 16/701,339, filed Dec. 3, 2019, O'Brien et al.
U.S. Appl. No. 16/754,658, filed Apr. 8, 2020, O'Brien et al.
U.S. Appl. No. 16/817,723, filed Mar. 13, 2020, Hoare et al.
U.S. Appl. No. 16/845,134, filed Apr. 10, 2020, O'Brien et al.
U.S. Appl. No. 16/870,423, filed May 8, 2020, O'Brien et al.
U.S. Appl. No. 16/870,572, filed May 8, 2020, O'Brien et al.
U.S. Appl. No. 16/870,706, filed May 8, 2020, O'Brien et al.
U.S. Appl. No. 16/870,823, filed May 8, 2020, O'Brien et al.
U.S. Appl. No. 16/871,528, filed May 11, 2020, O'Brien et al.
U.S. Appl. No. 16/929,694, filed Jul. 15, 2020, McGee et al.
U.S. Appl. No. 16/929,696, filed Jul. 15, 2020, McGee et al.
U.S. Appl. No. 16/929,714, filed Jul. 15, 2020, McGee et al.
U.S. Appl. No. 16/929,716, filed Jul. 15, 2020, McGee et al.
U.S. Appl. No. 16/983,334, filed Aug. 3, 2020, Liang et al.
U.S. Appl. No. 16/989,206, filed Aug. 10, 2020, Loewen et al.

"Cytochrome P450 Oxidoreductase (POR) Deficiency," GeneDx, 2016, 5 pages.
"Neurocrine Valbenazine," Science IP Order 3198386, Oct. 2, 2019, 92 pages.
[No Author Listed], "Cytochrome P450 3A4 and 3A5 known drug interaction chart," 2014, 2 pages.
[No Author Listed], "Drug interactions with CYP3A inducers and inhibitors for Torisel (temsirolimus) injection," Wyeth Pharmaceuticals, 2008, 12 pages.
[No Author Listed], "Physician guidelines: drugs metabolized by cytochrome P450's," Genelex Corporation, 2005, 4 pages.
[No Author Listed],"Ingrezza Prescription Information," Neurocrine Biosciences, Apr. 2017, 16 pages.
Alexander et al., "Increased aggression in males in transgenic Tg2576 mouse model of Alzheimer's disease," Behav Brain Res., 216(1):77-83.
Anonymous, "11th Annual Meeting Schedule," ASENT, Mar. 5-7, 2009, 3 pages.
Anonymous, "12th Annual Meeting Program," ASENT, Bethesda, Maryland, Mar. 4-6, 2010, 1 page.
Anonymous, "Neurocrine Announces Phase IIb Results of VMAT2 Inhibitor NBI-98854 for Treatment of Tardive Dyskinesia," Neurocrine Biosciences: Investors: PressRelease, Sep. 9, 2013, [retrieved on Dec. 13, 2018] retrieved from URL<http://phoenix.corporate-ir.net/phoenix.zhtml?c=68817&p=irol-newsArticle_Print&ID=1853185>, 7 pages.
Australian Office Action in AU Appln. No. 2015256012, dated May 26, 2020, 5 pages.
Ballard et al., "Management of Agitation and Aggression Associated with Alzheimer's disease: controversies and possible solutions," Curr Opin in Psych., Nov. 2009, 22(6):532-540.
Ballard et al., "Neuroleptic drugs in dementia: benefits and harm," Nat Rev Neurosci., Jun. 2006, 7:492-500.
Ballard et al., "Quetiapine and rivastigmine and cognitive decline in Alzheimer's disease: randomised double blind placebo controlled trial," BMJ, Apr. 16, 2005, 330:874-877.
Berge et al., "Pharmaceutical Salts," J Pharm Sci., Jan. 1977, 66(1):1-19.
Bhidayasiri and Boonyawairoj, "Spectrum of tardive syndromes: clinical recognition and management.," Postgrad Med J, Feb. 2011, 87(1024): 132-141.
Boldt et al., "Synthesis of (+)- and (-)-Tetrabenazine from the Resolution of [alpha]-Dihydrotetrabenazine," Synthetic Communications, 2009, 39(20):3574-3585.
Brunner et al., "Comprehensive Analysis of the 16p11.2 Deletion and Null Cntnap2 Mouse Models of Autism Spectrum Disorder," PLoS One, Aug. 14, 2015, 10(8):e0134572.
Brusa et al., "Tetrabenazine improves levodopa-induced peak-dose dyskinesias in patients with Parkinson's disease," Funct. Neural., 2013, 28(2):101-5.
Bystritsky, "Treatment-resistant anxiety disorders," Mol. Psychiatry, Sep. 2006, 11(9):805-814.
Caroff et al., "Treatment of tardive dyskinesia with tetrabenazine or valbenazine: a systematic review," J. Com. Eff. Research, 2017, 7(2):135-148.
Chinese Office Action in Chinese Application No. 201580023821.X, dated Jun. 20, 2018, 10 pages.
Citrome, "Valbenazine for tardive dyskinesia: A systematic review of the efficacy and safety profile for this newly approved novel medication—What is the number needed to treat, number needed to harm and likelihood to be helped or harmed?," Int J Clin Pract., 2017, e12964.
Cohen-Mansfield et al., "A description of agitation in a nursing home," J Gerontol., May 1989, 44(3):M77-M84.
Correll and Schenk, "Tardive dyskinesia and new antipsychotics," Curr Opin Psychiatry, Mar. 2008, 21(2):151-156.
Corvin, "Two patients walk into a clinic . . . a genomics perspective on the future of schizophreniam," BMC Biol., 2011, 8 pages.
Cummings et al., "The Neuropsychiatric Inventory: comprehensive assessment of psychopathology in dementia," Neurology, 1994, 44:2308-2314.

(56) References Cited

OTHER PUBLICATIONS

Derangula et al, "Liquid chromatography-tandem mass spectrometric assay for the determination of tetrabenazine and its active metabolites in human plasma: a pharmacokinetic study," Biomedical Chromatography, Jun. 2013, 27(6):792-801.
Drug Development and Drug Interactions: Table of Substrates, Inhibitor and Inducers at https://www.fda.gov/drugs/developmentapprovalprocess/developmentesources/druginteractionslabeling/ucm093664.htm, U.S. Food and Drug Administration, 2017, 18 pages.
Eurasian Office Action in Eurasian Application No. 201890108, dated Oct. 30, 2018, 5 pages.
European Office Action in European Application No. 15734438.5, dated Jul. 17, 2018, 4 pages.
Fahr, "Kapseln," Pharmazeutische Technologie, Jan. 2000, p. 237.
Fields et al., "Pill Properties that Cause Dysphagia and Treatment Failure," Current Therapeutic Research, Aug. 2015, 77:79-82.
Gantois et al., "Restoring the phenotype of fragile X syndrome: insight from the mouse model," Curr Mol Med., Sep. 2001, 1(4):447-455.
Gottlieb et al., "NMR Chemical Shifts of Common Laboratory Solvents as Trace Impurities," J. Org. Chem. 1997, 62 (21): 7512-7515.
Grigoriadis et al., "Pharmacologic characterization of valbenazine (NBI-98854) and its metabolites," Journal of Pharmacology and Experimental Therapeutics, 2017, 361(3):454-461.
Guilloteau et al., "PET and SPECT exploration of central monoaminergic transporters for the development of new drugs and treatments in brain disorders," Current Pharmaceutical Design, Jan. 1, 2005, 11(25):3237-3245.
Gulieva et al., "Neuropharmacology analysis of the effect of olanzapine and clozapine on behavior characteristics and neuromodulator content in rat brain structure," Psychopharmacology and biological necrology, 2004, 585-589.
Guridi et al., "Clinical Features, Pathophysiology, and Treatment of Levodopa-Induced Dyskinesias in Parkinson's Disease," Parkinson's Disease, 2012, 1-15.
Harriot et al., "Identification of the First Selective Small Molecule BB2 Antagonists," Poster, Presented at the 249th ACS National Meeting & Exposition, Denver CO, Mar. 22-26, 2015, 1 page.
Hauser et al., "KINECT 3: A phase 3 randomized, double-blind, placebo-controlled trial of valbenazine for tardive dyskinesia," American Journal of Psychiatry, 2016, 174(5):476-484.
Healy et al., "Clozapine-reserpine combination for refractory psychosis," Schizophrenia Research, Jan. 1, 1997, 25:259-260.
Herrmann et al., "A Placebo-Controlled Trial of Valproate for Agitation and Aggression in Alzheimer's Disease," Dement Geriatr Cogn Disord., Jan. 2007, 23:116-119.
Hoare et al., "Conformational states of the corticotropin releasing factor 1 (CRF1) receptor: detection, and pharmacological evaluation by peptide ligands," Peptides, Dec. 2003, 24(12):1881-1897.
Horev et al., "Dosage-dependent phenotypes in models of 16p11.2 lesions found in autism," Proc Natl Acad Sci USA., 2011, 108(41):17076-17081.
Howard et al., "Guidelines for the management of agitation in dementia," Int. J. Geriatr. Psychiatry, Jul. 2001, 16(7):714-717.
Hu, "New Fluorescent Substrate Enables Quantitative and High-throughput Examination of Vesicular Monoamine Transporter 2 (VMAT2)," ACS Chem Biol. 2013, Sep. 20:8(9):19471954.
Ingrezza, Highlights of Prescribing Information, Neurocrine Biosciences, Inc., revised Oct. 2017, 15 pages.
Ingrezza, Patient Information, Neurocrine Biosciences, Inc., revised Oct. 2017, 1 page.
International Preliminary Report on Patentability in Appln. No. PCT/US2017/055907, dated Apr. 14, 2020, 18 pages.
International Preliminary Report on Patentability in Appln. No. PCT/US2017/055947, dated Apr. 23, 2020, 10 pages.
International Preliminary Report on Patentability in Appln. No. PCT/US2018/029255, dated Oct. 29, 2019, 7 pages.
International Preliminary Report on Patentability in International Application No. PCT/US2016/039098, dated Dec. 26, 2017, 8 pages.
International Preliminary Report on Patentability in International Application No. PCT/US2017/055877, dated Jul. 30, 2019, 11 pages.
International Preliminary Report on Patentability in International Application No. PCT/US2017/055931, dated Jul. 30, 2019, 16 pages.
International Preliminary Report on Patentability in International Application No. PCT/US2017/055965, dated Jul. 30, 2019, 8 pages.
International Preliminary Report on Patentability in International Application No. PCT/US2017/055980, dated Jul. 30, 2019, 7 pages.
International Preliminary Report on Patentability in International Appln. No. PCT/US2017/064196, dated Jun. 4, 2019, 6 pages.
International Report on Patentability in International Application No. PCT/US2015/029519, dated Nov. 8, 2016, 8 pages.
International Search Report and Written Opinion in Appln. No. PCT/US2017/055877, dated Dec. 26, 2019, 11 pages.
International Search Report and Written Opinion in Appln. No. PCT/US2017/055907, dated Dec. 5, 2017, 21 pages.
International Search Report and Written Opinion in Appln. No. PCT/US2017/055931, dated Dec. 11, 2017, 17 pages.
International Search Report and Written Opinion in Appln. No. PCT/US2017/55965, dated Dec. 5, 2017, 9 pages.
International Search Report and Written Opinion in Appln. No. PCT/US2018/029255, dated Jun. 26, 2018, 9 pages.
International Search Report and Written Opinion in Appln. No. PCT/US2017/55980, dated Dec. 1, 2017, 9 pages.
International Search Report and Written Opinion in International Application No. PCT/US2015/029519, dated Jun. 21, 2015, 11 pages.
International Search Report and Written Opinion in International Application No. PCT/US2016/039098, dated Nov. 22, 2016, 15 pages.
International Search Report and Written Opinion in International Appln. No. PCT/US2017/064196, dated Feb. 21, 2018, 10 pages.
International Search Report and Written Opinion in International Appln. No. PCT/US2019/46462, dated Nov. 7, 2019, 14 pages.
International Search Report in Appln. No. PCT/US2017/055947, dated Dec. 5, 2017, 8 pages.
Jankovic and Beach, "Long-term effects of tetrabenazine in hyperkinetic movement disorders," Neurology, Feb. 1, 1997, 48(2):359-362.
Jankovic et al., "Lesch-Nyhan Syndrome. A Study of Motor Behaviour and Cerebrospinal Fluid Neurotransmitters," Ann Neuro., May 1988, 23(5):466-469.
Japanese Office Action in Japanese Application No. 2016-566238, dated Feb. 12, 2019, 13 pages.
Jiang, "Application of Deuteration in Drug Research,"Qilu Pharmacautical Affairs, 29(11):682-684.
Jinnah et al., "Amphetamine-induced behavioral phenotype in a hypoxanthine-guanine phosphoribosyltransferase-deficient mouse model of Lesch-Nyhan syndrome," Behav Neurosci., Dec. 1991, 105(4):1004-1012.
Josiassen et al., "Long-term safety and tolerability of valbenazine (NBI-98854) in subjects with tardive dyskinesia and a diagnosis of Schizophrenia or mood disorder," Psychopharmacology Bulletin, 2017, 47(3):61-68.
Jul et al., "Hyperactivity with Agitative-Like Behavior in a Mouse Tauopathy Model," J Alzheimer's Dis., 2015, 49(3):783-795.
Katz et al., "Preclinical research in Rett syndrome: setting the foundation for translational success," Disease Models & Mechanisms, 2012, 5:733-745.
Kay et al., "The Positive and Negative Syndrome Scale (PANSS) for Schizophrenia," Schizophrenia Bulletin, 1987, 13:262-276.
Kazdoba et al., "Modeling fragile X syndrome in the Fmr1 knockout mouse," Intractable Rare Dis Res., Nov. 2014, 3(4):118-133.
Khalsa et al., "Treatment-resistant OCD: Options beyond first-line medications," Curr. Psychiatry, 2011, 10(11):45-52.
Kim, "Valbenazine: First Global Approval," Drugs, 2017, 77:1123-1129.

(56) References Cited

OTHER PUBLICATIONS

Kimiagar er al., "Rapid improvement of tardive dyskinesia with tetrabenazine, clonazepam and clozapine combined: a naturalistic long-term follow-up study," J Neurol., Nov. 9, 2011, 259(4):660-664.
Koch et al., "Successful Therapy of Tardive Dyskinesia in a 71-year-old Woman with a combination of Tetrabenazine, Olanzapine and Tiapride," IJCP, Mar. 1, 2003, 57(2):147-149.
Kuehn et al., "A potential animal model for Lesch-Nyhan syndrome through introduction of HPRT mutations into mice," Nature, Mar. 1987, 326(6110):295-298.
Kurlan, "Treatment of Tourette Syndrome," Neurotherapeutics, 2014, 11:161-165.
Loewen et al., "Evaluation of the potential for concomitant medications to affect valbenazine pharmacokinetics," Poster, Presented at the American Society of Clinical Psychopharmacology, May 29-Jun. 2, 2017: Miami, FL, 1 page.
Loewen et al., "Evaluation of the potential for valbenzaine to elicit drug interactions," Poster, Presented at the American Society of Clinical Psychopharmacology, May 29-Jun. 2, 2017: Miami, FL, 1 page.
Lombroso et al., "Tourette Syndrome and Obsessive-Compulsive Disorder ," Brain Dev., 2008, 30(4): 231-237.
Loriot et al., "Drug insight: gastrointestinal and hepatic adverse effects of molecular-targeted agents in cancer therapy," Nature Clinical Practice Oncology, 2008, 5(5):268-278.
Luo et al., "Single dose and repeat once-daily dose safety, tolerability, and pharmacokinetics of valbenazine in healthy male subjects," Poster, Presented at the American Psychiatric Association Annual Meeting, May 20-24, 2017, San Diego, CA, 1 page.
Madan, Invited Speaker, "NBI-98854: Human pharmacokinetics of NBI-98854 a selective inhibitory of VMAT2 with an attractive PK and safety profile for hyperkinetic movement disorders," Pipeline Projects Session, 12th annual meeting of American Society for Experimental NeuroTherapeutics, Bethesda, MD, 2010, 5 slides.
Madan, Invited Speaker, "NBI-98854: Selective inhibitor of VMAT2 with an attractive PK and safety profile for hyperkinetic movement disorders," Pipeline Projects Session, 11th annual meeting of American Society for Experimental NeuroTherapeutics, Arlington, VA, 2009, 9 slides.
Marder et al., "Kinect 3: a randomized, double-blind, placebo-controlled phase 3 trial of valbenazine (NBI-98854) for Tardive Dyskinesia," American Academy of Neurology, 2016, 9 pages.
Margolese et al., "Tardive dyskinesia in the era of typical and atypical antipsychotics. Part 1: pathophysiology and mechanisms of induction," Can J Psychiatry, Aug. 2005, 50(9):541-47.
Material Safety Data Sheet. Product Name Valbenazine tosylate. Published May 1, 2014 (see Revision date). Retrieved from internet May 23, 2020. URL: https://www.selleckchem.com/msds/MSDS_S9500.pclf.
McBride et al., "Using *Drosophila* as a tool to identify Pharmacological Therapies for Fragile X Syndrome," Drug Discov Today Technol., Sep. 24, 2012, 10(1):e129-e136.
Mehvar et al., "Pharmacokinetics of tetrabenazine and its major metabolite in man and rat. Bioavailability and dose dependency studies," Drug Metabolism and Distribution, 1987, 15(2):250-255.
mentalhealthamerica.net [online], "Depression," [retrieved on Dec. 17, 2018], retrieved from URL<http://www.mentalhealthamerica.net/conditions/depression>, 3 pages.
Mineur et al., "Social behavior deficits in the Fmr1 mutant mouse," Behav Breain Res., Mar. 15, 2006, 168(1):172-175.
Muller et al., "Valbenazine for the treatment of tardive dyskinesia," Expert Review of Neurotherapeutics, 2017, 17(2):1135-1144.
Near, "[3H]Dihydrotetrabenazine binding to bovine striatal synaptic vesicles," Mol. Pharmacol., Sep. 1986, 30:252-257.
Nikoloff et al., "Association between CYP2D6 genotype and tardive dyskinesia in Korean schizoprenics," The Pharmacogenomics J, 2002, 2:400-407.

ninds nih.gov [online], Available on or before Jan. 24, 2013, via Internet Archive: Wayback Machine URL <https://web.archive.org/web/20130124115120/www.ninds.nih.gov/disorders/rett/detail_rett.htm>, retrieved on Dec. 17, 2018], retrieved from URL<www.ninds.nih.gov/disorders/rett/detail_rett.htm>, 6 pages.
Nunes et al., "Effort-related motivational effects of the VMAT-2 inhibitor tetrabenazine: implications for animal models of the motivational symptoms of depression," J. Neurosci., 2013, 33(49):19120-30.
Nyhan et al., "Lesch-Nyhan Syndrome," Posted Sep. 25, 2000[last update May 15, 2014], 21 pages.
Ondo et al, "Tetrabenazine treatment for tardive dyskinesia: assessment by randomized videotape protocol," Am J Psychiatry, Aug. 1999, 156(8):1279-1281.
Owesson-White et al., "Sources contributing to the average extracellular concentration of dopamine in the nucleus accumbens," J Neurochem., 2012, 121:252-62.
Pallanti and Quercioli, "Treatment-refractory obsessive-compulsive disorder: methodological issues, operational definitions and therapeutic lines," Neuropsychopharmacol. Biol Psychiatry, May 2006, 30(3):400-412.
PCT International Preliminary Report on Patentability in International Appln. No. PCT/US2018/051579, dated Apr. 2, 2020, 25 pages.
PCT International Search Report and Written Opinion in International Appln. No. PCT/US2018/051579, dated Mar. 18, 2019, 36 pages.
Piccinni et al., "Effectiveness of a Clozapine-Aripiprazole Combination in Tourette Syndrome and Bipolar Spectrum Disorder," J Neuropsychiatry Clin Neurosci., Jan. 1, 2013, 25:1.
Pincus, "Management of digoxin toxicity," Aust. Prescr., 2016, 39(1):18-21.
Pittenger et al., "Pharmacological treatment of obsessive-compulsive disorder," Psychiatr. Clin. North Am., 2014, 37(3):375-391.
Poliak et al., "Juxtaparanodal clustering of Shaker-like K+ channels in myelinated axons depends on Caspr2 and TAG-1," J Cell Biol., Sep. 15, 2003, 162(6):1149-1160.
Porta et al., "Tourette's syndrome and role of tetrabenazine," Clin Drug Invest., 2008, 28(7):443-459.
Portman et al., "Behavioral abnormalities and circuit defects in the basal ganglia of a mouse model of 16p11.2 deletion syndrome," Cell Rep., May 22, 2014, 7(4):1077-1092.
Prescott, "Powder handling," Pharmaceutical Process Scale-Up, Jan. 2011, 195-209.
Provenzano et al., "Mutant mouse models of autism spectrum disorders," Dis. Markers, 2012, 33(5):225-239.
Rao et al, "Review article: metoclopramide and tardive dyskinesia," Aliment Pharmacol Ther 2010, 31(1):11-19.
Remington et al., "Tetrabenazine Augmentation in Treatment-Resistant Schizophrenia," Journal of Clinical Psychopharmacology, Feb. 1, 2012, 32(1):95-99.
Robey et al., "Modes and patterns of self-mutilation in persons with Lesch-Nyhan disease," Dev Med Child Neurol. Mar. 2003, 45(3):167-171.
Russian Office Action in Russian Application No. 2016147523, dated Dec. 27, 2018, 18 pages.
Sakimoto et al., "Phenotypic abnormalities in a chorea-acanthocytosis mouse model are modulated by strain background," Biochem Biophys Res Commun., 472(1):118-124.
Schneider et al., "Efficacy and adverse effects of atypical antipsychotics for dementia: meta-analysis of randomized, placebo-controlled trials," Am J Geritr Psychiatry., 2006, 14(3):191-210.
Schretlen et al., "Behavioral aspects of Lesch-Nyhan disease and its variants," Dev Med Child Neurol., Oct. 2005, 47(10):673-677.
Schretlen et al., "Neurocognitive functioning in Lesch-Nyhan disease and partial hypoxanthine-guanine phosphoribosyltransferase deficiency," J Int. Neuropsychol Soc., 2001, 7:805-812.
Scott et al., Making and Breaking Serotonin Neurons and Autism, Int J Devl Neuroscience., 2005, 23:277-285.
Sever et al., "Process Analytical Technology in Solid Dosage Development and Manufacturing," Developing Solid Oral Dosage Forms Pharmaceutical Theory and Practice, Jan. 2008, 827-841.

(56) References Cited

OTHER PUBLICATIONS

Shen et al. "Safety and Efficacy of Tetrabenazine and use of Cocomitant Medications during Long-Term, Open-Label Treatment of Chorea Associated with Huntington's and Other Diseases," Tremor and Other Myperkinetic Movements, Oct. 22, 2013, https://tremorjournal.org/index.php/tremodarticle/view/191, pp. 1-12.
Silverman et al., "Behavioural phenotyping assays for mouse models of autism," Nature Reviews Neuroscience, Jul. 2010, 11(7):490-502.
Simpson et al., "A rating scale for extrapyramidal side effects," Acta Psychiatry Scand Suppl, 1970, 212:11-19.
Skor et al., "Differences in dihydrotetrabenazine isomer concentrations following administration of tetrabenazine and valbenazine," Drugs R D, 2017, 17:449-459.
Smolders et al., "Pharmacokinetics, efficacy, and safety of Hepatitis C virus drugs in patients with liver and/or renal impairment," Drug safety, 2016, 39(7):589-611.
Solon, "Risperidone-reserpine combination in refractory psychosis," Schizophrenia Research, Dec. 1, 1996, 22(3):265-266.
Spencer et al., "Social behavior in Fmr1 knockout mice carrying a human FMR1 transgene," Behave. Neurosci., Jun. 2008, 122(3):710-715.
Spina et al., "Effect of fluoxetine on the plasma concentrations of clozapine and its major metabolites in patients with schizophrenia," International Clinical Psychopharmacology, May 1, 1998, 13(3):141-145.
STN CAS RN: 1639208-54-0, entered STN Dec. 22, 2014, 1 page.
Sun et al., "Preparation and evaluation of tetrabenazine enantiomers and all eight stereoisomers of dihydrotetrabenazine as VMAT2 inhibitors," Eur. J. Med. Chem., 2011, 46(5):1841-1848.
Table 14.3.5.14.1, "Young Mania Rating Scale (YMRS) Total Score and Change from Baseline (CFB) Values by Visit and Treatment Group," Neurocrine Biosciences, Inc., Oct. 8, 2015, 6 pages.
Tandon et al., "World Psychiatric Association Pharmacopsychiatry Section Statement on Comparative Effectiveness of Antipsychotics in the Treatment of Schizophrenia," Schizophrenia Research, Mar. 1, 2008, 100(1-3):20-38.
Tarsy and Baldessarini, "Epidemiology of tardive dyskinesia: is risk declining with modern antipsychotics?" Movement Disorders, May 2006, 21(5):589-598.
Tauber et al., "Elevated Levels of the Vesicular Monoamine Transporter and a Novel Repetitive Behavior in the *Drosophila* Model of Fragile X Syndrome," Plos One, Nov. 11, 6(11):e27100.
Tenback et al, "Incidence and persistence of tardive dyskinesia and extrapyramidal symptoms in schizophrenia," J Psychopharmacol, Jul. 2010, 24(7):1031-1035.
Teng et al., "Lobeline displaces [3H]dihydrotetrabenazine binding and releases [3H]dopamine from rat striatal synaptic vesicles: comparison with d-amphetamine," J Neurochem. 1998, 71(1):258-265.
Thai-Curato et al., "Cardiovascular profile of valbenazine: analysis of pooled dated from three randomized, double-blind, placebo-controlled trials," Drug Safety, 2017, 41(4):429-440.
Tian et al., "CYP3A4-mediated pharmacokinetic interactions in cancer therapy," Curr. Drug Metab., 2014, 15(8):808-17.
Tomemori et al., "A gene-targeted mouse model for chorea-acanthocytosis," J Neurochem, 2005, 92(4):759-766.
Traynor, "Valbenazine approved for treatment of tardive dyskinesia," ASHP, Apr. 17, 2017, retrieved from URL: https://www.ashp.org/news/2017/04/17/valbenazine-approved-for-treatment-of-tardive-dyskinesia?loginreturnUrl=SSOCheckOnly, retrieved on Jun. 22, 2020, 3 pages.
Tsoussis et al., "Disclosure of cancer diagnosis: the Greek experience," JBUON, Open Access Journal aimed at the rapid diffusion of scientific knowledge in Oncology, 2013, 18(2):516-526.
United States Pharmacopoeia ("USP"), "Bulk Density and Tapped Density of Powders," <616>, 2015, 3 pages.
United States Pharmacopoeia ("USP"), "Disintegration," <701>, 2016, 4 pages.
United States Pharmacopoeia ("USP"), "Dissolution," <711>, 2011, 8 pages.
United States Pharmacopoeia ("USP"), "Uniformity of Dosage Units," <905>, 2016, 9 pages.
United States Pharmacopoeia, "Light Diffraction Measurement of Particle Size," <429>, 2016, 8 pages.
US Department of Health and Human Services, and Food and Drug Administration, "Size, Shape, and Other Physical Attributes of Generic Tablets and Capsules," Jun. 2015, 10 pages.
Verkerk et all., "Identification of a gene (FMR-1) containing a CGG repeat coincident with a breakpoint cluster region exhibiting length variation in fragile X syndrome," Cell, May 1991, 65(5):905-914.
Watts et al., "Clinical and biochemical studioes on treatment of Lesch-Nylan Syndrome," Archives of Disease in Childhood., 1974, 49:693-702.
Weihe and Eiden, "Chemical neuroanatomy of the vesicular amine transporters.," The FASEB Journal, Dec. 2000, 14(15):2435-2449.
Woods et al, "Incidence of tardive dyskinesia with atypical versus conventional antipsychotic medications: a prospective cohort study," J Clin Psychiatry, Apr. 2010, 71(4):463-474.
Yamashita et al., "Modeling of rifampicin-induced CYP3A4 activation dynamics for the prediction of clinical drug-drug interactions in vitro data," PLoS One, 2013, 8(9):e70330, 11 pages.
Yasumoto et al., "Inhibitory effect of selective serotonin reuptake inhibitors on the vesicular monoamine transporter 2," Neuroscience Letters, May 1, 2009, 454(3):229-232.
Zhang et al, "Synergistic Effects of Olanzapine and other Antipsychotic Agents in Combination with Fluoxetine on Norepinephrine and Dopamine release in rate Prefrontal Cortex," Neuropsychopharmacology, Sep. 1, 2000, 23(3):250-262.
Cumming et al., "Deuterium tetrabenazine for tardive dyskinesia," Clinical Schizophrenia & Related Psychoses, 2018, 214-220.
Preswick Pharmaceuticals et al., "Xenazine (tetrabenazine) tablets," 2008, retrieved from URL: https://accessdatafda.gov/drugsatfda_docs/label/2011/021894s0051b1.pdj, retrieved on Jul. 28, 2020, 27 pages.
U.S. Appl. No. 17/005,425, filed Aug. 28, 2020, O'Brien.
U.S. Appl. No. 17/021,362, filed Sep. 15, 2020, O'Brien et al.

\* cited by examiner

VALBENAZINE SALTS AND POLYMORPHS THEREOF

CROSS REFERENCE TO RELATED APPLICATION

This application claims the benefit of U.S. application Ser. No. 16/662,346 filed Oct. 24, 2019, which claims the benefit of U.S. application Ser. No. 16/293,728 filed Mar. 6, 2019, which claims the benefit of U.S. application Ser. No. 16/043,059 filed Jul. 23, 2018, which claims the benefit of U.S. application Ser. No. 15/338,214 filed Oct. 28, 2016, now U.S. Pat. No. 10,065,952, which claims the benefit of U.S. Provisional Application No. 62/249,074 filed Oct. 30, 2015; the disclosure of each of which is incorporated herein by reference in its entirety.

FIELD

Provided herein are salts of (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester in amorphous and crystalline forms, processes of preparation thereof, and pharmaceutical compositions thereof. Also provided are methods of their use for treating, preventing, or ameliorating one or more symptoms of neurological disorders and diseases including hyperkinetic movement disorders or diseases.

BACKGROUND

Hyperkinetic disorders are characterized by excessive, abnormal involuntary movement. These neurologic disorders include tremor, dystonia, ballism, tics, akathisia, stereotypies, chorea, myoclonus and athetosis. Though the pathophysiology of these movement disorders is poorly understood, it is thought that dysregulation of neurotransmitters in the basal ganglia plays an important role. (Kenney et. al., *Expert Review Neurotherapeutics,* 2005, 6, 7-17). The chronic use and high dosing of typical neuropletics or centrally acting dopamine receptor blocking antiemetics predispose patients to the onset of tardive syndromes. Tardive dyskinesia, one subtype of the latter syndromes, is characterized by rapid, repetitive, stereotypic, involuntary movements of the face, limbs, or trunk. (Muller, *Expert Opin. Investig. Drugs,* 2015, 24, 737-742).

The reversible inhibition of the vesicular monoamine transporter-2 system (VMAT2) by 3-isobutyl-9,10-dimethoxy-1,3,4,6,7,11b-hexahydro-2H-pyrido[2,1-a]isoquinolin-2-one, also known as tetrabenazine (TBZ), improves the treatment of various hyperkinetic movement disorders. However, the drawbacks to such treatment are the fluctuating response, the need for frequent intake do to TBZ rapid metabolism, and side effects. Side effects associated with TBZ include sedation, depression, akathisia, and parkinsonism.

TBZ, which contains two chiral centers and is a racemic mix of two stereoisomers, is rapidly and extensively metabolized in vivo to its reduced form, 3-isobutyl-9, 10-dimethoxy-1,3,4,6,7,11b-hexahydro-2H-pyrido[2,1-a]isoquinolin-2-ol, also known as dihydrotetrabenazine (DHTBZ). DHTBZ is thought to exist as four individual isomers: (±) alpha-DHTBZ and (±) beta-DHTBZ. The 2R, 3R, 11bR or (+) alpha-DHTBZ is believed to be the absolute configuration of the active metabolite. (Kilbourn et al., *Chirality,* 1997, 9, 59-62). Tetrabenazine has orphan drug status in US and is approved in certain European countries. Its use is also allowed for therapy of chorea in patients with Hungtington's disease. However, tetrabenazine is rapidly metabolized and must frequently be administered throughout the day. (Muller, *Expert Opin. Investig. Drugs,* 2015, 24, 737-742). Therefore, there is an unmet need in the art to develop effective therapeutics for treatment of hyperkinetic movement disorders, including tardive dyskinesia.

Valbenazine, (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester, the purified prodrug of the (+)-α-isomer of dihydrotetrabenazine, recently showed a distinctive improvement in the treatment of hyperkinetic movement disorders, including tardive dyskinesia symptoms, with improved pharmacokinetic and tolerability profiles.

SUMMARY OF THE DISCLOSURE

Provided herein are pharmaceutically acceptable salts of (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester of Formula:

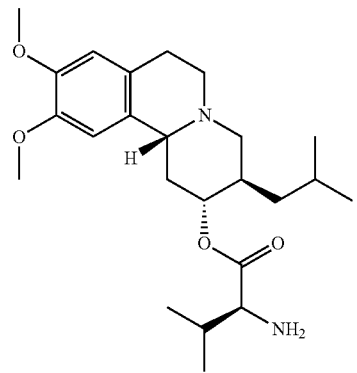 [SMILES: COc1cc2c(cc1OC)[C@H]1C[C@@H](OC(=O)[C@@H](N)C(C)C)[C@H](CC(C)C)CN1CC2]

or an isotopic variant thereof, or solvate thereof.

Provided herein is a crystalline form of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) of Formula I:

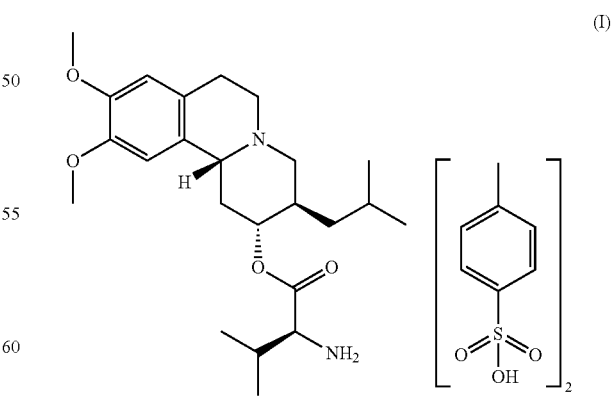

or an isotopic variant thereof, or solvate thereof.

Also provided herein are Forms I, II, III, IV, V, and VI of (S)-(2R,3R,11bR)-3-isobutyl-9,10-dimethoxy-2,3,4,6,7,11b-hexahydro-1H-pyrido[2,1-a]isoquinolin-2-yl 2-amino- 3-methylbutanoate di(4-methylbenzenesulfonate) (Formula I) or an isotopic variant thereof or solvate thereof.

Provided herein is a process for preparing a crystalline form of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) or an isotopic variant thereof, or a pharmaceutically acceptable salt or solvate thereof comprising dissolving (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) in a solvent at a first temperature.

Provided herein is a pharmaceutical composition comprising a crystalline form of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) or an isotopic variant thereof, or solvate thereof.

Provided herein is a method for the treatment, prevention, or amelioration of one or more symptoms of hyperkinetic disorder, comprising administering to a subject a pharmaceutically acceptable salt of (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl or an isotopic variant thereof, or solvate thereof.

Provided herein is a method for the treatment, prevention, or amelioration of one or more symptoms of hyperkinetic disorder, comprising administering to a subject a crystalline form of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) or an isotopic variant thereof; or solvate thereof.

Figure 1:
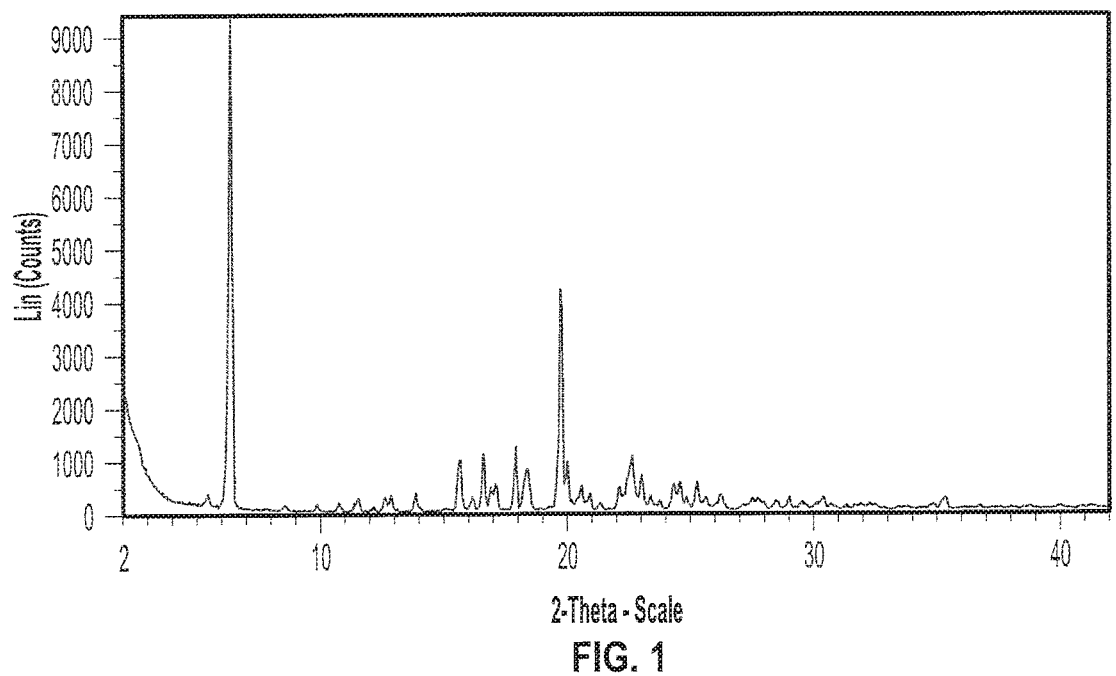
FIG. 1 depicts an exemplary X-ray powder (XRP) diffractogram of a sample of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) in crystalline Form I.

Dotted and solid lines in the Figures are for the sole purpose of distinguishing the plots and are not intended to mean intensity of signal.

DETAILED DESCRIPTION OF THE INVENTION

Definitions

To facilitate understanding of the disclosure set forth herein, a number of terms are defined below.

Generally, the nomenclature used herein and the laboratory procedures in organic chemistry, medicinal chemistry, and pharmacology described herein are those well known and commonly employed in the art. Unless defined otherwise, all technical and scientific terms used herein generally have the same meaning as commonly understood by one of ordinary skill in the art to which this disclosure belongs.

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject, in one embodiment, a human.

As used herein, "isotopically enriched" refers to an atom having an isotopic composition other than the natural isotopic composition of that atom. "Isotopically enriched" may also refer to a compound containing at least one atom having an isotopic composition other than the natural isotopic composition of that atom.

With regard to the compounds provided herein, when a particular atomic position is designated as having deuterium or "D," it is understood that the abundance of deuterium at that position is substantially greater than the natural abundance of deuterium, which is about 0.015%. A position designated as having deuterium typically has a minimum isotopic enrichment factor of, in particular embodiments, at least 1000 (15% deuterium incorporation), at least 2000 (30% deuterium incorporation), at least 3000 (45% deuterium incorporation), at least 3500 (52.5% deuterium incorporation), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation) at each designated deuterium position.

The isotopic enrichment of the compounds provided herein can be determined using conventional analytical methods known to one of ordinary skill in the art, including mass spectrometry, nuclear magnetic resonance spectroscopy, and crystallography.

Isotopic enrichment (for example, deuteration) of pharmaceuticals to improve pharmacokinetics ("PK"), pharmacodynamics ("PD"), and toxicity profiles, has been demonstrated previously with some classes of drugs. See, for example, Lijinsky et. al., *Food Cosmet. Toxicol.*, 20: 393 (1982); Lijinsky et. al., *J. Nat. CancerInst.*, 69: 1127 (1982); Mangold et. al., *Mutation Res.* 308: 33 (1994); Gordon et. al., *Drug Metab. Dispos.*, 15: 589 (1987); Zello et. al., *Metabolism*, 43: 487 (1994); Gately et. al., *J. Nucl. Med.*, 27: 388 (1986); Wade D, *Chem. Biol. Interact.* 117: 191 (1999).

Isotopic enrichment of a drug can be used, for example, to (1) reduce or eliminate unwanted metabolites, (2) increase the half-life of the parent drug, (3) decrease the number of doses needed to achieve a desired effect, (4) decrease the amount of a dose necessary to achieve a desired effect, (5) increase the formation of active metabolites, if any are formed, and/or (6) decrease the production of deleterious metabolites in specific tissues and/or create a more effective drug and/or a safer drug for combination therapy, whether the combination therapy is intentional or not.

Replacement of an atom for one of its isotopes often will result in a change in the reaction rate of a chemical reaction. This phenomenon is known as the Kinetic Isotope Effect ("KIE"). For example, if a C—H bond is broken during a rate-determining step in a chemical reaction (i.e. the step with the highest transition state energy), substitution of a deuterium for that hydrogen will cause a decrease in the reaction rate and the process will slow down. This phenomenon is known as the Deuterium Kinetic Isotope Effect ("DKIE"). (See, e.g., Foster et al., *Adv. Drug Res.*, vol. 14, pp. 1-36 (1985); Kushner et al., *Can. J. Physiol. Pharmacol.*, vol. 77, pp. 79-88 (1999)).

The magnitude of the DKIE can be expressed as the ratio between the rates of a given reaction in which a C—H bond is broken, and the same reaction where deuterium is substituted for hydrogen. The DKIE can range from about 1 (no isotope effect) to very large numbers, such as 50 or more, meaning that the reaction can be fifty, or more, times slower when deuterium is substituted for hydrogen. High DKIE values may be due in part to a phenomenon known as tunneling, which is a consequence of the uncertainty principle. Tunneling is ascribed to the small mass of a hydrogen atom, and occurs because transition states involving a proton can sometimes form in the absence of the required activation energy. Because deuterium has more mass than hydrogen, it statistically has a much lower probability of undergoing this phenomenon.

Tritium ("T") is a radioactive isotope of hydrogen, used in research, fusion reactors, neutron generators and radiopharmaceuticals. Tritium is a hydrogen atom that has 2 neutrons in the nucleus and has an atomic weight close to 3. It occurs naturally in the environment in very low concentrations, most commonly found as $T_2O$. Tritium decays slowly (half-life=12.3 years) and emits a low energy beta particle that cannot penetrate the outer layer of human skin. Internal exposure is the main hazard associated with this isotope, yet it must be ingested in large amounts to pose a significant health risk. As compared with deuterium, a lesser amount of tritium must be consumed before it reaches a hazardous level. Substitution of tritium ("T") for hydrogen results in yet a stronger bond than deuterium and gives numerically larger isotope effects. Similarly, substitution of isotopes for other elements, including, but not limited to, $^{13}C$ or $^{14}C$ for carbon, $^{33}S$, $^{34}S$, or $^{36}S$ for sulfur, $^{15}N$ for nitrogen, and $^{17}O$ or $^{18}O$ for oxygen, may lead to a similar kinetic isotope effect.

For example, the DKIE was used to decrease the hepatotoxicity of halothane by presumably limiting the production of reactive species such as trifluoroacetyl chloride. However, this method may not be applicable to all drug classes. For example, deuterium incorporation can lead to metabolic switching. The concept of metabolic switching asserts that xenogens, when sequestered by Phase I enzymes, may bind transiently and re-bind in a variety of conformations prior to the chemical reaction (e.g., oxidation). This hypothesis is supported by the relatively vast size of binding pockets in many Phase I enzymes and the promiscuous nature of many metabolic reactions. Metabolic switching can potentially lead to different proportions of known metabolites as well as altogether new metabolites. This new metabolic profile may impart more or less toxicity.

The animal body expresses a variety of enzymes for the purpose of eliminating foreign substances, such as therapeutic agents, from its circulation system. Examples of such enzymes include the cytochrome P450 enzymes ("CYPs"), esterases, proteases, reductases, dehydrogenases, and monoamine oxidases, to react with and convert these foreign substances to more polar intermediates or metabolites for renal excretion. Some of the most common metabolic reactions of pharmaceutical compounds involve the oxidation of a carbon-hydrogen (C—H) bond to either a carbon-oxygen (C—O) or carbon-carbon (C—C) pi-bond. The resultant metabolites may be stable or unstable under physiological conditions, and can have substantially different pharmacokinetic, pharmacodynamic, and acute and long-term toxicity profiles relative to the parent compounds. For many drugs, such oxidations are rapid. These drugs therefore often require the administration of multiple or high daily doses.

Therefore, isotopic enrichment at certain positions of a compound provided herein will produce a detectable KIE that will affect the pharmacokinetic, pharmacologic, and/or toxicological profiles of a compound provided herein in comparison with a similar compound having a natural isotopic composition.

The term "isotopic variant" refers to a therapeutic agent that contains an unnatural proportion of an isotope at one or more of the atoms that constitute such a therapeutic agent. In certain embodiments, an "isotopic variant" of a therapeutic agent contains unnatural proportions of one or more isotopes, including, but not limited to, hydrogen (H), deuterium ($^2$H), tritium ($^3$H), carbon-11 ($^{11}$C), carbon-12 ($^{12}$C), carbon-13 ($^{13}$C), carbon-14 ($^{14}$C), nitrogen-13 ($^{13}$N), nitrogen-14 ($^{14}$N), nitrogen-15 ($^{15}$N), oxygen-14 ($^{14}$O), oxygen-15 ($^{15}$O), oxygen-16 ($^{16}$O), oxygen-17 ($^{17}$O), oxygen-18 ($^{18}$O), fluorine-17 ($^{17}$F), fluorine-18 ($^{11}$F), phosphorus-31 ($^{31}$P), phosphorus-32 ($^{32}$P), phosphorus-33 ($^{33}$P), sulfur-32 ($^{32}$S), sulfur-33 ($^{33}$S), sulfur-34 ($^{34}$S), sulfur-35 ($^{35}$S), sulfur-36 ($^{36}$S), chlorine-35 ($^{35}$Cl), chlorine-36 ($^{36}$Cl), chlorine-37 ($^{37}$Cl), bromine-79 ($^{79}$Br), bromine-81 ($^{81}$Br), iodine 123 ($^{123}$I), iodine-125 ($^{125}$I), iodine-127 ($^{127}$I), iodine-129 ($^{129}$I), and iodine-131 ($^{131}$I). In certain embodiments, an "isotopic variant" of a therapeutic agent contains unnatural proportions of one or more isotopes, including, but not limited to, hydrogen ($^1$H), deuterium ($^2$H), tritium ($^3$H), carbon-11 ($^{11}$C), carbon-12 ($^{12}$C), carbon-13 ($^{13}$C), carbon-14 ($^{14}$C), nitrogen-13 ($^{13}$N), nitrogen-14 ($^{14}$N), nitrogen-15 ($^{15}$N), oxygen-14 ($^{14}$O), oxygen-15 ($^{15}$O), oxygen-16 ($^{16}$O), oxygen-17 ($^{17}$O), oxygen-18 ($^{18}$O), fluorine-17 ($^{17}$F), fluorine-18 ($^{18}$F), phosphorus-31 ($^{31}$P), phosphorus-32 ($^{32}$P), phosphorus-33 ($^{33}$P), sulfur-32 ($^{32}$S), sulfur-33 ($^{33}$S), sulfur-34 ($^{34}$S), sulfur-35 ($^{35}$S), sulfur-36 ($^{36}$S), chlorine-35 ($^{35}$Cl), chlorine-36 ($^{36}$Cl), chlorine-37 ($^{37}$Cl), bromine-79 ($^{79}$Br), bromine-81 ($^{81}$Br), iodine 123 ($^{123}$I), iodine-125 ($^{125}$I), iodine-127 ($^{127}$I), iodine-129 ($^{129}$I), and iodine-131 ($^{131}$I).

It will be understood that, in a therapeutic agent, any hydrogen can be $^2$H, for example, or any carbon can be $^{13}$C, for example, or any nitrogen can be $^{15}$N, for example, or any oxygen can be $^{18}$O, for example, where feasible according to the judgment of one of skill. In certain embodiments, an "isotopic variant" of a therapeutic agent contains unnatural proportions of deuterium (D).

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

As used herein, and unless otherwise specified, the terms "manage," "managing" and "management" refer to preventing or slowing the progression, spread or worsening of a disease or disorder, or of one or more symptoms thereof. Often, the beneficial effects that a subject derives from a prophylactic and/or therapeutic agent do not result in a cure of the disease or disorder. In this regard, the term "managing" encompasses treating a subject who had suffered from the particular disease in an attempt to prevent or minimize the recurrence of the disease.

As used herein, amelioration of the symptoms of a particular disorder by administration of a particular pharmaceutical composition refers to any lessening, whether permanent or temporary, lasting or transient, that can be attributed to or associated with administration of the composition.

The term "disorder" as used herein is intended to be generally synonymous, and is used interchangeably with, the terms "disease", "syndrome", and "condition" (as in medical condition), in that all reflect an abnormal condition of the human or animal body or of one of its parts that impairs normal functioning, is typically manifested by distinguishing signs and symptoms.

The term "therapeutically effective amount" are meant to include the amount of a compound that, when administered, is sufficient to prevent development of, or alleviate to some extent, one or more of the symptoms of the disorder, disease, or condition being treated. The term "therapeutically effective amount" also refers to the amount of a compound that is sufficient to elicit the biological or medical response of a biological molecule (e.g., a protein, enzyme, RNA, or DNA), cell, tissue, system, animal, or human, which is being sought by a researcher, veterinarian, medical doctor, or clinician.

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with one or more other agent(s), which provides a prophylactic benefit in the prevention of the disease. The term "prophylactically effective amount" can encompass an amount that improves overall prophylaxis or enhances the prophylactic efficacy of another prophylactic agent.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, Remington: *The Science and Practice of Pharmacy,* 22nd ed.; Pharmaceutical Press: 2012; *Handbook of Pharmaceutical Excipients,* 7th ed.; Rowe et al., Eds.; The Pharmaceutical Press: 2012; Handbook of Pharmaceutical Additives, 3rd ed.; Ash and Ash Eds.; Gower Publishing Company: 2007; *Pharmaceutical Preformulation and Formulation,* 2nd ed.; Gibson Ed.; CRC Press LLC: Boca Raton, Fla., 2009.

As used in the specification and the accompanying claims, the indefinite articles "a" and "an" and the definite article "the" include plural as well as singular referents, unless the context clearly dictates otherwise.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, or 0.05% of a given value or range. In certain embodiments, "about" or "approximately" with reference to X-ray powder diffraction two-theta peaks means within 0.2°.

The terms "active ingredient" and "active substance" refer to a compound, which is administered, alone or in combination with one or more pharmaceutically acceptable excipients, to a subject for treating, preventing, or ameliorating one or more symptoms of a disorder, disease, or condition. As used herein, "active ingredient" and "active substance" may be an optically active isomer or an isotopic variant of a compound described herein.

The term "anti-solvent" refers to a liquid that is added to a solvent to reduce the solubility of a compound in that solvent, in some instances, resulting in precipitation of the compound.

The terms "drug," "therapeutic agent," and "chemotherapeutic agent" refer to a compound, or a pharmaceutical composition thereof, which is administered to a subject for treating, preventing, or ameliorating one or more symptoms of a disorder, disease, or condition.

The term "solvate" refers to a complex or aggregate formed by one or more molecules of a solute, e.g., a compound provided herein, and one or more molecules of a solvent, which present in stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a noncrystalline form. Where the solvent is water, the solvate is a hydrate. Examples of hydrates include, but are not limited to, a hemihydrate, monohydrate, dihydrate, trihydrate, tetrahydrate, and pentahydrate.

The term "crystalline form" of a compound can refer to any crystalline form of the compound as a free acid, the compound as a free base, as an acid addition salt of the compound, an base addition salt of the compound, a complex of the compound, a solvate (including hydrate) of the compound, or a co-crystal of the compound. The term "solid form" of a compound can refer to any crystalline form of the compound or any amorphous form of the compound as a free acid, the compound as a free base, as an acid addition salt of the compound, an base addition salt of the compound, a complex of the compound, or a solvate (including hydrate) of the compound, or a co-precipitation of the compound. In many instances, the terms "crystalline form" and "solid form" can refer to those that are pharmaceutically acceptable, including, for example, those of pharmaceutically acceptable addition salts, pharmaceutically acceptable complexes, pharmaceutically acceptable solvates, pharmaceutically acceptable co-crystals, and pharmaceutically acceptable co-precipitations.

The term "stereotyped" refers to a repeated behavior that appears repetitively with slight variation or, less commonly, as a complex series of movements.

The term "hyperkinetic disorder" or "hyperkinetic movement disorder" or "hyperkinesias" refers to disorders or diseases characterized by excessive, abnormal, involuntary movements. These disorders include but are not limited to Huntington's disease, tardive dyskinesia, Tourette syndrome, dystonia, hemiballismus, chorea, senile chorea, or tics.

The term "neurological disorder" or "neurological disease" include but is not limited to hyperkinetic disorder, bipolar disorder, major depressive disorder, anxiety, attention-deficit hyperactivity disorder, dementia, depression, insomnia, psychosis, post-traumatic stress disorder, substance abuse, Parkinson's disease levodopa-induced dyskinesia, movement disorders, or oppositional defiant disorder.

The term "tardive syndrome" encompasses but is not limited to tardive dyskinesia, tardive dystonia, tardive akathisia, tardive tics, myoclonus, tremor and withdrawal-emergent syndrome.

The term "VMAT2" refers to human vesicular monoamine transporter isoform 2, an integral membrane protein that acts to transport monoamines, particularly neurotransmitters such as dopamine, norepinephrine, serotonin, and histamine, from cellular cytosol into synaptic vesicles.

The term "VMAT2-mediated disorder," refers to a disorder that is characterized by abnormal VMAT2 activity, or VMAT2 activity that, when modulated, leads to the amelioration of other abnormal biological processes. A VMAT2-mediated disorder may be completely or partially mediated by modulating VMAT2. In particular, a VMAT2-mediated disorder is one in which inhibition of VMAT2 results in some effect on the underlying disorder e.g., administration of a VMAT2 inhibitor results in some improvement in at least some of the patients being treated.

The term "VMAT2 inhibitor", "inhibit VMAT2", or "inhibition of VMAT2" refers to the ability of a compound disclosed herein to alter the function of VMAT2. A VMAT2 inhibitor may block or reduce the activity of VMAT2 by forming a reversible or irreversible covalent bond between the inhibitor and VMAT2 or through formation of a noncovalently bound complex. Such inhibition may be manifest only in particular cell types or may be contingent on a particular biological event. The term "VMAT2 inhibitor", "inhibit VMAT2", or "inhibition of VMAT2" also refers to altering the function of VMAT2 by decreasing the probability that a complex forms between a VMAT2 and a natural substrate. In some embodiments, modulation of the VMAT2 may be assessed using the method described in WO 2005/077946; WO 2008/058261; EP 1716145; Kilbourn et al., *European Journal of Pharmacology* 1995, (278), 249-252; Lee et al., *J. Med. Chem.*, 1996, (39), 191-196; Scherman et al., *Journal of Neurochemistry* 1988, 50(4), 1131-36; Kilbourn et al., *Synapse* 2002, 43(3), 188-194; Kilbourn et al., *European Journal of Pharmacology* 1997, 331(2-3), 161-68; and Erickson et al., *Journal of Molecular Neuroscience* 1995, 6(4), 277-87.

"Pharmaceutically acceptable salt" refers to any salt of a compound provided herein which retains its biological properties and which is not toxic or otherwise undesirable for pharmaceutical use. Such salts may be derived from a variety of organic and inorganic counter-ions well known in the art. Such salts include, but are not limited to: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; or (2) salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, aluminum, lithium, zinc, and barium hydroxide, ammonia, or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like.

Pharmaceutically acceptable salts further include, by way of example only and without limitation, sodium, potassium, calcium, magnesium, ammonium, tetraalkylammonium, and the like, and when the compound contains a basic functionality, salts of non-toxic organic or inorganic acids, such as hydrohalides, e.g. hydrochloride and hydrobromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate, and the like.

The term "amino acid" refers to naturally occurring and synthetic α, β, γ, or δ amino acids, and includes but is not limited to, amino acids found in proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In one embodiment, the amino acid is in the L-configuration. Alternatively, the amino acid can be a derivative of alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleuccinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl, or β-histidinyl.

Solid Forms

In one embodiment, provided herein are pharmaceutically acceptable salts of (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester or an isotopic variant thereof. (S)-2-amino-3-methyl-butyric acid (2R,3R,1bR)-3-isobutyl-9,10-dimethoxy-1,3,4,6,7,11b-hexahydro-2H-pyrido[2,1-a]isoquinolin-2-yl ester has the structure of Formula:

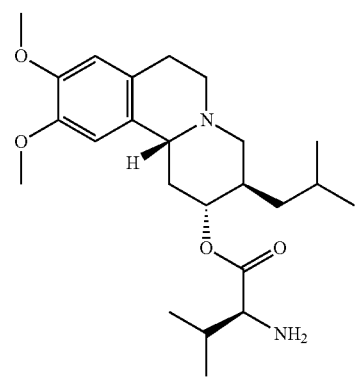 [SMILES: COc1cc2c(cc1OC)[C@H]1C[C@@H](OC(=O)[C@@H](N)C(C)C)[C@H](CC(C)C)CN1CC2]

The compound (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester, also known as valbenazine, can be prepared according to U.S. Pat. Nos. 8,039,627 and 8,357,697, the disclosure of each of which is incorporated herein by reference in its entirety.

Valbenazine Ditosylate

In another embodiment, provided herein is a crystalline form of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) or an isotopic variant thereof or solvate thereof of Formula I:

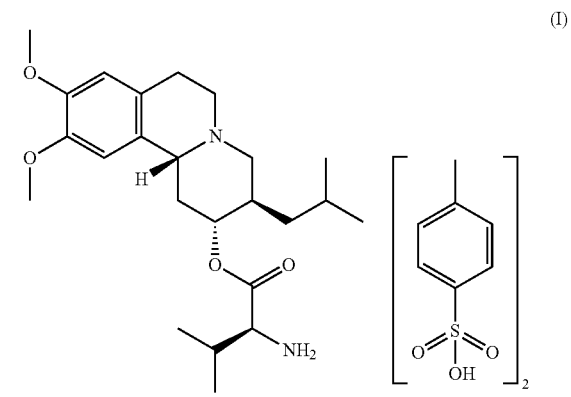

The crystalline forms as shown herein (e.g., of Formula I) may be characterized using a number of methods known to a person skilled in the art, including single crystal X-ray diffraction, X-ray powder diffraction (XRPD), microscopy (e.g., scanning electron microscopy (SEM)), thermal analysis (e.g., differential scanning calorimetry (DSC), thermal gravimetric analysis (TGA), and hot-stage microscopy, and spectroscopy (e.g., infrared, Raman, solid-state nuclear magnetic resonance). The particle size and size distribution may be determined by conventional methods, such as laser light scattering technique. The purity of the crystalline forms provided herein may be determined by standard analytical methods, such as thin layer chromatography (TLC), gel electrophoresis, gas chromatography, high performance liquid chromatography (HPLC), and mass spectrometry (MS).

Valbenazine Ditosylate Form I

In yet another embodiment, provided herein is a crystalline form of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) or an isotopic variant thereof or solvate thereof, wherein the crystalline form is Form I.

In various embodiments, crystalline Form I of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) has an X-ray diffraction pattern. In some embodiments, the X-ray diffraction pattern of Form I of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) includes an XRP diffraction peak at two-theta angles of approximately 6.3, 17.9, and 19.7°. In some embodiments, the X-ray powder diffraction pattern of Form I of (S)-(2R,3R,1bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) includes an XRP diffraction peak at two-theta angles of approximately 6.3, 17.9, or 19.7°. In another embodiment, crystalline Form I of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) includes an XRP diffraction peak at two-theta angles of approximately 6.3° and 19.7°. In another embodiment, crystalline Form I of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) includes an XRP diffraction peak at two-theta angles of approximately 6.3°. In certain embodiments, crystalline Form I of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) has an X-ray diffraction pattern substantially as shown in FIG. 1.

In some embodiments, crystalline Form I has one or more characteristic XRP diffraction peaks at two-theta angles of approximately 6.3° and approximately 19.7°. In certain embodiments, crystalline Form I has one or more characteristic XRP diffraction peaks at two-theta angles of approximately 6.3°, approximately 17.9°, and approximately 19.7°. In some embodiments, crystalline Form I has one or more characteristic XRP diffraction peaks at two-theta angles of approximately 6.3°, approximately 17.9°, approximately 19.7°, and approximately 22.7°. In certain embodiments, crystalline Form I has one or more characteristic XRP diffraction peaks at two-theta angles of approximately 6.3°, approximately 15.6°, approximately 17.9°, approximately 19.7°, and approximately 22.7°. In some embodiments, crystalline Form I has one or more characteristic XRP diffraction peaks at two-theta angles of approximately 6.3°, approximately 15.6°, approximately 16.6°, approximately 17.9°, approximately 19.7°, and approximately 22.7°.

Figure 2:
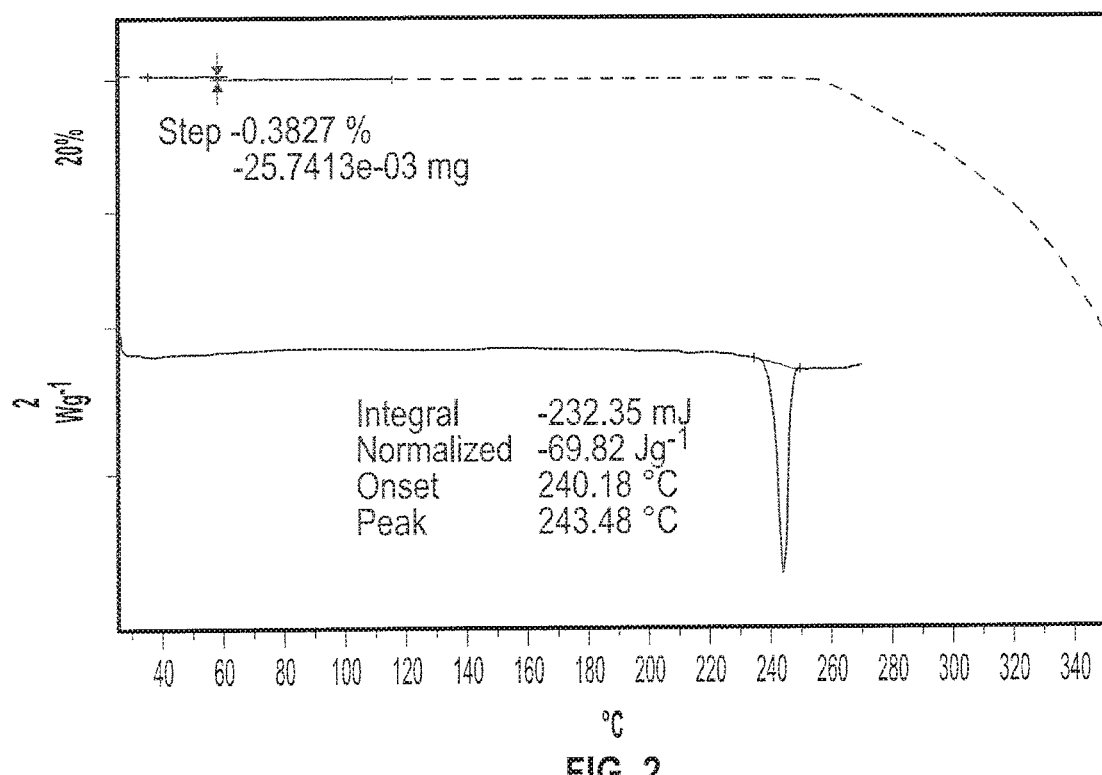
FIG. 2 depicts exemplary Thermogravimetric Analysis (TGA) thermogram (dotted line) and Differential Scanning Calorimetry (DSC) diffractogram (solid line) of a sample of Formula I in crystalline Form I.

In various embodiments, crystalline Form I has an endothermic differential scanning calorimetric (DSC) thermogram. In some embodiments, crystalline Form I has a DSC thermogram comprising an endothermic event with an onset temperature of about 240° C. and a peak at about 243° C. In yet another embodiment, crystalline Form I has a DSC thermogram substantially as shown in FIG. 2. In yet another embodiment, crystalline Form I has a thermal gravimetric analysis (TGA) plot comprising a mass loss of less than about 0.4% when heated from about 25° C. to about 140° C. In still another embodiment, crystalline Form I has a TGA plot substantially as shown in FIG. 2.

Figure 3:
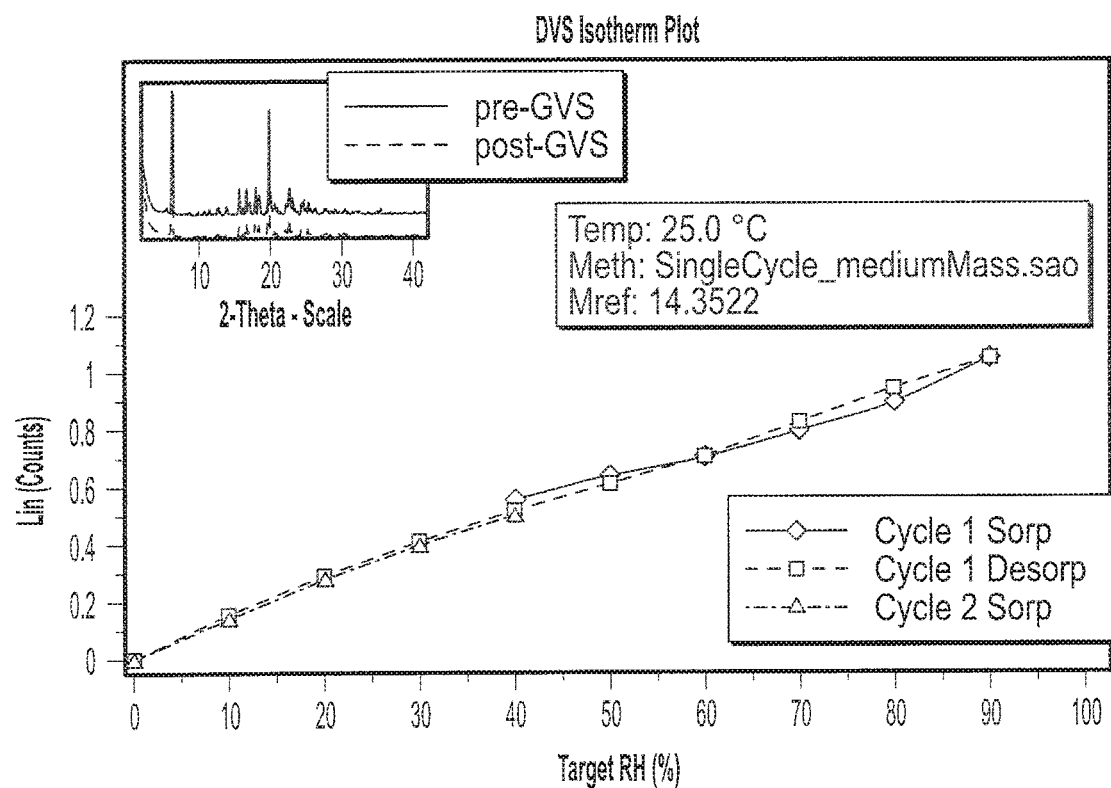
FIG. 3 depicts an exemplary Gravimetric Vapor Sorption (GVS) of a sample of Formula I in crystalline Form I.

In various embodiments, crystalline Form I has a gravimetric vapor system (GVS) plot. In some embodiments, crystalline Form I exhibit a mass increase of about 1% when subjected to a an increase in relative humidity from about 0% to about 95% relative humidity. In certain embodiments mass gained upon adsorption is lost when the relative humidity (RH) is decreased back to about 0% RH. In yet another embodiment, crystalline Form I exhibit a gravimetric vapor system plot substantially as shown in FIG. 3. In still another embodiment, crystalline Form I is stable upon exposure to about 25° C. and about 60% relative humidity. In yet another embodiment, crystalline Form I is stable upon exposure to about 25° C. and about 60% relative humidity for about 24 months. Also in another embodiment, crystalline Form I is stable upon exposure to about 25° C. and about 60% relative humidity for about 3 months. In still another embodiment, crystalline Form I is stable upon exposure to about 25° C. and about 92% relative humidity. In an another embodiment, crystalline Form I is stable upon exposure to about 40° C. and about 75% relative humidity. In an another embodiment, crystalline Form I is stable upon exposure to about 40° C. and about 75% relative humidity for about 6 months. In an another embodiment, crystalline Form I is stable upon exposure to about 40° C. and about 75% relative humidity for about 3 months.

In certain embodiments, crystalline form of Formula I in Form I may contain no less than about 95%, no less than about 97%, no less than about 98%, no less than about 99%, or no less than about 99.5% by weight of the salt of Formula I. The crystalline form may also contain no less than about 90%, no less than about 95%, no less than about 98%, no less than about 99%, or no less than about 99.5% by weight of crystal Form I.

In certain embodiments, crystalline Form I has an aqueous solubility of about 17.58, about 18.58, about 19.58, about 26.75, about 26.87, about 26.96, about 27.06, about 27.75, about 27.87, about 27.97, about 28.06, about 28.75, about 28.87, about 28.97, about 29.06, about 27.45, about 28.45, about 29.45, about 30.61, about 31.61, about 32.61, about 32.17, about 32.98, about 33.17, about 33.98, about 34.17, about 34.35, about 34.98, about 35.35, about 36.35 mg/mL. In certain embodiments, crystalline Form I has an aqueous solubility of about 31.61 and about 33.17 at approximately pH 1.2; about 28.45 and about 27.97 at approximately pH 3; about 28.06 and about 27.77 at approximately pH 4; about 18.58 and about 27.87 at approximately pH 5; about 33.98 and about 35.35 at approximately pH 6.8.

In certain embodiments, crystalline Form I may contain no greater than about 0.1%, no greater than about 0.11%, no greater than about 0.12%, no greater than about 0.13%, no greater than about 0.14%, no greater than about 0.15%, no greater than about 0.16%, no greater than about 0.17%, no greater than about 0.18%, no greater than about 0.19%, no greater than about 0.2%, no greater than about 0.21%, no greater than about 0.22%, no greater than about 0.23%, no greater than about 0.24%, no greater than about 0.25%, no greater than about 0.26%, no greater than about 0.27%, no greater than about 0.28%, no greater than about 0.29%, no greater than about 0.3%, no greater than about 0.31%, no greater than about 0.32%, no greater than about 0.33%, no greater than about 0.34%, no greater than about 0.35%, no greater than about 0.36%, no greater than about 0.37%, no greater than about 0.38%, no greater than about 0.39%, no greater than about 0.4%, no greater than about 0.5%, no greater than about 0.6%, no greater than about 0.7%, no greater than about 0.8%, no greater than about 0.9%, no greater than about 1%, no greater than about 2%, no greater than about 3%, no greater than about 4%, or no greater than about 5% water by weight.

In certain embodiments Form I may be characterized by particle analysis. In certain embodiments, a sample of Form I comprises particles having rhomboid crystal morphology. In yet another embodiment, a sample of Form I comprises particles of about 100, about 90, about 80, about 70, about 60, about 50, about 40, about 30, about 20, about 10, about 5 µM in length. In some embodiments, a sample of Form I comprises particles of about 70, about 60, about 40, about 20, about 10 µM in length. In other embodiments, a sample of Form I comprises particles of about 69.39, about 56.22, about 34.72, about 17.84, about 10.29 µM in length.

Valbenazine Ditosylate Form II

In another embodiment, is a crystalline form of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) or an isotopic variant thereof or solvate thereof, wherein the crystalline form is Form II.

Figure 5:
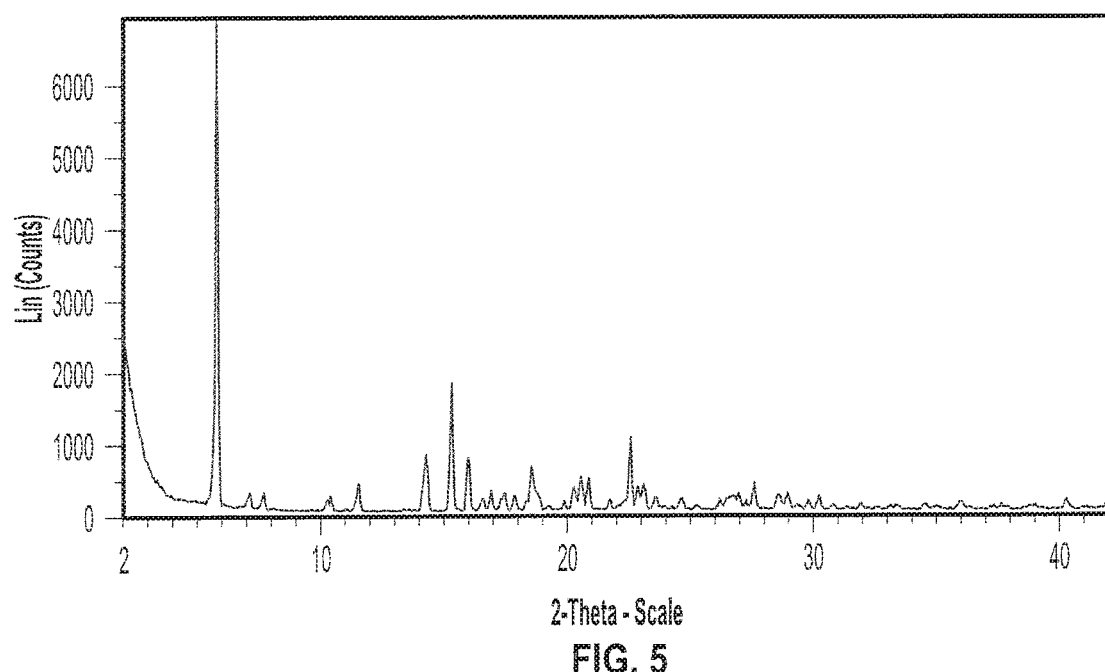
FIG. 5 depicts an exemplary X-ray powder (XRP) diffractogram of a sample of Formula I in crystalline Form II.

In various embodiments, crystalline Form II of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) has an X-ray diffraction pattern. In some embodiments, the X-ray diffraction pattern of Form II of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) includes an XRP diffraction peak at two-theta angles of approximately 5.7, 15.3, and 22.5°. In some embodiments, the X-ray powder diffraction pattern of Form II of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) includes an XRP diffraction peak at two-theta angles of approximately 5.7, 15.3, or 22.5°. In other embodiments, the X-ray powder diffraction pattern of Form II of (S)-(2R,3R,1bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) includes an XRP diffraction peak at two-theta angles of approximately 5.7 and 15.3°. In some embodiments, the X-ray powder diffraction pattern of Form II of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) includes an XRP diffraction peak at two-theta angles of approximately 5.7°. In certain embodiments, crystalline Form II of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) has an X-ray diffraction pattern substantially as shown in FIG. 5.

In some embodiments, crystalline Form II has one or more characteristic XRP diffraction peaks at two-theta angles of approximately 5.7 and 15.3°. In certain embodiments, crystalline Form II has one or more characteristic XRP diffraction peaks at two-theta angles of approximately 5.7°, approximately 15.3°, and approximately 22.5°. In some embodiments, crystalline Form II has one or more characteristic XRP diffraction peaks at two-theta angles of approximately 5.7°, approximately 14.2°, approximately 15.3°, and approximately 22.5°. In other embodiments, crystalline Form II has one or more characteristic XRP diffraction peaks at two-theta angles of approximately 5.7°, approximately 14.2°, approximately 15.3°, approximately 15.9°, and approximately 22.5°. In yet other embodiments, crystalline Form II has one or more characteristic XRP diffraction peaks at two-theta angles of approximately 5.7°, approximately 14.2°, approximately 15.3°, approximately 15.9°, approximately 18.6°, and approximately 22.5°.

In various embodiments, crystalline Form II has an endothermic differential scanning calorimetric (DSC) thermogram. In some embodiments, crystalline Form II has a DSC thermogram comprising an endothermic event with an onset temperature of about 143° C. and a peak at about 155° C.; and another endothermic event with an onset temperature of about 232° C. and a peak at about 235° C.

Figure 6A:
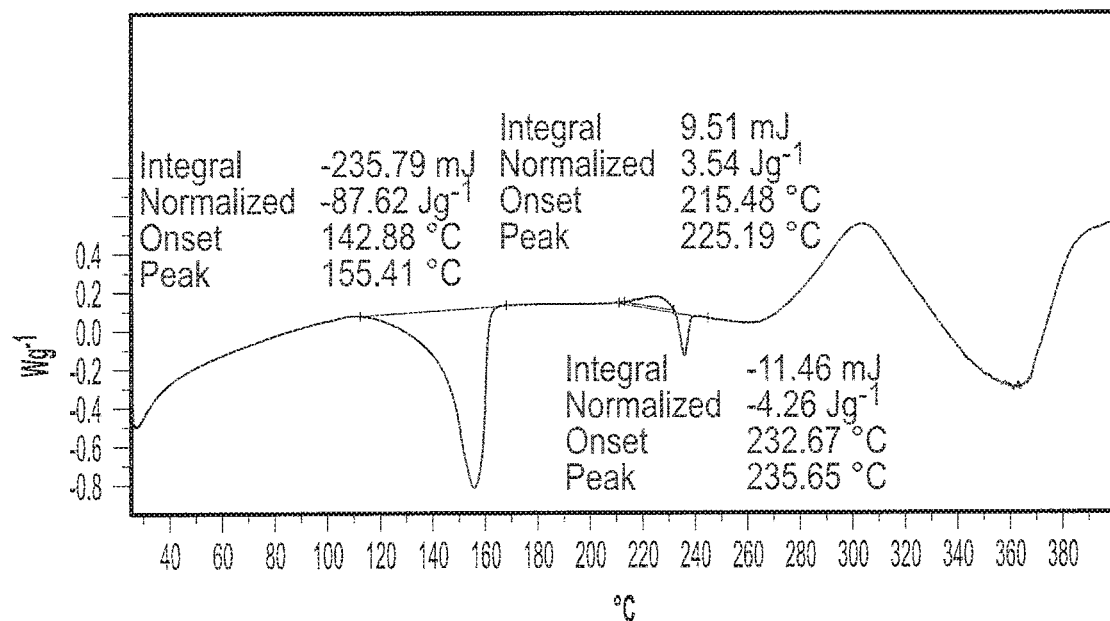
FIG. 6A depicts an exemplary Differential Scanning Calorimetry (DSC) diffractogram of a sample of Formula I in crystalline Form II.
Figure 6B:
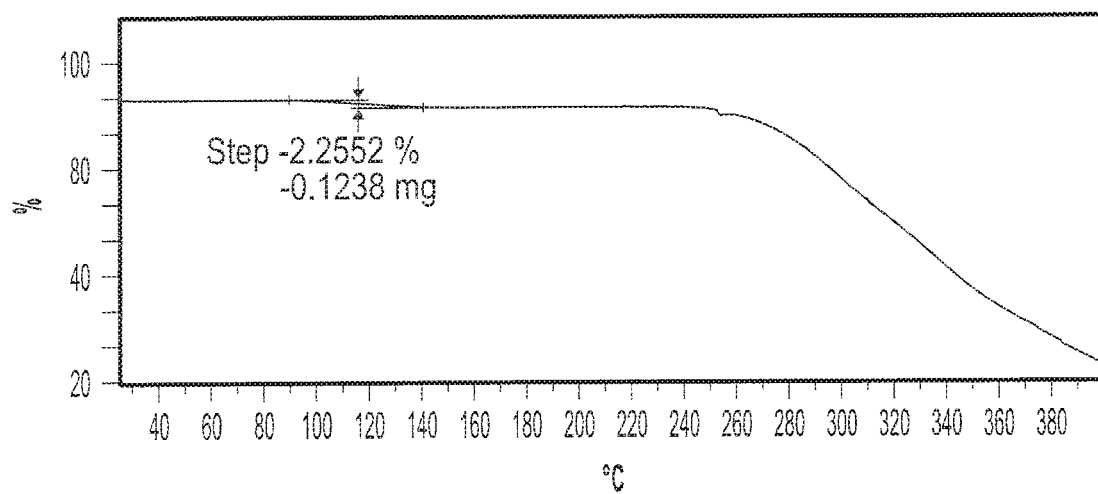
FIG. 6B depicts an exemplary Thermogravimetric Analysis (TGA) thermogram of a sample of Formula I in crystalline Form II.

In yet another embodiment, crystalline Form II has a DSC thermogram substantially as shown in FIG. 6. In yet another embodiment, crystalline Form II has a thermal gravimetric analysis (TGA) plot comprising a mass loss of about 2.2% when heated from about 25° C. to about 140° C. In still another embodiment, crystalline Form II has a TGA plot substantially as shown in FIG. 6.

Figure 7:
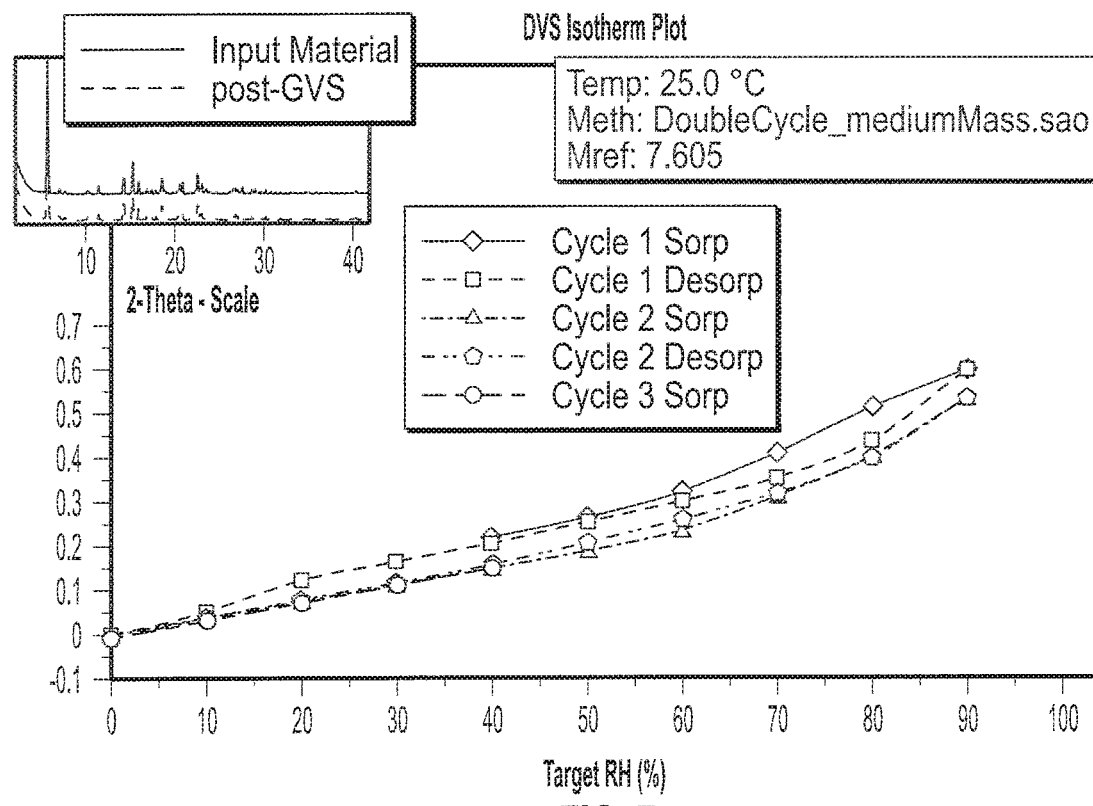
FIG. 7 depicts an exemplary Gravimetric Vapor Sorption (GVS) of a sample of Formula I in crystalline Form II.

In various embodiments, crystalline Form II has a gravimetric vapor system (GVS) plot. In some embodiments, crystalline Form II exhibit a mass increase of about 0.5% when subjected to a an increase in relative humidity from about 0% to about 95% relative humidity. In certain embodiments mass gained upon adsorption is lost when the relative humidity (RH) is decreased back to about 0% RH. In yet another embodiment, crystalline Form II exhibit a gravimetric vapor system plot substantially as shown in FIG. 7. In certain embodiments, Form II is substantially non-hygroscopic. In certain embodiments, the XRPD pattern of Form II material is substantially unchanged following the adsorption/desorption analysis. In certain embodiments, Form II is stable with respect to humidity. In still another embodiment, crystalline Form II has aqueous solubility of about 18.5 mg/mL at pH 5.1.

In certain embodiments Form II may be characterized by particle analysis. In certain embodiments, a sample of Form II comprises particles having birefringent lath shaped morphology. In yet another embodiment, a sample of Form II comprises particles of about 100, about 90, about 80, about 70, about 60, about 50, about 40, about 30, about 20, about 10, about 5 µM in length. In some embodiments, a sample of Form II comprises particles of about 100, about 70, about 60, about 40, about 20, about 10 µM in length. In yet another embodiment, a sample of Form II comprises particles of about 100 µM in length.

In certain embodiments, crystalline form of Formula I in Form II may contain no less than about 95%, no less than about 97%, no less than about 98%, no less than about 99%, or no less than about 99.5% by weight of the salt of Formula I. The crystalline form may also contain no less than about 90%, no less than about 95%, no less than about 98%, no less than about 99%, or no less than about 99.5% by weight of crystal Form II.

Valbenazine Ditosylate Form III

In another embodiment, is a crystalline form of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) or an isotopic variant thereof or solvate thereof, wherein the crystalline form is Form III.

In various embodiments, crystalline Form III of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) has an X-ray diffraction pattern. In some embodiments, the X-ray diffraction pattern of Form III of (S)-(2R,3R,11bR)-

Figure 8:
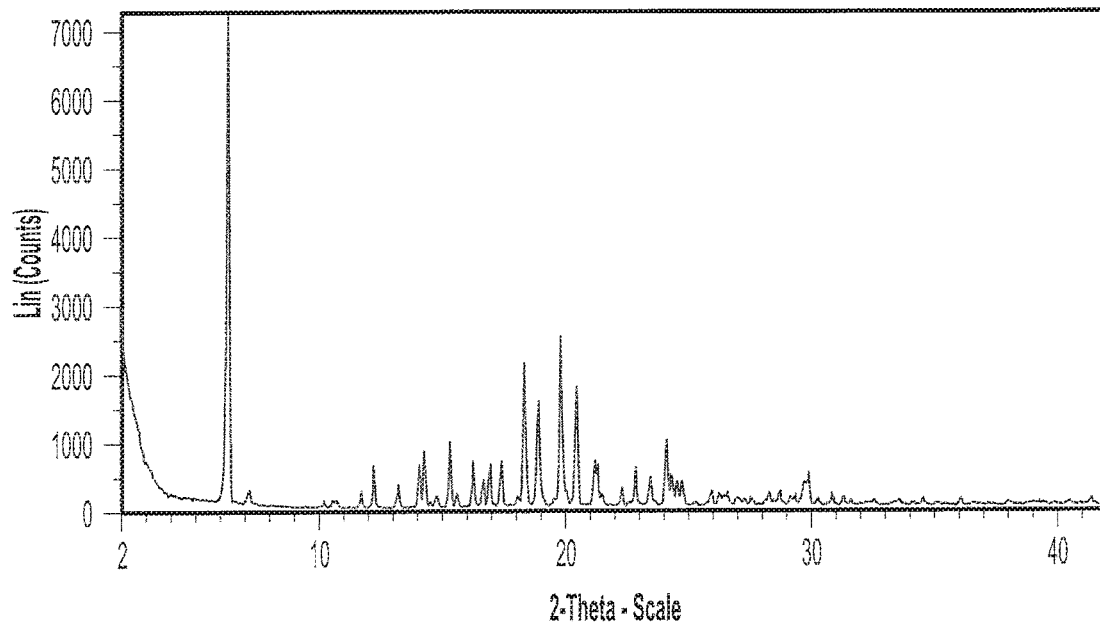
FIG. 8 depicts an exemplary X-ray powder (XRP) diffractogram of a sample of Formula I in crystalline Form III.

3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) includes an XRP diffraction peak at two-theta angles of approximately 6.3, 18.3, 18.9, 19.8, and 20.4°. In another embodiment, the X-ray diffraction pattern of Form III of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) includes an XRP diffraction peak at two-theta angles of approximately 6.3, 18.3, 18.9, 19.8, or 20.4°. In some embodiments, the X-ray diffraction pattern of Form III of (S)-(2R,3R,1bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) includes an XRP diffraction peak at two-theta angles of approximately 6.3, 18.3, and 19.8°. In yet other embodiments, the X-ray diffraction pattern of Form III of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) includes an XRP diffraction peak at two-theta angles of approximately 6.3°. In certain embodiments, crystalline Form III of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) has an X-ray diffraction pattern substantially as shown in FIG. 8.

In some embodiments, crystalline Form III has one or more characteristic XRP diffraction peaks at two-theta angles of approximately 6.3°, and approximately 19.8°. In certain embodiments, crystalline Form III has one or more characteristic XRP diffraction peaks at two-theta angles of approximately 6.3°, approximately 18.3°, and approximately 19.8°. In yet other embodiments, crystalline Form III has one or more characteristic XRP diffraction peaks at two-theta angles of approximately 6.3°, approximately 18.3°, approximately 19.8°, and approximately 20.4°. In some embodiments, crystalline Form III has one or more characteristic XRP diffraction peaks at two-theta angles of approximately 6.3°, approximately 18.3°, approximately 18.9°, approximately 19.8°, and approximately 20.4°. In other embodiments, crystalline Form III has one or more characteristic XRP diffraction peaks at two-theta angles of approximately 6.3°, approximately 15.3°, approximately 18.3°, approximately 18.9°, approximately 19.8°, and approximately 20.4°. In some embodiments, crystalline Form III has one or more characteristic XRP diffraction peaks at two-theta angles of approximately 6.3°, approximately 15.3°, approximately 18.3°, approximately 18.9°, approximately 19.8°, approximately 20.4°, and approximately 24.1°.

In various embodiments, crystalline Form III has an endothermic differential scanning calorimetric (DSC) thermogram. In some embodiments, crystalline Form III has a DSC thermogram comprising an endothermic events with peak temperatures of about 93° C., 158° C., and about 230° C.

Figure 9A:
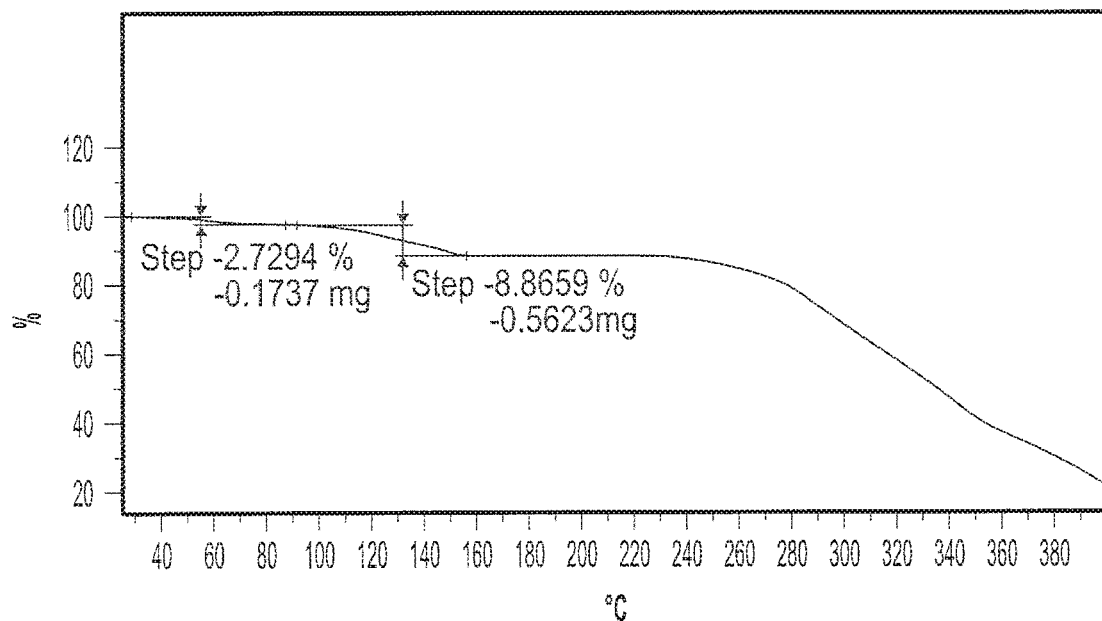
FIG. 9A depicts an exemplary Thermogravimetric Analysis (TGA) thermogram of a sample of Formula I in crystalline Form III.
Figure 9B:
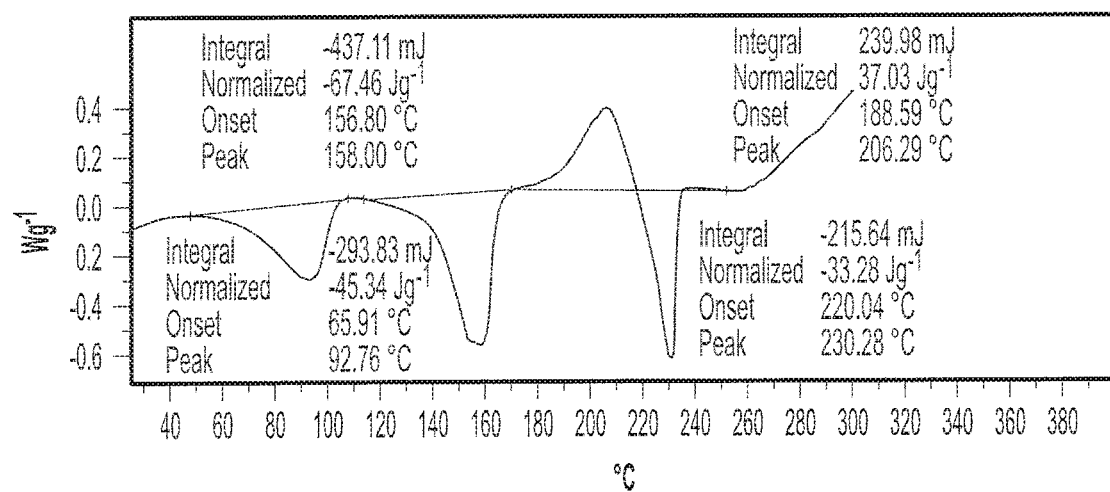
FIG. 9B depicts an exemplary Differential Scanning Calorimetry (DSC) diffractogram of a sample of Formula I in crystalline Form III.

In yet another embodiment, crystalline Form III has a DSC thermogram substantially as shown in FIG. 9. In yet another embodiment, crystalline Form III has a thermal gravimetric analysis (TGA) plot comprising two mass losses of about 2.7% and about 8.86% when heated from about 25° C. to about 140° C. In still another embodiment, crystalline Form III has a TGA plot substantially as shown in FIG. 9.

In certain embodiments Form III may be characterized by particle analysis. In certain embodiments, a sample of Form III comprises particles having birefringent lath shaped morphology. In yet another embodiment, a sample of Form III comprises particles of about 100, about 90, about 80, about 70, about 60, about 50, about 40, about 30, about 20, about 10, about 5 μM in length. In some embodiments, a sample of Form III comprises particles of about 100, about 70, about 60, about 40, about 20, about 10 μM in length.

In certain embodiments, crystalline form of Formula I in Form III may contain no less than about 95%, no less than about 97%, no less than about 98%, no less than about 99%, or no less than about 99.5% by weight of the salt of Formula I. The crystalline form may also contain no less than about 90%, no less than about 95%, no less than about 98%, no less than about 99%, or no less than about 99.5% by weight of crystal Form III.

Valbenazine Ditosylate Form IV

In another embodiment, is a crystalline form of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) or an isotopic variant thereof or solvate thereof, wherein the crystalline form is Form IV.

Figure 10:
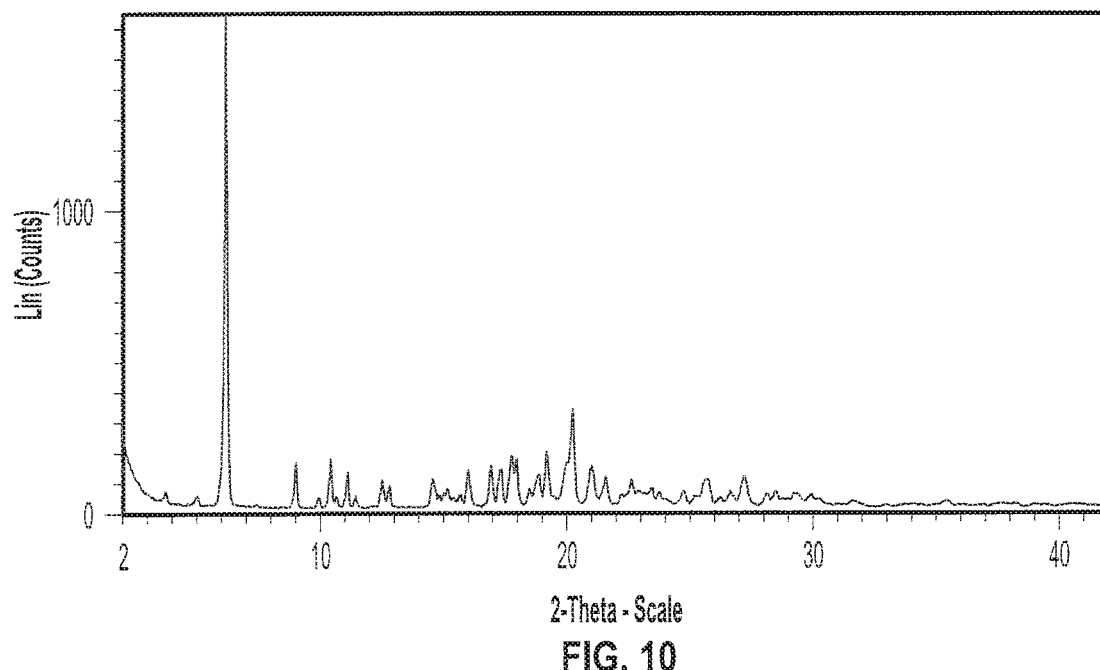
FIG. 10 depicts an exemplary X-ray powder (XRP) diffractogram of a sample of Formula I in crystalline Form IV.

In various embodiments, crystalline Form IV of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) has an X-ray diffraction pattern. In some embodiments, the X-ray diffraction pattern of Form IV of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) includes an XRP diffraction peak at two-theta angles of approximately 6.2, 10.4, 17.9, 19.2, 19.9, and 20.2°. In some embodiments, the X-ray powder diffraction pattern of Form IV of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) includes an XRP diffraction peak at two-theta angles of approximately 6.2, 10.4, 17.9, 19.2, 19.9, or 20.2°. In other embodiments, the X-ray powder diffraction pattern of Form IV of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) includes an XRP diffraction peak at two-theta angles of approximately 6.2° and approximately 20.2°. In some embodiments, the X-ray powder diffraction pattern of Form IV of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) includes an XRP diffraction peak at two-theta angles of approximately 6.2°. In certain embodiments, crystalline Form IV of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) has an X-ray diffraction pattern substantially as shown in FIG. 10.

In some embodiments, crystalline Form IV has one or more characteristic XRP diffraction peaks at two-theta angles of approximately 6.2° and approximately 20.2°. In certain embodiments, crystalline Form IV has one or more characteristic XRP diffraction peaks at two-theta angles of approximately 6.2°, approximately 10.4°, and approximately 20.2°. In other embodiments, crystalline Form IV has one or more characteristic XRP diffraction peaks at two-theta angles of approximately 6.2°, approximately 10.4°, approximately 17.9°, and approximately 20.2°. In some embodiments, crystalline Form IV has one or more characteristic XRP diffraction peaks at two-theta angles of approximately 6.2°, approximately 10.4°, approximately 17.9°, approximately 19.2°, and approximately 20.2°. In yet other embodiments, crystalline Form IV has one or more characteristic XRP diffraction peaks at two-theta angles of approximately 6.2°, approximately 10.4°, approximately 17.9°, approximately 19.2°, approximately 19.9°, and approximately 20.2°.

In various embodiments, crystalline Form IV has an endothermic differential scanning calorimetric (DSC) thermogram. In some embodiments, crystalline Form IV has a DSC thermogram comprising an endothermic events with peak temperatures of about 128° C., 159° C., and about 237° C.

Figure 11:
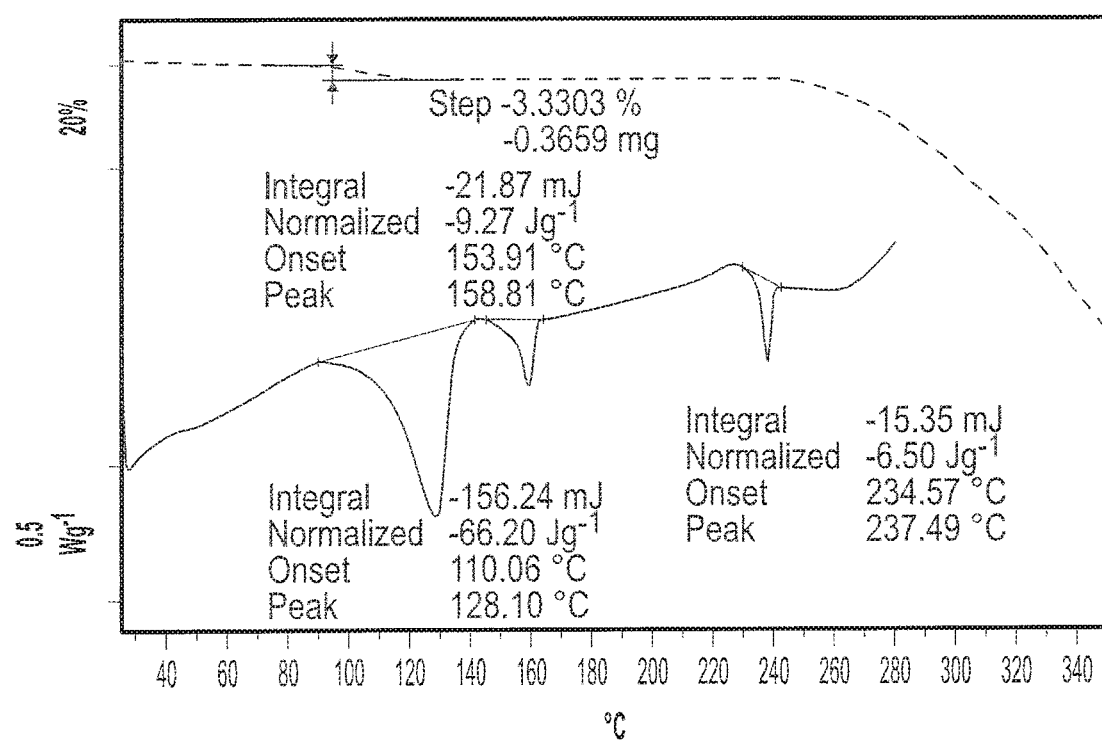
FIG. 11 depicts exemplary Thermogravimetric Analysis (TGA) thermogram (dotted line) and Differential Scanning Calorimetry (DSC) diffractogram (solid line) of a sample of Formula I in crystalline Form IV.

In yet another embodiment, crystalline Form IV has a DSC thermogram substantially as shown in FIG. 11. In yet another embodiment, crystalline Form IV has a thermal gravimetric analysis (TGA) plot comprising a mass loss of about 3.3% when heated from about 25° C. to about 140° C. In still another embodiment, crystalline Form IV has a TGA plot substantially as shown in FIG. 11.

Figure 12:
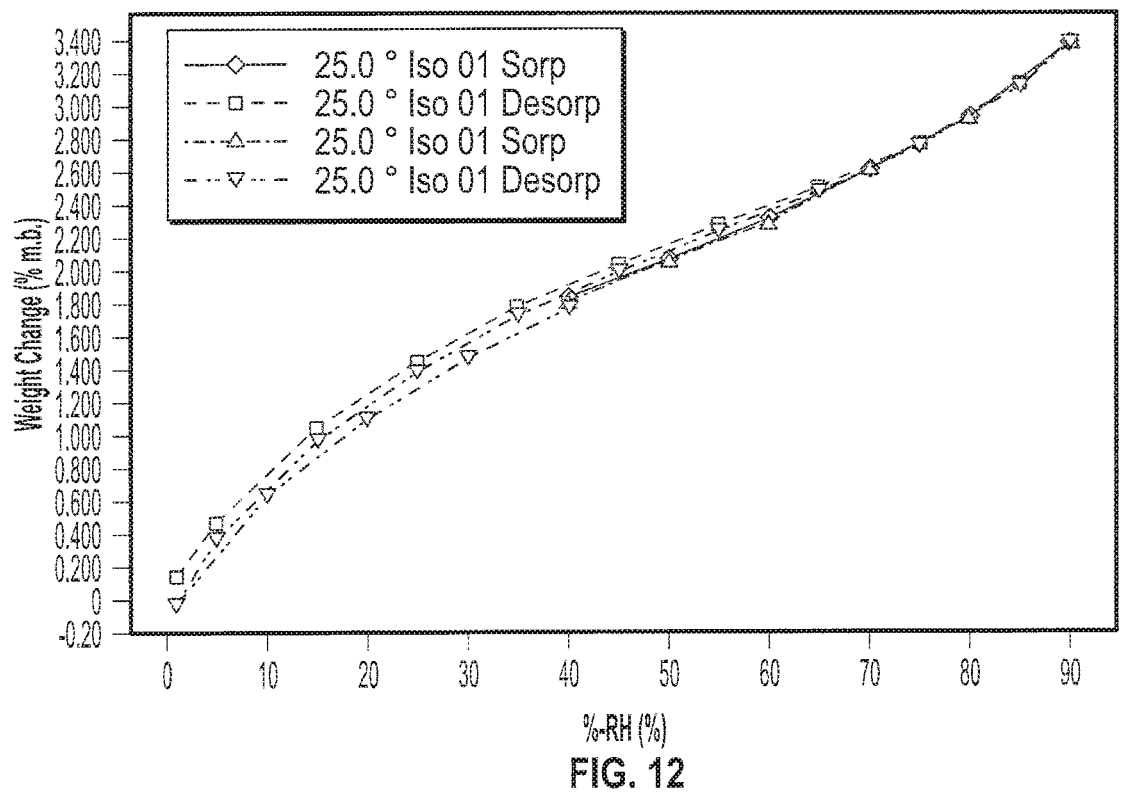
FIG. 12 depicts an exemplary Gravimetric Vapor Sorption (GVS) of a sample of Formula I in crystalline Form IV.

In various embodiments, crystalline Form IV has a gravimetric vapor system (GVS) plot. In some embodiments, crystalline Form IV exhibit a mass increase of about 3.4% when subjected to a an increase in relative humidity from about 0% to about 95% relative humidity. In some embodiments, crystalline Form IV exhibit a mass increase of about 1.6% when subjected to a an increase in relative humidity from about 40% to about 95% relative humidity. In certain embodiments, mass gained upon adsorption is lost when the relative humidity (RH) is decreased back to about 0% RH. In certain embodiments, 1.8% mass is lost when the relative humidity is decreased between about 40 and 0% RH. In yet another embodiment, crystalline Form IV exhibit a gravimetric vapour system plot substantially as shown in FIG. 12. In certain embodiments, the XRPD pattern of Form IV material is substantially unchanged following the adsorption/desorption analysis. In certain embodiments, Form IV is stable with respect to humidity. In certain embodiments, Form IV is substantially stable. In another embodiment, Form IV converts to Form I upon exposure to a solvent system comprising, e.g., mixtures of acetonitrile/water at 30° C. for about 2 days. In yet another embodiment, Form IV converts to Form I upon re-slurry of a sample of Form IV at room temperature in acetonitrile. In yet another embodiment, Form IV converts to Form I upon heating at about 230° C.

In certain embodiments Form IV may be characterized by particle analysis. In yet another embodiment, a sample of Form IV comprises particles of about 100, about 90, about 80, about 70, about 60, about 50, about 40, about 30, about 20, about 10, about 5 μM in length. In some embodiments, a sample of Form IV comprises particles of about 100, about 70, about 60, about 40, about 20, about 10 μM in length.

In certain embodiments, crystalline form of Formula I in Form IV may contain no less than about 95%, no less than about 97%, no less than about 98%, no less than about 99%, or no less than about 99.5% by weight of the salt of Formula I. The crystalline form may also contain no less than about 90%, no less than about 95%, no less than about 98%, no less than about 99%, or no less than 99.5% by weight of crystal Form IV.

Valbenazine Ditosylate Form V

In another embodiment, is a crystalline form of (S)-(2R, 3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) or an isotopic variant thereof or solvate thereof, wherein the crystalline form is Form V.

Figure 13:
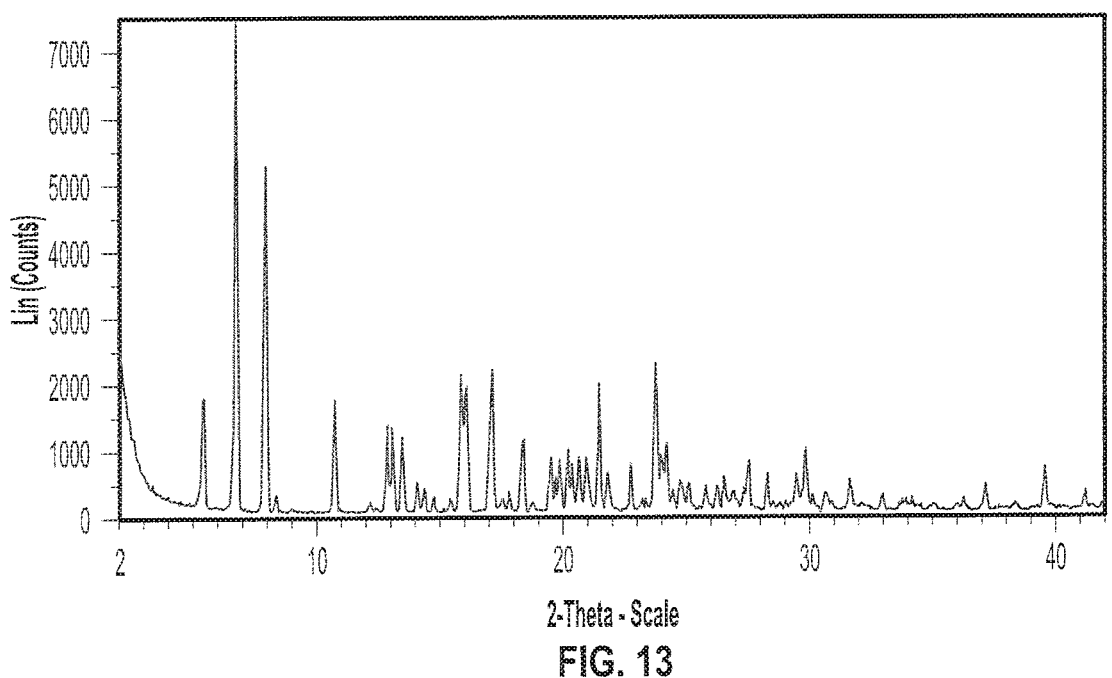
FIG. 13 depicts an exemplary X-ray powder (XRP) diffractogram of a sample of Formula I in crystalline Form V.

In various embodiments, crystalline Form V of (S)-(2R, 3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) has an X-ray diffraction pattern. In some embodiments, the X-ray diffraction pattern of Form V of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) includes an XRP diffraction peak at two-theta angles of approximately 6.7, 7.9, 10.7, 12.8, 17.1, and 23.7°. In some embodiments, the X-ray powder diffraction pattern of Form V of (S)-(2R,3R, 11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) includes an XRP diffraction peak at two-theta angles of approximately 6.7, 7.9, 10.7, 12.8, 17.1, or 23.7°. In certain embodiments, the X-ray powder diffraction pattern of Form V of (S)-(2R, 3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) includes an XRP diffraction peak at two-theta angles of approximately 6.7° and 7.9°. In some embodiments, the X-ray powder diffraction pattern of Form V of (S)-(2R,3R, 1bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) includes an XRP diffraction peak at two-theta angles of approximately 6.7°. In certain embodiments, crystalline Form V of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) has an X-ray diffraction pattern substantially as shown in FIG. 13.

In some embodiments, crystalline Form V has one or more characteristic XRP diffraction peaks at two-theta angles of approximately 6.7° and approximately 7.9°. In certain embodiments, crystalline Form V has one or more characteristic XRP diffraction peaks at two-theta angles of approximately 6.7°, approximately 7.9°, and approximately 23.7°. In some embodiments, crystalline Form V has one or more characteristic XRP diffraction peaks at two-theta angles of approximately 6.7°, approximately 7.9°, approximately 17.1°, and approximately 23.7°. In yet other embodiments, crystalline Form V has one or more characteristic XRP diffraction peaks at two-theta angles of approximately 6.7°, approximately 7.9°, approximately 15.8°, approximately 17.1°, and approximately 23.7°. In some embodiments, crystalline Form V has one or more characteristic XRP diffraction peaks at two-theta angles of approximately 6.7°, approximately 7.9°, approximately 15.8°, approximately 17.1°, approximately 21.5°, and approximately 23.7°. In certain embodiments, crystalline Form V has one or more characteristic XRP diffraction peaks at two-theta angles of approximately 6.7°, approximately 7.9°, approximately 15.8°, approximately 16.0°, approximately 17.1°, approximately 21.5°, and approximately 23.7°. In other embodiments, crystalline Form V has one or more characteristic XRP diffraction peaks at two-theta angles of approximately 6.7°, approximately 7.9°, approximately 10.7°, approximately 15.8°, approximately 16.0°, approximately 17.1°, approximately 21.5°, and approximately 23.7°. In some embodiments, crystalline Form V has one or more characteristic XRP diffraction peaks at two-theta angles of approximately 6.7°, approximately 7.9°, approximately 10.7°, approximately 12.8°, approximately 15.8°, approximately 16.0°, approximately 17.1°, approximately 21.5°, and approximately 23.7°.

In various embodiments, crystalline Form V has an endothermic differential scanning calorimetric (DSC) thermogram. In some embodiments, crystalline Form V has a DSC thermogram comprising an endothermic events with peak temperatures of about 113° C., and about 181° C.

Figure 14:
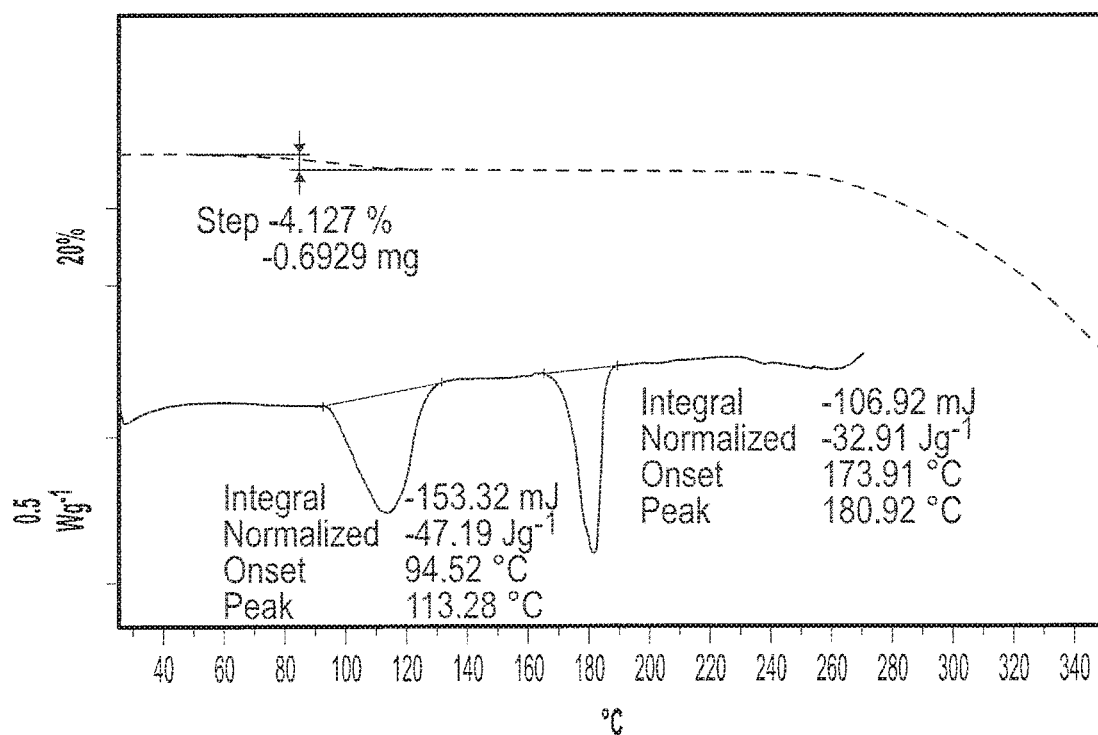
FIG. 14 depicts exemplary Thermogravimetric Analysis (TGA) thermogram (dotted line) and Differential Scanning Calorimetry (DSC) diffractogram (solid line) of a sample of Formula I in crystalline Form V.

In yet another embodiment, crystalline Form V has a DSC thermogram substantially as shown in FIG. 14. In yet another embodiment, crystalline Form V has a thermal gravimetric analysis (TGA) plot comprising a mass loss of about 4.1% when heated from about 25° C. to about 140° C. In still another embodiment, crystalline Form V has a TGA plot substantially as shown in FIG. 14.

Figure 15:
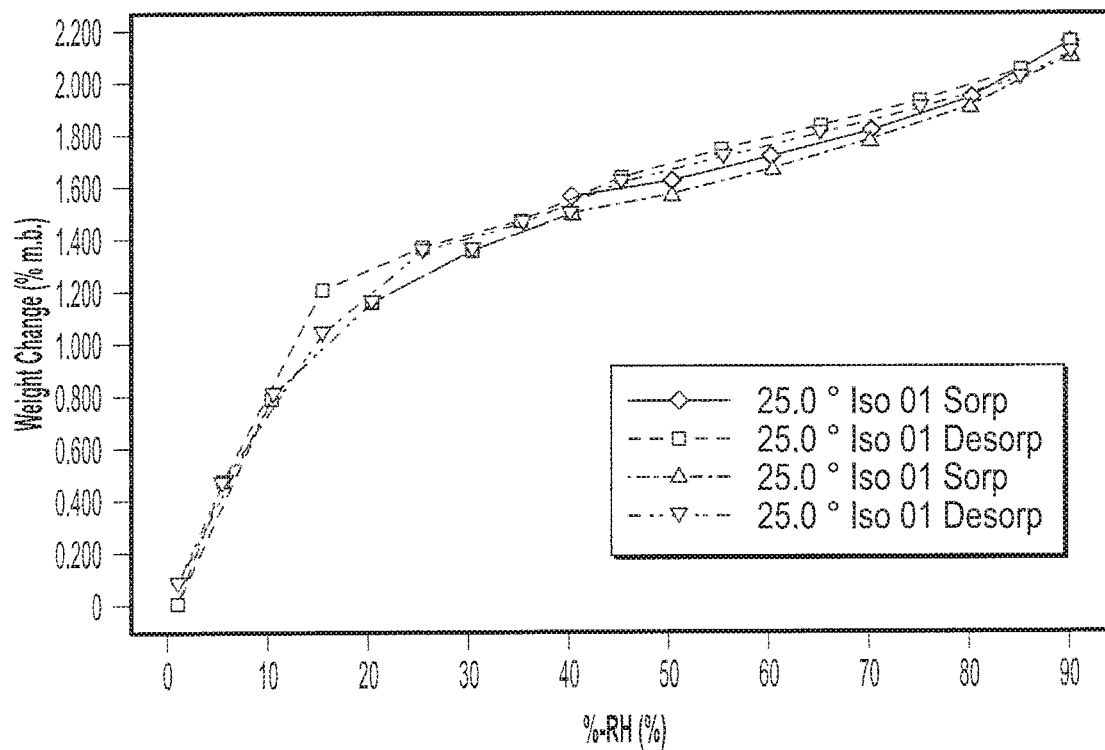
FIG. 15 depicts an exemplary Gravimetric Vapor Sorption (GVS) of a sample of Formula I in crystalline Form V.

In various embodiments, crystalline Form V has a gravimetric vapor system (GVS) plot. In some embodiments, crystalline Form V exhibit a mass increase of about 1% when subjected to a an increase in relative humidity from about 10% to about 95% relative humidity. In certain embodiments, mass gained upon adsorption is lost when the relative humidity (RH) is decreased back to about 0% RH. In certain embodiments, 1.2% mass is lost when the relative humidity is decreased between about 20 and 0% RH. In yet another embodiment, crystalline Form V exhibit a gravimetric vapor system plot substantially as shown in FIG. 15. In certain embodiments, the XRPD pattern of Form V material is substantially unchanged following the adsorption/desorption analysis. In certain embodiments, Form V is substantially stable. In another embodiment, Form V converts to Form VI upon heating between about 110° C. and about 140° C.

In certain embodiments Form V may be characterized by particle analysis. In yet another embodiment, a sample of Form V comprises particles of about 100, about 90, about 80, about 70, about 60, about 50, about 40, about 30, about 20, about 10, about 5 µM in length. In some embodiments, a sample of Form V comprises particles of about 100, about 70, about 60, about 40, about 20, about 10 µM in length.

In certain embodiments, crystalline form of Formula I in Form V may contain no less than about 95%, no less than about 97%, no less than about 98%, no less than about 99%, or no less than about 99.5% by weight of the salt of Formula I. The crystalline form may also contain no less than about 90%, no less than about 95%, no less than about 98%, no less than about 99%, or no less than about 99.5% by weight of crystal Form V.

Valbenazine Ditosylate Form VI

In another embodiment, is a crystalline form of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) or an isotopic variant thereof or solvate thereof, wherein the crystalline form is Form VI.

Figure 16:
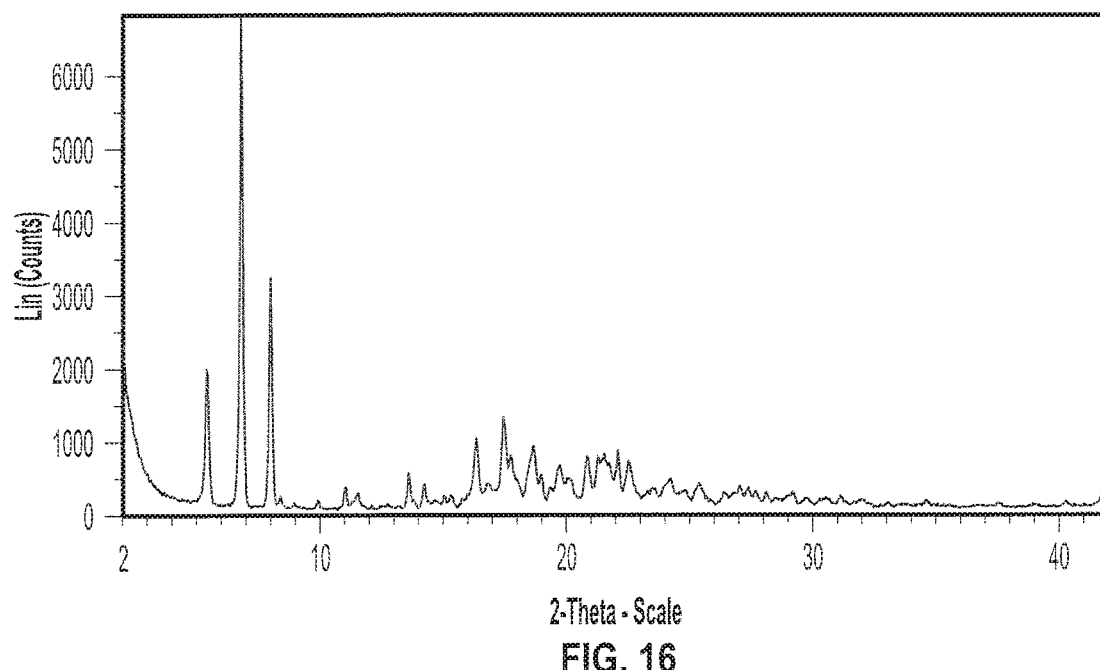
FIG. 16 depicts an exemplary X-ray powder (XRP) diffractogram of a sample of Formula I in crystalline Form VI.

In various embodiments, crystalline Form VI of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) has an X-ray diffraction pattern. In some embodiments, the X-ray diffraction pattern of Form VI of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) includes an XRP diffraction peak at two-theta angles of approximately 6.8, 8.0, 16.3, and 17.5°. In some embodiments, the X-ray powder diffraction pattern of Form VI of (S)-(2R,3R,1bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) includes an XRP diffraction peak at two-theta angles of approximately 6.8, 8.0, 16.3, or 17.5°. In certain embodiments, the X-ray powder diffraction pattern of Form VI of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) includes an XRP diffraction peak at two-theta angles of approximately 6.8° and 8.0°. In yet other embodiments, the X-ray powder diffraction pattern of Form VI of (S)-(2R,3R,1bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) includes an XRP diffraction peak at two-theta angles of approximately 6.8°. In certain embodiments, crystalline Form VI of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) has an X-ray diffraction pattern substantially as shown in FIG. 16.

In some embodiments, crystalline Form VI has one or more characteristic XRP diffraction peaks at two-theta angles of approximately 6.8° and approximately 8.0°. In certain embodiments, crystalline Form VI has one or more characteristic XRP diffraction peaks at two-theta angles of approximately 6.8°, approximately 5.4°, and approximately 8.0°. In other embodiments, crystalline Form VI has one or more characteristic XRP diffraction peaks at two-theta angles of approximately 6.8°, approximately 5.4°, and approximately 8.0°, and approximately 17.5°. In yet other embodiments, crystalline Form VI has one or more characteristic XRP diffraction peaks at two-theta angles of approximately 6.8°, approximately 5.4, and approximately 8.0°, approximately 16.3°, and approximately 17.5°. In yet other embodiments, crystalline Form VI has one or more characteristic XRP diffraction peaks at two-theta angles of approximately 6.8°, approximately 5.4°, approximately 8.0°, approximately 16.3°, approximately 17.5°, and approximately 18.7°.

In various embodiments, crystalline Form VI has an endothermic differential scanning calorimetric (DSC) thermogram. In some embodiments, crystalline Form VI has a DSC thermogram comprising an endothermic events with peak temperatures of about 175° C., and about 238° C.

Figure 17:
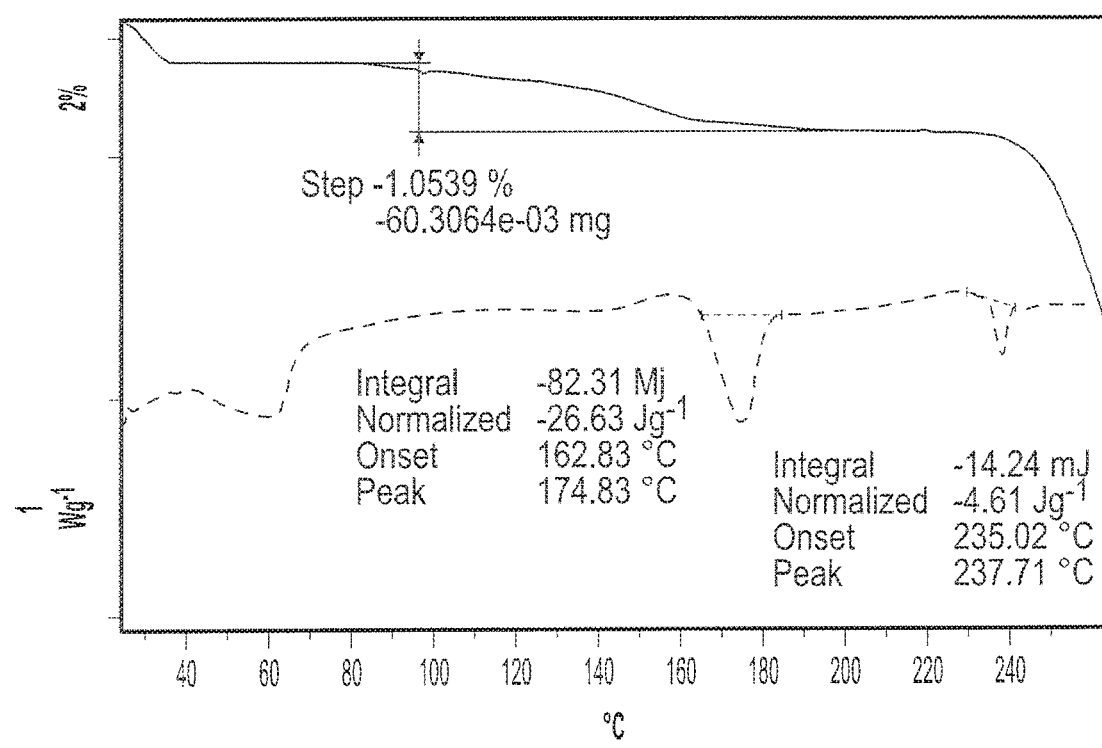
FIG. 17 depicts exemplary Thermogravimetric Analysis (TGA) thermogram (solid line) and Differential Scanning Calorimetry (DSC) diffractogram (dotted line) of a sample of Formula I in crystalline Form VI.

In yet another embodiment, crystalline Form VI has a DSC thermogram substantially as shown in FIG. 17. In yet another embodiment, crystalline Form VI has a thermal gravimetric analysis (TGA) plot comprising a mass loss of about 1% when heated from about 25° C. to about 140° C. In still another embodiment, crystalline Form V has a TGA plot substantially as shown in FIG. 17.

Figure 18:
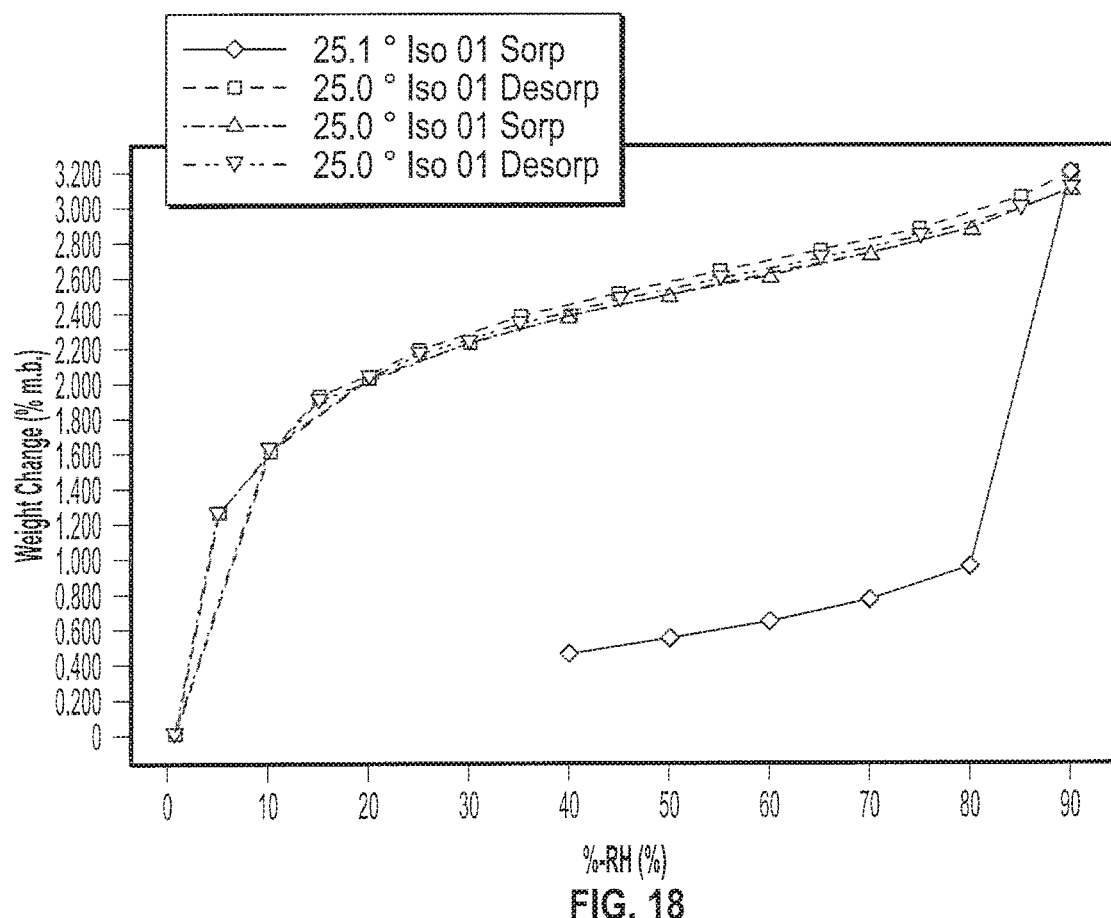
FIG. 18 depicts an exemplary Gravimetric Vapor Sorption (GVS) of a sample of Formula I in crystalline Form VI.

In various embodiments, crystalline Form VI has a gravimetric vapor system (GVS) plot. In some embodiments, crystalline Form VI exhibit a mass increase of about 3.1% when subjected to a an increase in relative humidity from about 0% to about 90% relative humidity. In some embodiments, crystalline Form VI exhibit a mass increase of about 0.5% when subjected to a an increase in relative humidity from about 40% to about 80% relative humidity. In some embodiments, crystalline Form VI exhibit a mass increase of about 3.1% when subjected to a an increase in relative humidity from about 80% to about 90% relative humidity. In certain embodiments, mass gained upon adsorption is not lost when the relative humidity (RH) is decreased back to about 0% RH. In certain embodiments, 1.2% mass is lost when the relative humidity is decreased between about 90% and 15% RH. In certain embodiments, 2.0% mass is lost when the relative humidity is decreased between about 15% and 0% RH. In yet another embodiment, crystalline Form VI exhibit a gravimetric vapor system plot substantially as shown in FIG. 18. In certain embodiments, the XRPD pattern of Form VI material is substantially changed following the adsorption/desorption analysis. In another embodiment, Form VI converts to Form V upon exposure to gravimetric vapour sorption analysis.

In certain embodiments Form VI may be characterized by particle analysis. In yet another embodiment, a sample of Form VI comprises particles of about 100, about 90, about 80, about 70, about 60, about 50, about 40, about 30, about 20, about 10, about 5 µM in length. In some embodiments, a sample of Form VI comprises particles of about 100, about 70, about 60, about 40, about 20, about 10 µM in length.

In certain embodiments, crystalline form of Formula I in Form VI may contain no less than about 95%, no less than about 97%, no less than about 98%, no less than about 99%, or no less than about 99.5% by weight of the salt of Formula I. The crystalline form may also contain no less than about 90%, no less than about 95%, no less than about 98%, no less than about 99%, or no less than 99.5% by weight of crystal Form VI.

Figure 19:
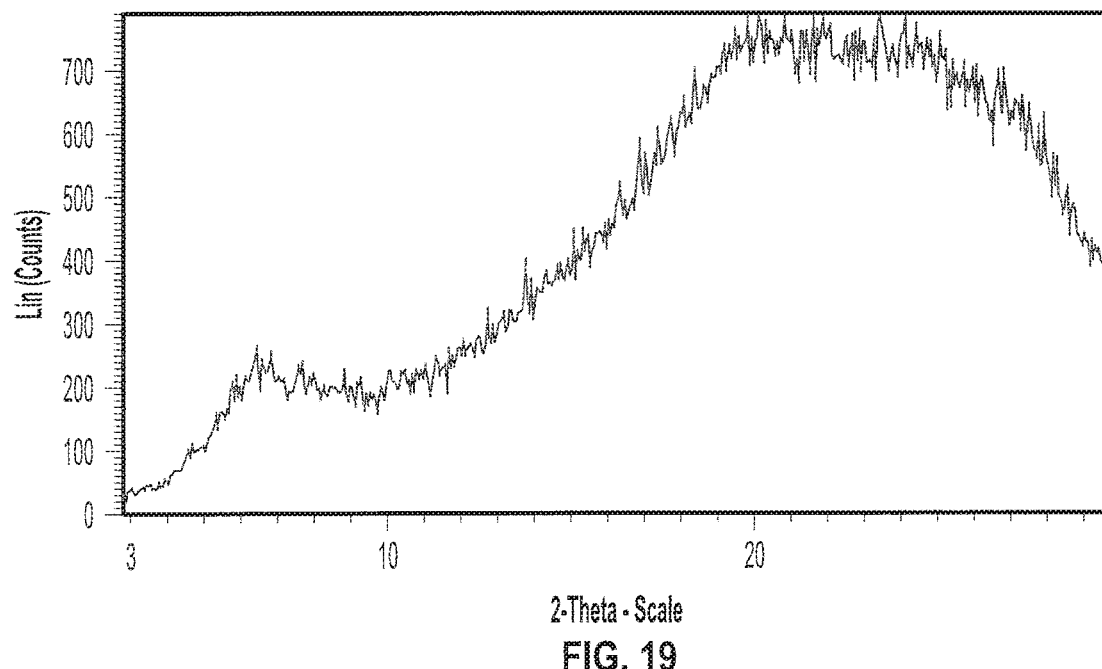
FIG. 19 depicts an exemplary X-ray powder (XRP) diffractogram of a sample of Formula I in amorphous form.

In yet another embodiment, the crystalline form of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) or an isotopic variant thereof, or solvate thereof is amorphous. The amorphous forms have an X-ray powder diffraction pattern substantially as shown in FIG. 19, which lacks the characteristic XRP diffraction peaks for the particulates of Form I and/or Form II, through Form VI. In one embodiment, the amorphous form of Formula I may contain no less than about 95%, no less than about 97%, no less than about 98%, no less than about 99%, or no less than about 99.5% by weight of the acid of Formula I. The amorphous form may also contain no less than about 90%, no less than about 95%, no less than about 98%, no less than about 99%, or no less than 99.5% by weight of amorphous form of Formula I.

Valbenazine Dihydrochloride

Provided herein is a crystalline form of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride or an isotopic variant thereof or solvate thereof of Formula II:

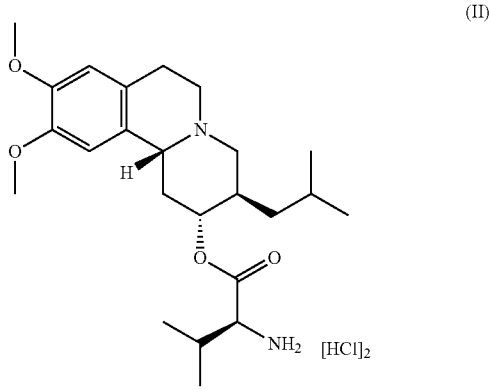

(II)

Valbenazine Dihydrochloride Form I

In another embodiment, is a crystalline form of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride (Formula II) or an isotopic variant thereof or solvate thereof, wherein the crystalline form is Form I.

Figure 20:
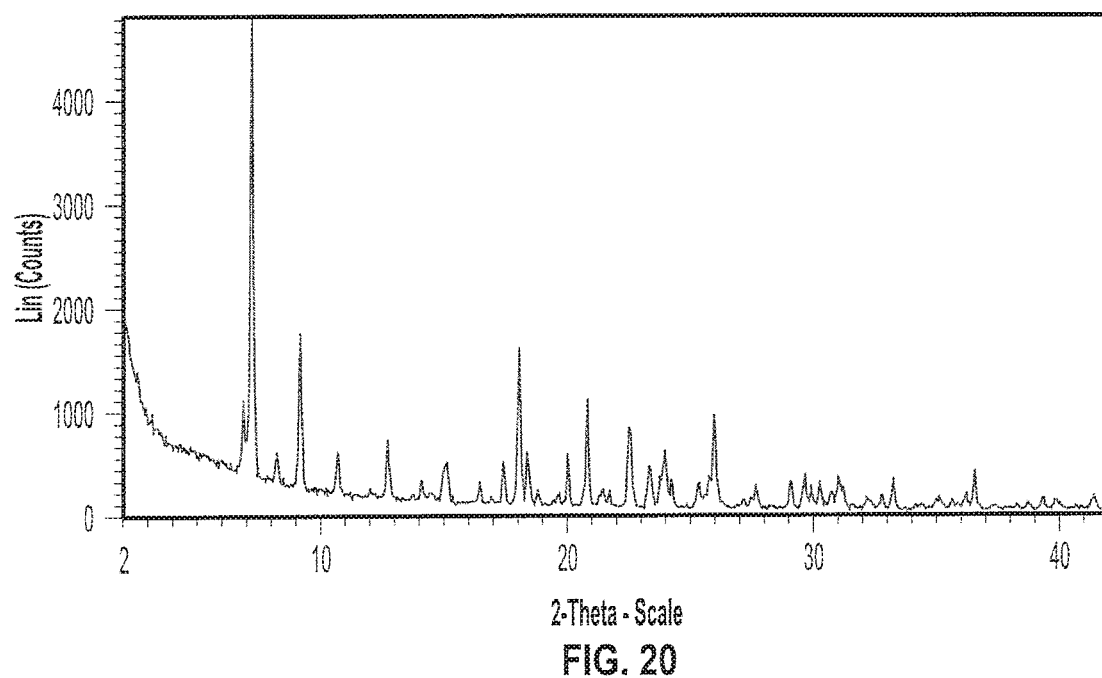
FIG. 20 depicts an exemplary X-ray powder (XRP) diffractogram of a sample of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride (Formula II) in crystalline Form I.

In various embodiments, crystalline Form I of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride (Formula II) has an X-ray diffraction pattern. In some embodiments, the X-ray diffraction pattern of Form I of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride (Formula II) includes an XRP diffraction peak at two-theta angles of approximately 7.2, 9.2, and 18.0°. In some embodiments, the X-ray powder diffraction pattern of Form I of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride (Formula II) includes an XRP diffraction peak at two-theta angles of approximately 7.2, 9.2, or 18.0°. In certain embodiments, the X-ray powder diffraction pattern of Form I of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride (Formula II) includes an XRP diffraction peak at two-theta angles of approximately 7.2 and 9.2°. In yet other embodiments, the X-ray powder diffraction pattern of Form I of (S)-(2R,3R,1bR)-3-isobutyl-9,10-dimethoxy-2,3,4,6,7,11b-hexahydro-1H-pyrido[2,1-a]isoquinolin-2-yl 2-amino-3-methylbutanoate dihydrochloride (Formula II) includes an XRP diffraction peak at two-theta angles of approximately 7.2°. In certain embodiments, crystalline Form I of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride (Formula II) has an X-ray diffraction pattern substantially as shown in FIG. 20.

In some embodiments, crystalline Form I of Formula II has one or more characteristic XRP diffraction peaks at two-theta angles of approximately 7.2° and approximately 9.2°. In certain embodiments, crystalline Form I of Formula II has one or more characteristic XRP diffraction peaks at two-theta angles of approximately 7.2°, approximately 9.2° and approximately 18.0°. In some embodiments, crystalline Form I of Formula II has one or more characteristic XRP diffraction peaks at two-theta angles of approximately 7.2°, approximately 9.2°, approximately 18.0°, and approximately 20.8°. In yet other embodiments, crystalline Form I of Formula II has one or more characteristic XRP diffraction peaks at two-theta angles of approximately 7.2°, approximately 9.2°, approximately 18.0°, approximately 20.8°, and approximately 25.9°. In certain embodiments, crystalline Form I of Formula II has one or more characteristic XRP diffraction peaks at two-theta angles of approximately 7.2°, approximately 9.2°, approximately 18.0°, approximately 20.8°, approximately 22.5°, and approximately 25.9°. In some embodiments, crystalline Form I of Formula II has one or more characteristic XRP diffraction peaks at two-theta angles of approximately 7.2°, approximately 9.2°, approximately 12.7°, approximately 18.0°, approximately 20.8°, approximately 22.5°, and approximately 25.9°. In yet other embodiments, crystalline Form I of Formula II has one or more characteristic XRP diffraction peaks at two-theta angles of approximately 7.2°, approximately 9.2°, approximately 12.7°, approximately 18.0°, approximately 20.8°, approximately 22.5°, approximately 24.0°, and approximately 25.9°.

In various embodiments, crystalline Form I of Formula II has an endothermic differential scanning calorimetric (DSC) thermogram. In some embodiments, crystalline Form I has a DSC thermogram comprising an endothermic event with onset temperature of about 240° C. and a peak at about 250° C.

Figure 21A:
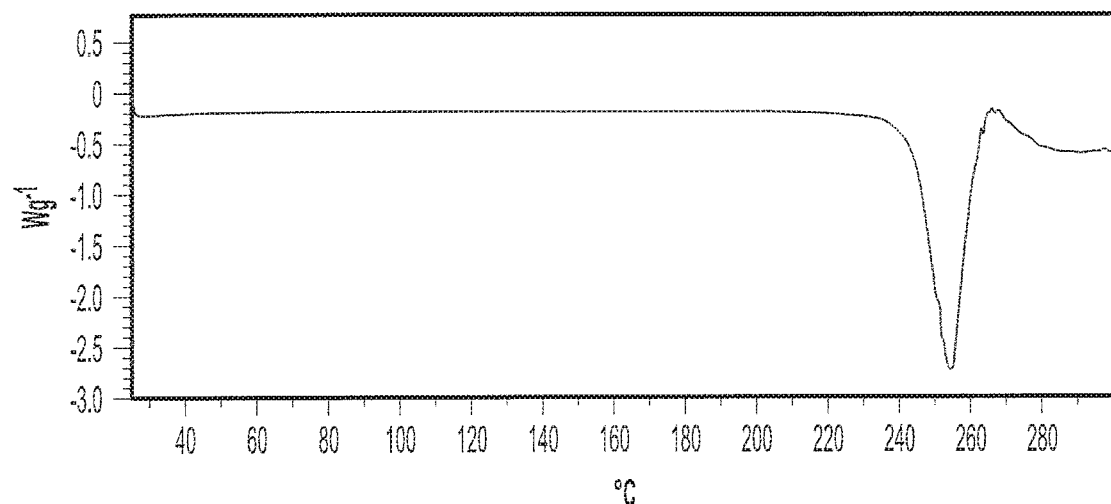
FIG. 21A depicts an exemplary Differential Scanning Calorimetry (DSC) diffractogram of a sample of Formula II in crystalline Form I.
Figure 21B:
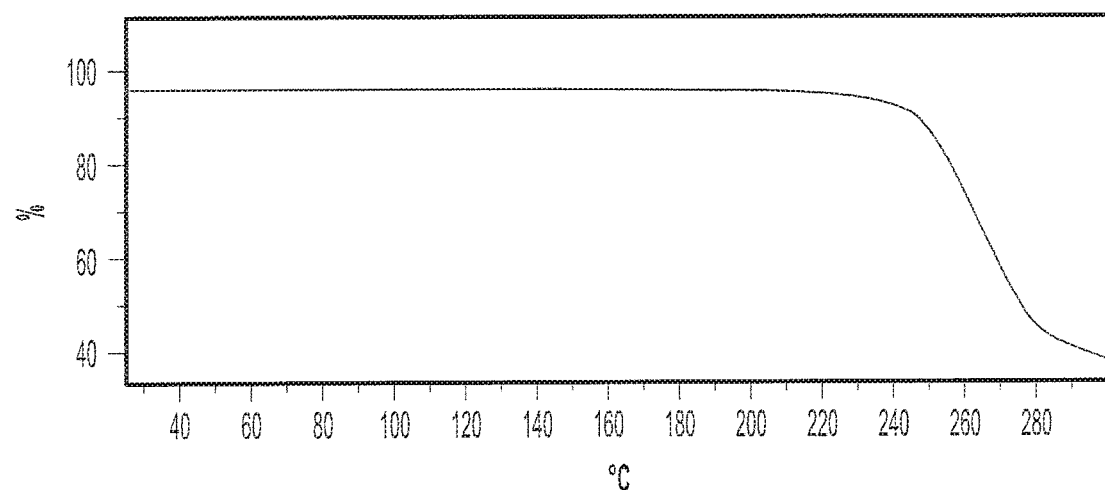
FIG. 21B depicts an exemplary Thermogravimetric Analysis (TGA) thermogram of a sample of Formula II in crystalline Form I.

In yet another embodiment, crystalline Form I of Formula II has a DSC thermogram substantially as shown in FIG. 21. In yet another embodiment, crystalline Form I of Formula II has a thermal gravimetric analysis (TGA) plot substantially as shown in FIG. 21.

Figure 22:
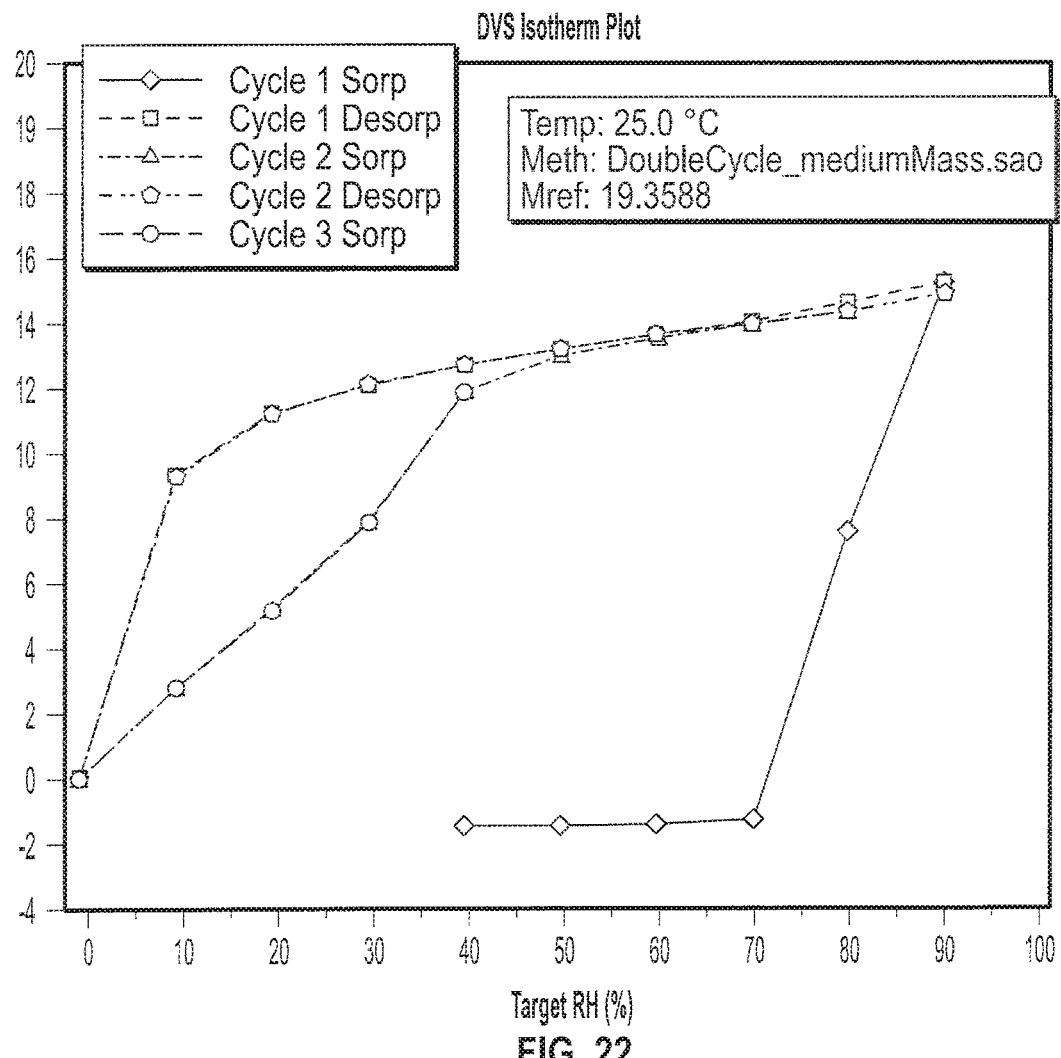
FIG. 22 depicts an exemplary Gravimetric Vapor Sorption (GVS) of a sample of Formula II in crystalline Form I.

In various embodiments, crystalline Form I of Formula II has a gravimetric vapor system (GVS) plot. In some embodiments, crystalline Form I exhibit a mass increase of about 14% when subjected to a an increase in relative humidity from about 0% to about 90% relative humidity. In yet another embodiment, crystalline Form I of Formula II exhibit a gravimetric vapour system plot substantially as shown in FIG. 22. In certain embodiments, the XRPD pattern of Form I of Formula II is substantially changed following the adsorption/desorption analysis. In another embodiment, Form I of Formula II converts to Form II upon storage at about 25° C. and about 92% relative humidity for about 7 days. In another embodiment, Form I of Formula II converts to Form II upon storage at about 40° C. and about 75% relative humidity for about 7 days. In still another embodiment, crystalline Form I of Formula II has aqueous solubility above 90 mg/mL at pH 4.1.

In certain embodiments Form I of Formula II may be characterized by particle analysis. In certain embodiments, a sample of Form II comprises particles having birefringent lath shaped morphology. In yet another embodiment, a sample of Form I of Formula II comprises particles of about 100, about 90, about 80, about 70, about 60, about 50, about 40, about 30, about 20, about 10, about 5 µM in length. In some embodiments, a sample of Form I of Formula II comprises particles of about 100, about 70, about 60, about 40, about 20, about 10 µM in length. In yet another embodiment, a sample of Form I of Formula II comprises particles of about 150 µM in length.

In certain embodiments, crystalline form of Formula II in Form I may contain no less than about 95%, no less than about 97%, no less than about 98%, no less than about 99%, or no less than about 99.5% by weight of the salt of Formula II. The crystalline form may also contain no less than about 90%, no less than about 95%, no less than about 98%, no less than about 99%, or no less than 99.5% by weight of crystal Form I.

Valbenazine Dihydrochloride Form II

In another embodiment, is a crystalline form of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride (Formula II) or an isotopic variant thereof or solvate thereof, wherein the crystalline form is Form II.

Figure 23:
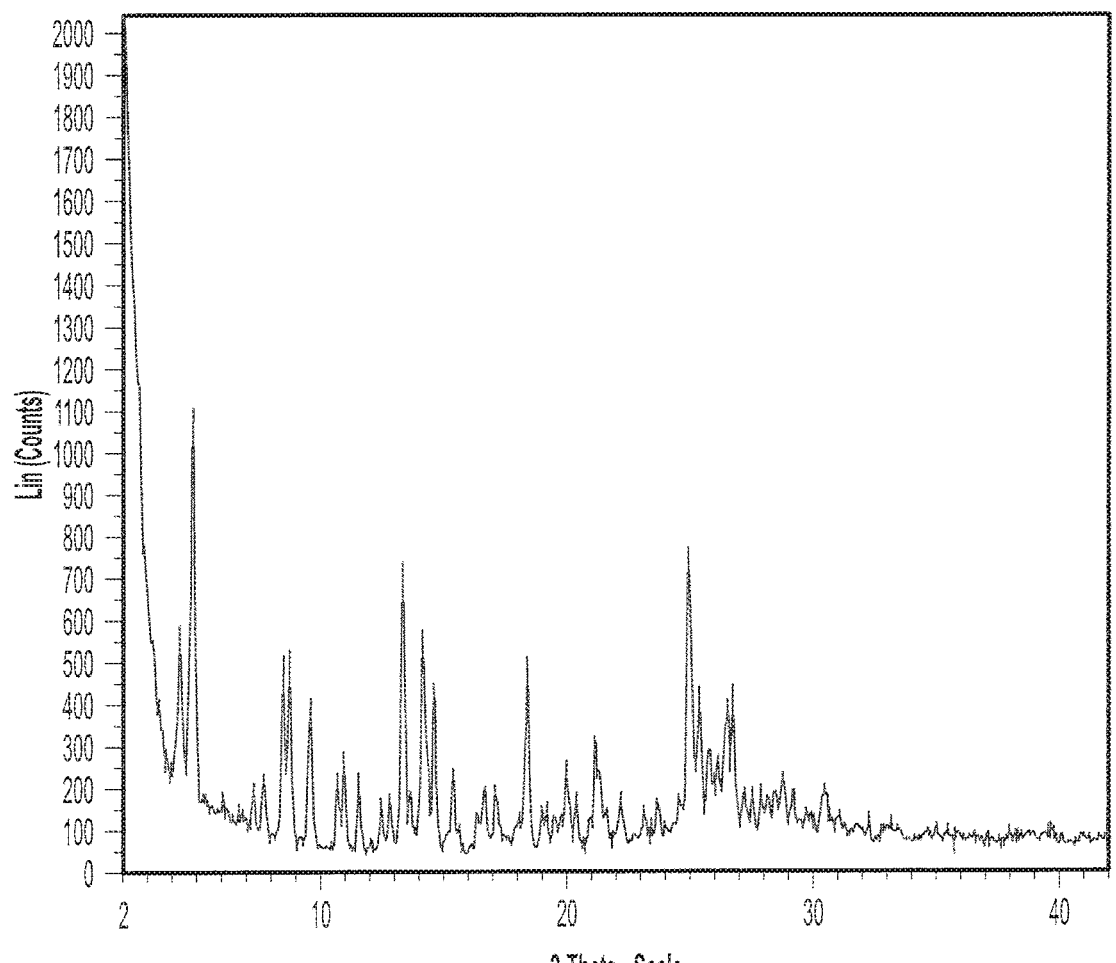
FIG. 23 depicts an exemplary X-ray powder (XRP) diffractogram of a sample of Formula II in crystalline Form II.

In various embodiments, crystalline Form II of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride (Formula II) has an X-ray diffraction pattern. In some embodiments, the X-ray diffraction pattern of Form II of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride (Formula II) includes an XRP diffraction peak at two-theta angles of approximately 4.8, 13.3, and 24.9°. In some embodiments, the X-ray powder diffraction pattern of Form II of (S)-(2R,3R,1bR)-3-isobutyl-9,10-dimethoxy-2,3,4,6,7,11b-hexahydro-1H-pyrido[2,1-a]isoquinolin-2-yl 2-amino-3-methylbutanoate dihydrochloride (Formula II) includes an XRP diffraction peak at two-theta angles of approximately 4.8, 13.3 or 24.9°. In certain embodiments, the X-ray powder diffraction pattern of Form II of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride (Formula II) includes an XRP diffraction peak at two-theta angles of approximately 4.8°. In certain embodiments, crystalline Form II of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride (Formula II) has an X-ray diffraction pattern substantially as shown in FIG. 23.

In some embodiments, crystalline Form II of Formula II has one or more characteristic XRP diffraction peaks at two-theta angles of approximately 4.8° and approximately 24.9°. In certain embodiments, crystalline Form II of Formula II has one or more characteristic XRP diffraction peaks at two-theta angles of approximately 4.8°, approximately 13.3°, and approximately 24.9°. In some embodiments, crystalline Form II of Formula II has one or more characteristic XRP diffraction peaks at two-theta angles of approximately 4.8°, approximately 13.3°, approximately 14.1°, and approximately 24.9°. In yet other embodiments, crystalline Form II of Formula II has one or more characteristic XRP diffraction peaks at two-theta angles of approximately 4.3°, approximately 4.8°, approximately 13.3°, approximately 14.1°, and approximately 24.9°. In some embodiments, crystalline Form II of Formula II has one or more characteristic XRP diffraction peaks at two-theta angles of approximately 4.3°, approximately 4.8°, approximately 13.3°, approximately 14.1°, approximately 18.4°, and approximately 24.9°. In other embodiments, crystalline Form II of Formula II has one or more characteristic XRP diffraction peaks at two-theta angles of approximately 4.3, approximately 4.8°, approximately 8.7°, approximately 13.3°, approximately 14.1°, approximately 18.4°, and approximately 24.9°. In other embodiments, crystalline Form II of Formula II has one or more characteristic XRP diffraction peaks at two-theta angles of approximately 4.3°, approximately 4.8°, approximately 8.4°, approximately 8.7°, approximately 13.3°, approximately 14.1°, approximately 18.4°, and approximately 24.9°. In yet other embodiments, crystalline Form II of Formula II has one or more characteristic XRP diffraction peaks at two-theta angles of approximately 4.3°, approximately 4.8°, approximately 8.4°, approximately 8.7°, approximately 13.3°, approximately 14.1°, approximately 14.6°, approximately 18.4°, and approximately 24.9°.

In various embodiments, crystalline Form II of Formula II has an endothermic differential scanning calorimetric (DSC) thermogram. In some embodiments, crystalline Form II has a DSC thermogram comprising an endothermic event with onset temperature of about 80° C. and a peak at about 106° C.

Figure 24A:
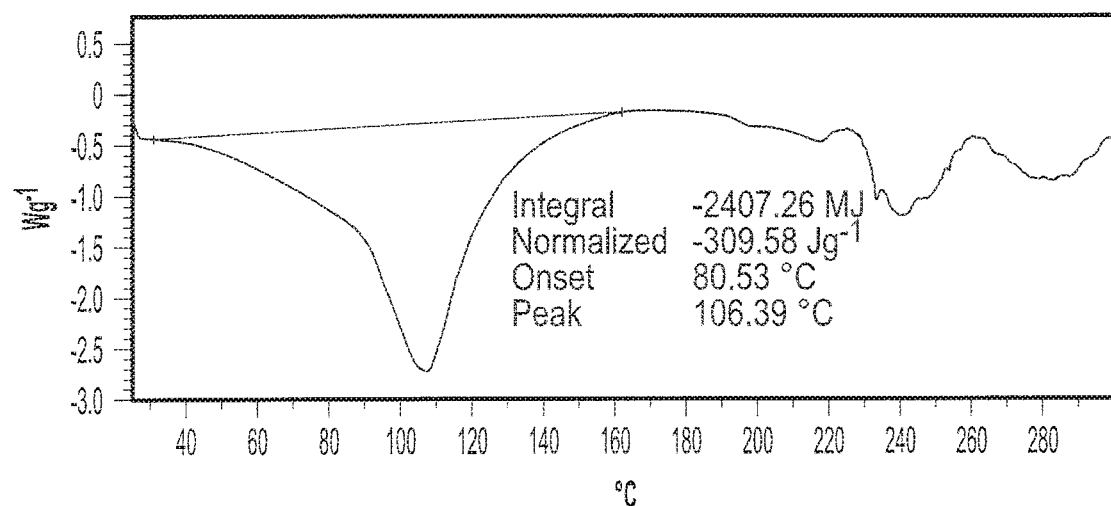
FIG. 24A depicts an exemplary Differential Scanning Calorimetry (DSC) diffractogram of a sample of Formula II in crystalline Form II.
Figure 24B:
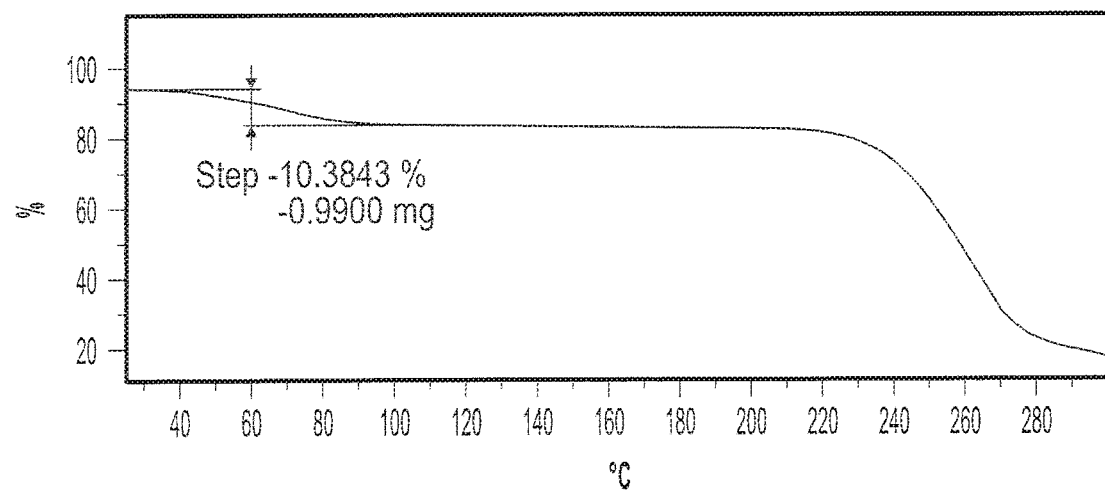
FIG. 24B depicts an exemplary Thermogravimetric Analysis (TGA) thermogram of a sample of Formula II in crystalline Form II.

In yet another embodiment, crystalline Form II of Formula II has a DSC thermogram substantially as shown in FIG. 24. In yet another embodiment, crystalline Form II of Formula II has a thermal gravimetric analysis (TGA) plot comprising a mass loss of about 10% when heated from about 25° C. to about 100° C. In still another embodiment, crystalline Form II of Formula II has a TGA plot substantially as shown in FIG. 24.

Figure 25:
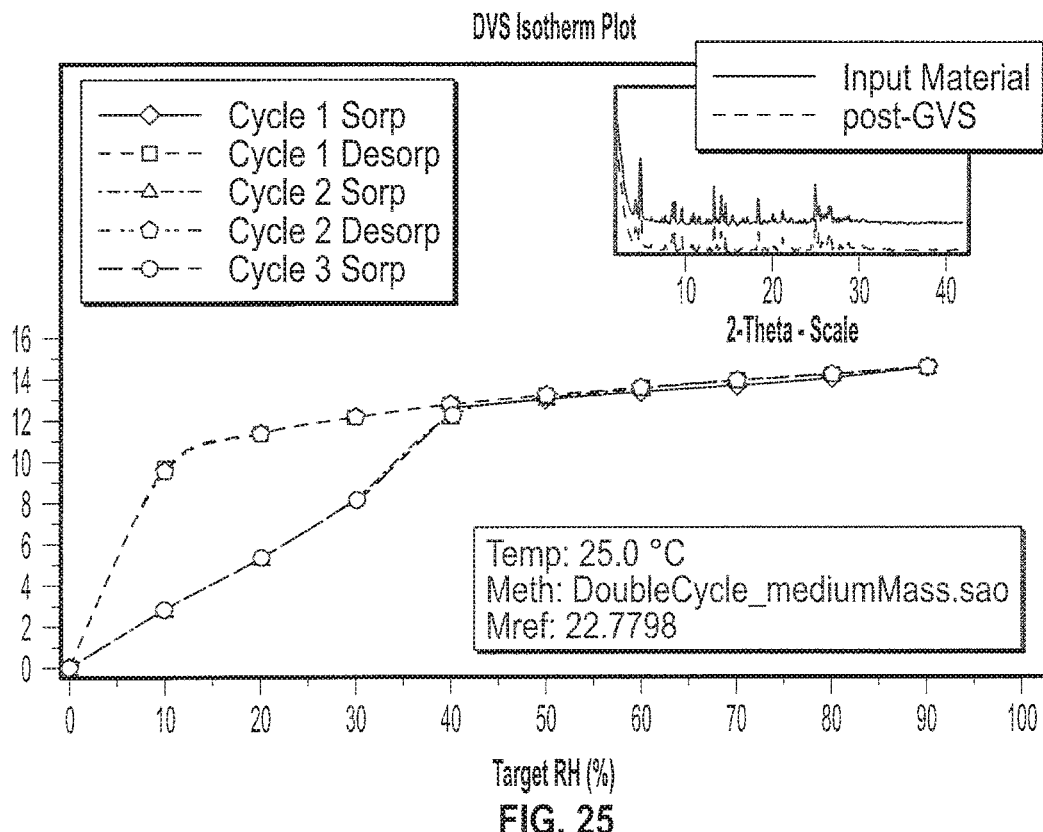
FIG. 25 depicts an exemplary Gravimetric Vapor Sorption (GVS) of a sample of Formula II in crystalline Form II.

In various embodiments, crystalline Form II of Formula II has a gravimetric vapor system (GVS) plot. In some embodiments, crystalline Form II exhibit a mass loss of about 12% when subjected to a decrease in relative humidity from about 75% to about 0% relative humidity. In yet another embodiment, crystalline Form II of Formula II exhibit a gravimetric vapour system plot substantially as shown in FIG. 25. In certain embodiments, Form II is substantially stable. In another embodiment, Form II converts to Form I upon heating. In yet another embodiment For II of Formula II converts to amorphous material upon heating at temperatures above about 160° C. In still another embodiment, crystalline Form II of Formula II has aqueous solubility above 67 mg/mL at pH 4.1.

In certain embodiments Form II of Formula II may be characterized by particle analysis. In yet another embodiment, a sample of Form II of Formula II comprises particles of about 100, about 90, about 80, about 70, about 60, about 50, about 40, about 30, about 20, about 10, about 5 µM in length. In some embodiments, a sample of Form II of Formula II comprises particles of about 100, about 70, about 60, about 40, about 20, about 10 µM in length.

In certain embodiments, crystalline form of Formula II in Form II may contain no less than about 95%, no less than about 97%, no less than about 98%, no less than about 99%, or no less than about 99.5% by weight of the salt of Formula II. The crystalline form may also contain no less than about 90%, no less than about 95%, no less than about 98%, no less than about 99%, or no less than 99.5% by weight of crystal Form II.

Figure 26:
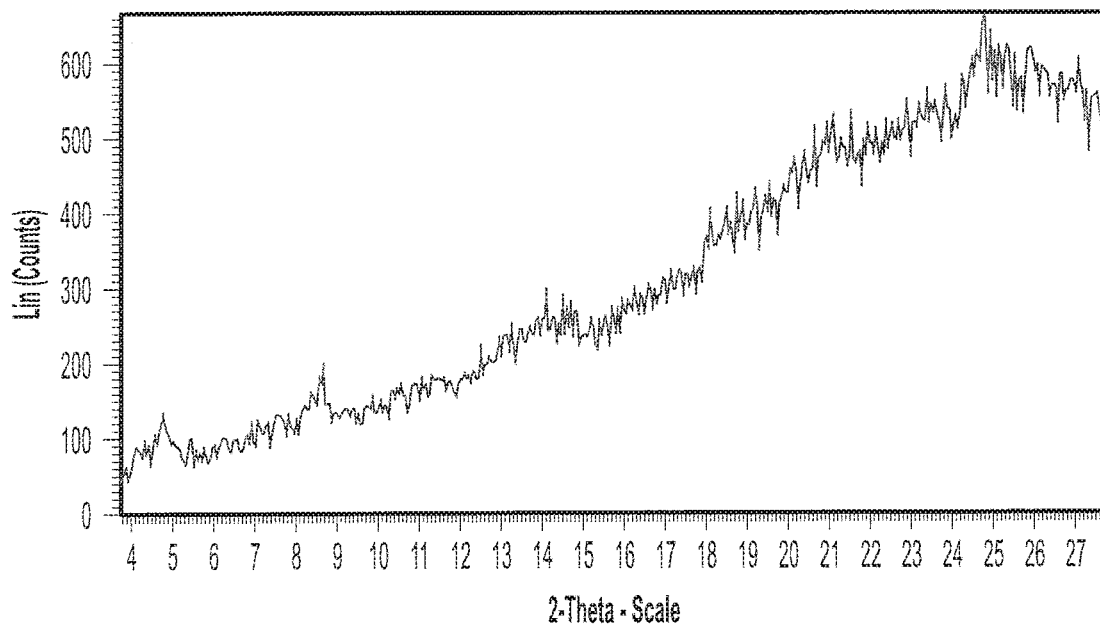
FIG. 26 depicts an exemplary X-ray powder (XRP) diffractogram of a sample of Formula II in amorphous form.

In yet another embodiment, the crystalline form of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride (Formula II) or an isotopic variant thereof, or solvate thereof is amorphous. The amorphous forms have an X-ray powder diffraction pattern substantially as shown in FIG. 26, which lacks the characteristic XRP diffraction peaks for the particulates of Form I and/or Form II of Formula II. In one embodiment, the amorphous form of Formula II may contain no less than about 95%, no less than about 97%, no less than about 98%, no less than about 99%, or no less than about 99.5% by weight of the salt of Formula II. The amorphous form may also contain no less than about 90%, no less than about 95%, no less than about 98%, no less than about 99%, or no less than 99.5% by weight of amorphous form of Formula II.

It should be understood that the numerical values of the peaks of the X-ray powder diffraction patterns may vary slightly from one machine to another or from one sample to another, and so the values quoted are not to be construed as absolute, but with an allowable variability, such as 0.2°, as defined herein.

Process of Preparation

Also provided are processes for preparing the salts of Formula I and/or Formula II in an amorphous form, or crystalline form. The processes comprise the step of contacting the salt of Formula I and/or Formula II with a solvent, in which the particulates of the salt of Formula I and/or Formula II in an amorphous form, or crystalline form (e.g., Form I, II, III, IV, V, or VI) of Formula I and/or Formula II, may be formed from a solution or converted from one solid form to another. The process may further comprise an isolation step, in which the compounds may be isolated by a conventional method, such as filtration and centrifugation, followed by washing with a solvent and then drying (e.g., vacuum oven drying, air drying, or desiccator drying).

Suitable solvents for use in preparing the compounds in an amorphous form, or crystalline form, include but are not limited to, hydrocarbons, including petroleum ether, pentane, hexane(s), heptane, octane, isooctane, cyclopentane, cyclohexane, methylcyclohexane, benzene, toluene, xylene, tetralin, and cumene; chlorinated hydrocarbons, including dichloromethane (DCM), 1,2-dichloroethane, 1, 1-dichloroethene, 1,2-dichloroethene, chloroform, trichloroethane, trichloroethene, carbon tetrachloride, chlorobenzene, and trifluoromethylbenzene; alcohols, including methanol, ethanol, isopropanol (IPA), 1-propanol, 1-butanol, 2-butanol, t-butanol, 3-methyl-1-butanol, 1-pentanol, 2-methoxyethanol, 2-ethoxyethanol, and ethyleneglycol; ethers, including diethyl ether, diisopropyl ether, methyl t-butyl ether (MTBE), diphenyl ether, 1,2-dimethoxyethane, bi(2-methoxyethyl)ether, 1,1-dimethoxymethane, 2,2-dimethoxypropane, and anisole; ketones, including acetone, butanone, methyl ethyl ketone (MEK), methyl isopropyl ketone, methyl butyl ketone, and methyl isobutyl ketone (MIBK); esters, including methyl acetate, ethyl formate, ethyl acetate, propyl acetate, isopropyl acetate, isobutyl acetate, and butyl acetate; carbonates, including ethylene carbonate and propylene carbonate; amides, including formamide, N,N-dimethylformamide (DMF), and N,N-dimethylacetamide; nitriles, including acetonitrile (ACN); sulfoxides, such as dimethyl sulfoxide (DMSO); sulfones, such sulfolane; nitro compounds, such as nitromethane and nitrobenzene; heterocycles, such as N-methyl pyrrolindone, 2-methyl tetrahydrofuran, tetrahydrofuran (THF), dioxane, and pyridine; carboxylic acids, such as acetic acid, trichloroacetic acid, and trifluoroacetic acid; phosphoramides, such as hexamethylphosphoramide; carbon sulfide; water; and mixtures thereof.

The compounds of the salt of Formula I and/or Formula II in crystalline form can be prepared from a solution or slurry of the salt of Formula I and/or Formula II in a solvent using conventional methods, including, but not limited to cooling, chilling, solvent evaporation, or addition of an anti-solvent.

In one embodiment, the process for preparing a crystalline form of the salt of Formula I and/or Formula II comprises the steps of (a) preparing a solution of the acid of Formula I and/or Formula II in a solvent at a first temperature; and (b) generating the crystalline compound at a second temperature. To accelerate the formation of the crystalline material of Formula I and/or Formula II, the process may also comprise a seeding step by seeding the solution with crystals of Form I, prior to or during step (b). The process may further comprise an isolation step as described herein.

The solution can be prepared from any forms of the salt of Formula I and/or Formula II, including, but not limited to, oil, semisolids, solids (such as an amorphous form, or Form I, II, III, IV, V, or VI of Formula I and/or Formula II), or mixtures thereof. The solution of step (a) may be prepared as a saturated or nearly saturated solution at the first temperature. The saturated or nearly saturated solution can be prepared by dissolving a sufficient amount of the salt of Formula I/and or Formula II in the solvent at a temperature that is higher than the first temperature, such that, when the solution is allowed to cool to the first temperature, a saturated or nearly saturated solution is obtained. The sufficient amount of the salt of Formula I/and or Formula II can be estimated based on the solubility of the compounds of Formula I/and or Formula II in the solvent at the first temperature, which can be determined using a method known to a person skilled in the art.

The first temperature may range from room temperature to about the boiling point of the solvent, e.g., from about 20 to about 200° C., from about 20 to about 150° C., or from about 20 to about 100° C. The second temperature may range from −100 to 100° C., from about −50 to about 50° C., from about −10 to about 30° C., 20 to about 200° C., from about 20 to about 150° C., or from about 20 to about 100° C. The first temperature may be higher or lower than, or the same as the second temperature. To maximize the yield and the efficiency of the process, the second temperature is normally set to be lower than the first temperature.

In one embodiment, the crystalline compounds of Formula I and/or Formula II are formed by heating the solvent from the solution at the second temperature. The solvent evaporation can be facilitated by applying heat and/or vacuum to the solution. In one embodiment, the solvent is acetonitrile, dichloromethane, DMF, 1,4-dioxane, methanol, 2-methoxyethanol, MIBK, acetone, 1-butanol, MTBE, DMSO, ethanol, ethyl acetate, isobutyl acetate, isopropyl acetate, 1-propanol, IPA, MEK, THF, water, or a mixture thereof.

In another embodiment, the crystalline compounds of Formula I and/or Formula II are formed by cooling the solution to the second temperature. In this case, the second temperature is set to be lower than the first temperature. In one embodiment, the solvent is acetonitrile, DMF, 1,4-dioxane, methanol, ethanol, 2-methoxyethanol, 1-butanol, 1-propanol, IPA, MIBK, MEK, THF, acetone, or a mixture thereof. In one embodiment, the solvent is acetonitrile, water, 1-propanol and mixtures thereof. In yet another embodiment, the solvent is acetonitrile, water and mixtures thereof. In another embodiment, the solvent is 1-propanol, water and mixtures thereof. In another embodiment, the solvent is 1-propanol.

In one embodiment, Form I of Formula I is formed by cooling the solution to the second temperature. In this case, the second temperature is set to be lower than the first temperature. In one embodiment, the solvent is acetonitrile/water (1% v/v), acetonitrile/water (2% v/v), acetonitrile/water (3% v/v). In one embodiment, the solvent is acetonitrile/water (3% v/v).

In yet another embodiment, the crystalline compounds of Formula I and/or Formula II are formed by adding an anti-solvent to the solution at a second temperature.

Suitable anti-solvents include, but are not limited to, hydrocarbons, including petroleum ether, pentane, hexane(s), heptane, octane, isooctane, cyclopentane, cyclohexane, methylcyclohexane, benzene, toluene, xylene, tetralin, and cumene; chlorinated hydrocarbons, including dichloromethane (DCM), 1,2-dichloroethane, 1, 1-dichloroethene, 1,2-dichloroethene, chloroform, trichloroethane, trichloroethene, carbon tetrachloride, chlorobenzene, and trifluoromethylbenzene; alcohols, including methanol, ethanol, isopropanol (IPA), 1-propanol, 1-butanol, 2-butanol, t-butanol, 3-methyl-1-butanol, 1-pentanol, 2-methoxyethanol, 2-ethoxyethanol, and ethyleneglycol; ethers, including diethyl ether, diisopropyl ether, methyl t-butyl ether (MTBE), diphenyl ether, 1,2-dimethoxyethane, bi(2-methoxyethyl)ether, 1,1-dimethoxymethane, 2,2-dimethoxypropane, and anisole; ketones, including acetone, butanone, methyl ethyl ketone (MEK), methyl isopropyl ketone, methyl butyl ketone, and methyl isobutyl ketone (MIBK); esters, including methyl acetate, ethyl formate, ethyl acetate, propyl acetate, isopropyl acetate, isobutyl acetate, and butyl acetate; carbonates, including ethylene carbonate and propylene carbonate; amides, including formamide, N,N-dimethylformamide (DMF), and N,N-dimethylacetamide; nitriles, including acetonitrile (ACN); sulfoxides, such as dimethyl sulfoxide (DMSO); sulfones, such sulfolane; nitro compounds, such as nitromethane and nitrobenzene; heterocycles, such as N-methyl pyrrolindone, 2-methyl tetrahydrofuran, tetrahydrofuran (THF), dioxane, and pyridine; carboxylic acids, such as acetic acid, trichloroacetic acid, and trifluoroacetic acid; phosphoramides, such as hexamethylphosphoramide; carbon sulfide; water; and mixtures thereof.

When two solvents are used as a solvent/anti-solvent pair, the compound of Formula I and/or Formula II has a higher solubility in the solvent than in the anti-solvent. Optionally, the solvent and the anti-solvent in a solvent/anti-solvent pair are at least partially miscible. In one embodiment, the solvent is acetonitrile, methanol, ethanol, 1-propanol, water, or a mixture thereof; and the anti-solvent is hexane(s), heptanes, diethyl ether, ethyl acetate, THF, isopropanol, and mixtures thereof. In yet another embodiment, the crystalline compounds of Formula I and/or Formula II are formed by adding the solution to an anti-solvent at the second temperature. In one embodiment, the solvent is acetonitrile, methanol, ethanol, 1-propanol, water, or a mixture thereof; and the anti-solvent is hexane(s), heptanes, diethyl ether, ethyl acetate, THF, isopropanol, and mixtures thereof.

In another embodiment, the process for preparing the crystalline compounds of Formula I and/or Formula II comprises the steps of (a) preparing a slurry of the compound of Formula I and/or Formula II in a solvent at a first temperature; and (b) generating the crystalline compounds of Formula I and/or Formula II by exposing the slurry to a second temperature. The slurry can be prepared from any forms of the compounds of Formula I and/or Formula II, including, but not limited to, oil, semisolids, solids (such as an amorphous form, or Form I, II, III, IV, V, or VI of Formula I and/or Formula II), or mixtures thereof. The process may further comprise a seeding step and/or an isolation step, as described herein.

The first and second temperatures and the solvent are as defined herein. In one embodiment, the solvent is acetonitrile, methanol, ethanol, 1-propanol, water, or a mixture thereof.

In yet another embodiment, the process for preparing the crystalline compounds of Formula I and/or Formula II comprises the steps of (a) preparing a solution of the compounds of Formula I and/or Formula II in a solvent at a first temperature; (b) forming a slurring by cooling the solution to a second temperature; and (c) generating the crystalline compounds of Formula I and/or Formula II by exposing the slurry to one or more heating and cooling cycles. The process may further comprise a seeding step and/or an isolation step, as described herein.

The first and second temperatures and the solvent are as defined herein. In one embodiment, the solvent is acetonitrile, methanol, ethanol, 1-propanol, 1,4-dioxane, water, or a mixture thereof. In one embodiment, the solvent is water. The heating and cooling cycle may be performed in a temperature range between about −50 to about 120° C., about −50 to about 100° C., about −20 to about 80° C., about 0 to about 80° C., about 10 to about 80° C., about 20 to about 80° C., about 20 to about 60° C., or about 20 to about 50° C.

In one embodiment, Form II of Formula I can be prepared from a solution or slurry of the compound of Formula I in a solvent using conventional methods, including, but not limited to, cooling, chilling, solvent evaporation, or addition of an anti-solvent.

In one embodiment, the process for preparing the Form II of Formula I comprises the steps of (a) preparing a slurry of compound of Formula I in a solvent at a first temperature; and (b) generating the crystalline Form II at a second temperature. To accelerate the formation of the particulates of Form II, the process may also comprise a seeding step by seeding the solution with crystals of Form II, prior to or during step (b). The process may further comprise an isolation step as described herein.

The solution can be prepared from any forms of the compound of Formula I, including, but not limited to, oil, semisolids, solids (such as an amorphous form, or Form I, II, III, IV, V, or VI of Formula I), or mixtures thereof. The solution of step (a) may be prepared as a saturated or nearly saturated solution at the first temperature. The saturated or nearly saturated solution may be prepared by dissolving a sufficient amount of the compound of Formula I in the solvent at a temperature that is higher than the first temperature, such that, when the solution is allowed to cool to the first temperature, a saturated or nearly saturated solution is obtained. The sufficient amount of the compound of Formula I can be estimated based on the solubility of the particulates of Form II in the solvent at the first temperature, which can be determined using a method known to a person skilled in the art. In one embodiment, the solvent is acetonitrile, water, and a mixture thereof. In one embodiment, the solvent is water.

In one embodiment, Form III of Formula I can be prepared from a solution or slurry of the compound of Formula I in a solvent using conventional methods, including, but not limited to, cooling, chilling, solvent evaporation, or addition of an anti-solvent.

In yet another embodiment, the process for preparing crystalline Form III of Formula I comprises the steps of (a) preparing a solution of the compound of Formula I in a solvent at a first temperature; (b) forming a slurring by cooling the solution to a second temperature; and (c) generating crystalline Form III of Formula I by exposing the slurry to one or more heating and cooling cycles. The process may further comprise a seeding step and/or an isolation step, as described herein.

The first and second temperatures and the solvent are as defined herein. In one embodiment, the solvent is acetonitrile, methanol, ethanol, 1-propanol, 1,4-dioxane, water, or a mixture thereof. In one embodiment, the solvent is 1,4-dioxane/water. In one embodiment, the solvent is water. The heating and cooling cycle may be performed in a temperature range between about −50 to about 120° C., about −50 to about 100° C., about −20 to about 80° C., about 0 to about 80° C., about 10 to about 80° C., about 20 to about 80° C., about 20 to about 60° C., or about 20 to about 50° C.

In one embodiment, Form IV of Formula I can be prepared from a solution or slurry of the compound of Formula I in a solvent using conventional methods, including, but not limited to, cooling, chilling, solvent evaporation, or addition of an anti-solvent.

In one embodiment, the process for preparing crystalline Form IV of Formula I comprises the steps of (a) preparing a solution of the compound of Formula I in a solvent at a first temperature; and (b) generating the crystalline compound at a second temperature. To accelerate the formation of the crystalline material of Formula I, the process may also comprise a seeding step by seeding the solution with crystals of Form IV, prior to or during step (b). The process may further comprise an isolation step as described herein.

The solution can be prepared from any forms of the salt of Formula I and/or Formula II, including, but not limited to, oil, semisolids, solids (such as an amorphous form, or Form I, II, III, IV, V, or VI of Formula I and/or Formula II), or mixtures thereof. The solution of step (a) may be prepared as a saturated or nearly saturated solution at the first temperature. The saturated or nearly saturated solution can be prepared by dissolving a sufficient amount of the salt of Formula I/and or Formula II in the solvent at a temperature that is higher than the first temperature, such that, when the solution is allowed to cool to the first temperature, a saturated or nearly saturated solution is obtained. The sufficient amount of the salt of Formula I/and or Formula II can be estimated based on the solubility of the compounds of Form I/and or Formula II in the solvent at the first temperature, which can be determined using a method known to a person skilled in the art.

The first temperature may range from room temperature to about the boiling point of the solvent, e.g., from about 20 to about 200° C., from about 20 to about 150° C., or from about 20 to about 100° C. The second temperature may range from −100 to 100° C., from about −50 to about 50° C., from about −10 to about 30° C., 20 to about 200° C., from about 20 to about 150° C., or from about 20 to about 100° C. The first temperature may be higher or lower than, or the same as the second temperature. To maximize the yield and the efficiency of the process, the second temperature is normally set to be lower than the first temperature.

In one embodiment, Form IV of Formula I is formed by cooling the solution to the second temperature. In this case, the second temperature is set to be lower than the first temperature. In one embodiment, the solvent is acetonitrile/water. In one embodiment, the solvent is acetonitrile/water (4% v/v). In one embodiment, the solvent is acetonitrile/water (10% v/v).

In one embodiment, Form V of Formula I can be prepared from a solution or slurry of the compound of Formula I in a solvent using conventional methods, including, but not limited to, cooling, chilling, solvent evaporation, or addition of an anti-solvent.

In one embodiment, the process for preparing the Form V of Formula I comprises the steps of (a) preparing a slurry of compound of Formula I in a solvent at a first temperature; and (b) generating the crystalline Form V at the first temperature. To accelerate the formation of the particulates of Form V, the process may also comprise a seeding step by seeding the solution with crystals of Form V, prior to or during step (b). The process may further comprise an isolation step as described herein.

The slurry can be prepared from any forms of the compound of Formula I, including, but not limited to, oil, semisolids, solids (such as an amorphous form, or Form I, II, III, IV, V, or VI of Formula I), or mixtures thereof. The solution of step (a) may be prepared as a saturated or nearly saturated solution at the first temperature. The saturated or nearly saturated solution may be prepared by dissolving a sufficient amount of the compound of Formula I in the solvent at a temperature that is higher than the first temperature, such that, when the solution is allowed to cool to the first temperature, a saturated or nearly saturated solution is obtained. The sufficient amount of the compound of Formula I can be estimated based on the solubility of the particulates of Form V in the solvent at the first temperature, which can be determined using a method known to a person skilled in the art. In one embodiment, the solvent is acetonitrile, water, and a mixture thereof. In one embodiment, the solvent is water.

In one embodiment, Form VI of Formula I can be prepared from a solution or slurry of the compound of Formula I in a solvent using conventional methods, including, but not limited to, cooling, chilling, solvent evaporation, or addition of an anti-solvent.

In one embodiment, the process for preparing the Form VI of Formula I comprises the steps of (a) preparing a slurry of compound of Formula I in a solvent at a first temperature; and (b) generating the crystalline Form VI at the first temperature. To accelerate the formation of the particulates of Form VI, the process may also comprise a seeding step by seeding the solution with crystals of Form VI, prior to or during step (b). The process may further comprise an isolation step as described herein.

The slurry can be prepared from any forms of the compound of Formula I, including, but not limited to, oil, semisolids, solids (such as an amorphous form, or Form I, II, III, IV, V, or VI of Formula I), or mixtures thereof. The solution of step (a) may be prepared as a saturated or nearly saturated solution at the first temperature. The saturated or nearly saturated solution may be prepared by dissolving a sufficient amount of the compound of Formula I in the solvent at a temperature that is higher than the first temperature, such that, when the solution is allowed to cool to the first temperature, a saturated or nearly saturated solution is obtained. The sufficient amount of the compound of Formula I can be estimated based on the solubility of the particulates of Form VI in the solvent at the first temperature, which can be determined using a method known to a person skilled in the art. In one embodiment, the solvent is acetonitrile, water, and a mixture thereof. In one embodiment, the solvent is water.

The amorphous compounds of Formula I and/or Formula II can be prepared from a solution or slurry of the compound of Formula I in a solvent using conventional methods, including, but not limited to, cooling, chilling, solvent evaporation, or addition of an anti-solvent.

In one embodiment, the process for preparing the amorphous compounds of Formula I and/or Formula II comprises the steps of (a) preparing a solution of the compound of Formula I and/or Formula II in a solvent at a first temperature; (b) cooling the solution to a second temperature; and (c) generating the amorphous compounds at the second temperature. The process may also comprise an isolation step as described herein.

The solution can be prepared from any forms of the compound of Formula I and/or Formula II, including, but not limited to, oil, semisolids, solids (such as an amorphous form, or Form I, II, III, IV, V, or VI), or mixtures thereof. The solution of step (a) may be prepared as a saturated or nearly saturated solution at the first temperature. The saturated or nearly saturated solution may be prepared by dissolving a sufficient amount of the compound of Formula I and/or Formula II in the solvent at a temperature that is higher than the first temperature, such that, when the solution is allowed to cool to the first temperature, a saturated or nearly saturated solution is obtained. The sufficient amount of the compound of Formula I and/or Formula II can be estimated based on the solubility of the amorphous compounds in the solvent at the first temperature, which can be determined using a method known to a person skilled in the art.

In another embodiment, the amorphous compounds are formed by cooling the solution to the second temperature. In one embodiment, the solvent is an alcohol, water, or a mixture thereof. In one embodiment, the solvent is tert-butyl alcohol, water, or a mixture thereof.

In yet another embodiment, the amorphous compounds are formed by adding the solution to an anti-solvent at a second temperature. The anti-solvents are as defined herein.

In yet another embodiment, the process for preparing the amorphous compounds of the compound of Formula I and/or Formula II comprises the steps of (a) preparing a slurry of the compound of Formula I in a solvent at a first temperature; and (b) generating the amorphous particulates through phase conversion at a second temperature. The slurry can be prepared from any forms of the compound of Formula I and/or Formula II, including, but not limited to, oil, semisolids, solids (such as an amorphous form, or Form I, II, III, IV, V, or VI), or mixtures thereof. The first and second temperatures and the solvent are as defined herein.

Other forming methods may also be applicable for preparing the compound of Formula I and/or Formula II in an amorphous form, or crystalline Form I, II, III, IV, V, or VI of Formula I and/or crystalline Form I, or II of Formula I, including spray drying, roller drying, lyophilization, and melt crystallization.

Pharmaceutical Compositions

Also provided herein is a pharmaceutical composition comprising (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) in a an amorphous form, or crystalline Form I, II, III, IV, V, or VI, or a acceptable hydrate or solvate thereof, as an active pharmaceutical ingredient, in combination with one or more pharmaceutically acceptable carriers or excipients.

Also provided herein is a pharmaceutical composition comprising of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride (Formula II) in a an amorphous form, or crystalline Form I, or II, or a acceptable hydrate or solvate thereof, as an active pharmaceutical ingredient, in combination with one or more pharmaceutically acceptable carriers or excipients.

The choice of excipient, to a large extent, depends on factors, such as the particular mode of administration, the effect of the excipient on the solubility and stability of the active ingredient, and the nature of the dosage form.

The pharmaceutical compositions provided herein may be provided in unit dosage forms or multiple-dosage forms. Unit-dosage forms, as used herein, refer to physically discrete units suitable for administration to human and animal subjects and packaged individually as is known in the art. Each unit-dose contains a predetermined quantity of the active ingredient(s) sufficient to produce the desired therapeutic effect, in association with the required pharmaceutical carriers or excipients. Examples of unit-dosage forms include ampouls, syringes, and individually packaged tablets and capsules. Unit dosage forms may be administered in fractions or multiples thereof. A multiple-dosage form is a plurality of identical unit-dosage forms packaged in a single container to be administered in segregated unit-dosage form. Examples of multiple-dosage forms include vials, bottles of tablets or capsules, or bottles of pints or gallons.

The particulates of the compounds of Formula I and/or Formula II provided herein may be administered alone, or in combination with one or more other compounds provided herein, one or more other active ingredients. The pharmaceutical compositions provided herein may be formulated in various dosage forms for oral, parenteral, and topical administration. The pharmaceutical compositions may also be formulated as a modified release dosage form, including delayed-, extended-, prolonged-, sustained-, pulsatile-, controlled-, accelerated- and fast-, targeted-, programmed-release, and gastric retention dosage forms. These dosage forms can be prepared according to conventional methods and techniques known to those skilled in the art (see, Remington: *The Science and Practice of Pharmacy*, supra; *Modified-Release Drug Delivery Technology*, Rathbone et al., Eds., Drugs and the Pharmaceutical Science, Marcel Dekker, Inc.: New York, N.Y., 2002; Vol. 126).

The pharmaceutical compositions provided herein may be administered at once, or multiple times at intervals of time.

It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

Oral Administration

The pharmaceutical compositions provided herein may be provided in solid, semisolid, or liquid dosage forms for oral administration. As used herein, oral administration also include buccal, lingual, and sublingual administration. Suitable oral dosage forms include, but are not limited to, tablets, capsules, pills, troches, lozenges, pastilles, cachets, pellets, medicated chewing gum, granules, bulk powders, effervescent or non-effervescent powders or granules, solutions, emulsions, suspensions, solutions, wafers, sprinkles, elixirs, and syrups. In addition to the active ingredient(s), the pharmaceutical compositions may contain one or more pharmaceutically acceptable carriers or excipients, including, but not limited to, binders, fillers, diluents, disintegrants, wetting agents, lubricants, glidants, coloring agents, dye-migration inhibitors, sweetening agents, and flavoring agents.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, Panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pregelatinized starch, and mixtures thereof. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets.

Suitable disintegrants include, but are not limited to, agar; bentonite; celluloses, such as methylcellulose and carboxymethylcellulose; wood products; natural sponge; cation-exchange resins; alginic acid; gums, such as guar gum and Vee gum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL ® 200 (W.R. Grace Co., Baltimore, Md.) and CAB-O-SIL ® (Cabot Co. of Boston, Mass.); and mixtures thereof. The pharmaceutical compositions provided herein may contain about 0.1 to about 5% by weight of a lubricant.

Suitable glidants include colloidal silicon dioxide, CAB-O-SIL ® (Cabot Co. of Boston, Mass.), and asbestos-free talc. Coloring agents include any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Flavoring agents include natural flavors extracted from plants, such as fruits, and synthetic blends of compounds which produce a pleasant taste sensation, such as peppermint and methyl salicylate. Sweetening agents include sucrose, lactose, mannitol, syrups, glycerin, and artificial sweeteners, such as saccharin and aspartame. Suitable emulsifying agents include gelatin, acacia, tragacanth, bentonite, and surfactants, such as polyoxyethylene sorbitan monooleate (TWEEN® 20), polyoxyethylene sorbitan monooleate 80 (TWEEN®80), and triethanolamine oleate. Suspending and dispersing agents include sodium carboxymethylcellulose, pectin, tragacanth, Veegum, acacia, sodium carbomethylcellulose, hydroxypropyl methylcellulose, and polyvinylpyrolidone. Preservatives include glycerin, methyl and propylparaben, benzoic add, sodium benzoate and alcohol. Wetting agents include propylene glycol monostearate, sorbitan monooleate, diethylene glycol monolaurate, and polyoxyethylene lauryl ether. Solvents include glycerin, sorbitol, ethyl alcohol, and syrup. Examples of non-aqueous liquids utilized in emulsions include mineral oil and cottonseed oil. Organic acids include citric and tartaric acid. Sources of carbon dioxide include sodium bicarbonate and sodium carbonate.

It should be understood that many carriers and excipients may serve several functions, even within the same formulation. The pharmaceutical compositions provided herein may be provided as compressed tablets, tablet triturates, chewable lozenges, rapidly dissolving tablets, multiple compressed tablets, or enteric-coating tablets, sugar-coated, or film-coated tablets. Enteric coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenylsalicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein may be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein may be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquids or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde (the term "lower" means an alkyl having between 1 and 6 carbon atoms), e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or polyalkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations may further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration may be also provided in the forms of liposomes, micelles, microspheres, or nanosystems. Micellar dosage forms can be prepared as described in U.S. Pat. No. 6,350,458.

The pharmaceutical compositions provided herein may be provided as noneffervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms. The pharmaceutical compositions provided herein may be formulated as immediate or modified release dosage forms, including delayed-, sustained, pulsed-, controlled, targeted-, and programmed-release forms.

The pharmaceutical compositions provided herein may be co-formulated with other active ingredients which do not impair the desired therapeutic action, or with substances that supplement the desired action, such as antacids, proton pump inhibitors, and $H_2$-receptor antagonists.

The pharmaceutical compositions provided herein may be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, and subcutaneous administration.

Parenteral Administration

The pharmaceutical compositions provided herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, Remington: *The Science and Practice of Pharmacy*, supra).

The pharmaceutical compositions intended for parenteral administration may include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, dimethylacetamide, and dimethylsulfoxide.

Suitable antimicrobial agents or preservatives include, but are not limited to, phenols, cresols, mercurials, benzyl alcohol, chlorobutanol, methyl and propyl phydroxybenzates, thimerosal, benzalkonium chloride, benzethonium chloride, methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents include those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including alpha-cyclodextrin, beta-cyclodextrin, hydroxypropyl-beta-cyclodextrin, sulfobutylether-beta-cyclodextrin, and sulfobutylether 7-beta-cyclodextrin (CAPTISOL®, CyDex, Lenexa, Kans.).

The pharmaceutical compositions provided herein may be formulated for single or multiple dosage administration. The single dosage formulations are packaged in an ampule, a vial, or a syringe. The multiple dosage parenteral formulations must contain an antimicrobial agent at bacteriostatic or fungistatic concentrations. All parenteral formulations must be sterile, as known and practiced in the art.

In one embodiment, the pharmaceutical compositions are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein may be formulated as immediate or modified release dosage forms, including delayed-, sustained, pulsed-, controlled, targeted-, and programmed-release forms.

The pharmaceutical compositions may be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers, such as hydrogels of esters of acrylic and methacrylic acid, collagen, cross-linked polyvinylalcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

Topical Administration

The pharmaceutical compositions provided herein may be administered topically to the skin, orifices, or mucosa. The topical administration, as used herein, include (intra)dermal, conjuctival, intracorneal, intraocular, ophthalmic, auricular, transdermal, nasal, vaginal, uretheral, respiratory, and rectal administration.

The pharmaceutical compositions provided herein may be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, dermal patches. The topical formulation of the pharmaceutical compositions provided herein may also comprise liposomes, micelles, microspheres, nanosystems, and mixtures thereof.

Pharmaceutically acceptable carriers and excipients suitable for use in the topical formulations provided herein include, but are not limited to, aqueous vehicles, water miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryopretectants, lyoprotectants, thickening agents, and inert gases.

The pharmaceutical compositions may also be administered topically by electroporation, iontophoresis, phonophoresis, sonophoresis and microneedle or needle-free injection, such as POWDERJECT™ (Chiron Corp., Emeryville, Calif.), and BIOJECT™ (Bioject Medical Technologies Inc., Tualatin, Oreg.).

The pharmaceutical compositions provided herein may be provided in the forms of ointments, creams, and gels. Suitable ointment vehicles include oleaginous or hydrocarbon bases, including such as lard, benzoinated lard, olive oil, cottonseed oil, and other oils, white petrolatum; emulsifiable or absorption bases, such as hydrophilic petrolatum, hydroxystearin sulfate, and anhydrous lanolin; water-removable bases, such as hydrophilic ointment; water-soluble ointment bases, including polyethylene glycols of varying molecular weight; emulsion bases, either water-in-oil (W/O) emulsions or oil-in-water (O/W) emulsions, including cetyl alcohol, glyceryl monostearate, lanolin, and stearic acid (see, Remington: *The Science and Practice of Pharmacy*, supra).

These vehicles are emollient but generally require addition of antioxidants and preservatives.

Suitable cream base can be oil-in-water or water-in-oil. Cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include crosslinked acrylic acid polymers, such as carbomers, carboxypolyalkylenes, Carbopol®; hydrophilic polymers, such as polyethylene oxides, polyoxyethylene-polyoxypropylene copolymers, and polyvinyl-alcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical compositions provided herein may be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in Remington: *The Science and Practice of Pharmacy*, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (*theobroma* oil), glycerin-gelatin, carbowax (polyoxyethylene glycol), spermaceti, paraffin, white and yellow wax, and appropriate mixtures of mono-, di- and triglycerides of fatty acids, hydrogels, such as polyvinyl alcohol, hydroxyethyl methacrylate, polyacrylic acid; glycerinated gelatin. Combinations of the various vehicles may be used. Rectal and vaginal suppositories may be prepared by the compressed method or molding. The typical weight of a rectal and vaginal suppository is about 2 to 3 g.

The pharmaceutical compositions provided herein may be administered ophthalmically in the forms of solutions, suspensions, ointments, emulsions, gel-forming solutions, powders for solutions, gels, ocular inserts, and implants.

The pharmaceutical compositions provided herein may be administered intranasally or by inhalation to the respiratory tract. The pharmaceutical compositions may be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions may also be provided as a dry powder for insufflation, alone or in combination with an inert carrier such as lactose or phospholipids; and nasal drops. For intranasal use, the powder may comprise a bioadhesive agent, including chitosan or cyclodextrin.

Solutions or suspensions for use in a pressurized container, pump, spray, atomizer, or nebulizer may be formulated to contain ethanol, aqueous ethanol, or a suitable alternative agent for dispersing, solubilizing, or extending release of the active ingredient provided herein, a propellant as solvent; and/or a surfactant, such as sorbitan trioleate, oleic acid, or an oligolactic acid.

The pharmaceutical compositions provided herein may be micronized to a size suitable for delivery by inhalation, such as 50 micrometers or less, or 10 micrometers or less. Particles of such sizes may be prepared using a comminuting method known to those skilled in the art, such as spiral jet milling, fluid bed jet milling, supercritical fluid processing to form nanoparticles, high pressure homogenization, or spray drying.

Capsules, blisters and cartridges for use in an inhaler or insufflator may be formulated to contain a powder mix of the pharmaceutical compositions provided herein; a suitable powder base, such as lactose or starch; and a performance modifier, such as l-leucine, mannitol, or magnesium stearate. The lactose may be anhydrous or in the form of the monohydrate. Other suitable excipients include dextran, glucose, maltose, sorbitol, xylitol, fructose, sucrose, and trehalose. The pharmaceutical compositions provided herein for inhaled/intranasal administration may further comprise a suitable flavor, such as menthol and levomenthol, or sweeteners, such as saccharin or saccharin sodium.

The pharmaceutical compositions provided herein for topical administration may be formulated to be immediate release or modified release, including delayed-, sustained-, pulsed-, controlled-, targeted, and programmed release.

Modified Release

The pharmaceutical compositions provided herein may be formulated as a modified release dosage form. As used herein, the term "modified release" refers to a dosage form in which the rate or place of release of the active ingredient(s) is different from that of an immediate dosage form when administered by the same route. Modified release dosage forms include delayed-, extended-, prolonged-, sustained-, pulsatile- or pulsed-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500.

Matrix Controlled Release Devices

The pharmaceutical compositions provided herein in a modified release dosage form may be fabricated using a matrix controlled release device known to those skilled in the art (see, Takada et al. in "*Encyclopedia of Controlled Drug Delivery*," Vol. 2, Mathiowitz ed., Wiley, 1999).

In one embodiment, the pharmaceutical compositions provided herein in a modified release dosage form is formulated using an erodible matrix device, which is water swellable, erodible, or soluble polymers, including synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; and cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethylhydroxy ethylcellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acidglycolic acid copolymers; poly-D-(-)-3-hydroxybutyric acid; and other acrylic acid derivatives, such as homopolymers and copolymers of butylmethacrylate, methylmethacrylate, ethylmethacrylate, ethylacrylate, (2-dimethylaminoethyl)methacrylate, and (trimethylaminoethyl)methacrylate chloride.

In another embodiment, the pharmaceutical compositions are formulated with a non-erodible matrix device. The active ingredient(s) is dissolved or dispersed in an inert matrix and is released primarily by diffusion through the inert matrix once administered. Materials suitable for use as a non-erodible matrix device included, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinylacetate copolymers, ethylene/propylene copolymers, ethylene/ethyl acrylate copolymers, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, polyvinyl chloride, plasticized nylon, plasticized polyethyleneterephthalate, natural rubber, silicone rubbers, polydimethylsiloxanes, silicone carbonate copolymers, and; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients in the compositions.

The pharmaceutical compositions provided herein in a modified release dosage form may be prepared by methods known to those skilled in the art, including direct compression, dry or wet granulation followed by compression, melt-granulation followed by compression.

Osmotic Controlled Release Devices

The pharmaceutical compositions provided herein in a modified release dosage form may be fabricated using an osmotic controlled release device, including one-chamber system, two-chamber system, asymmetric membrane technology (AMT), and extruding core system (ECS). In general, such devices have at least two components: (a) the core which contains the active ingredient(s); and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents waterswellable hydrophilic polymers, which are also referred to as "osmopolymers" and "hydrogels," including, but not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-tolunesulfonic acid, succinic acid, and tartaric acid; urea; and mixtures thereof.

Osmotic agents of different dissolution rates may be employed to influence how rapidly the active ingredient(s) is initially delivered from the dosage form. For example, amorphous sugars, such as Mannogeme EZ (SPI Pharma, Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core may also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxlated ethylene-vinylacetate, EC, PEG, PPG, PEG/PPG copolymers, PVP, HEC, HPC, CMC, CMEC, HPMC, HPMCP, HPMCAS, HPMCAT, poly(acrylic) acids and esters and poly(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane may also be a hydrophobic microporous membrane, wherein the pores are substantially filled with a gas and are not wetted by the aqueous medium but are permeable to water, as disclosed in U.S. Pat. No. 5,798,119. Such hydrophobic but water-permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane may be formed postcoating by mechanical or laser drilling. Delivery port(s) may also be formed in situ by erosion of a plug of water-soluble material or by rupture of a thinner portion of the membrane over an indentation in the core. In addition, delivery ports may be formed during coating process, as in the case of asymmetric membrane coatings of the type disclosed in U.S. Pat. Nos. 5,612,059 and 5,698,220.

The total amount of the active ingredient(s) released and the release rate can substantially by modulated via the thickness and porosity of the semipermeable membrane, the composition of the core, and the number, size, and position of the delivery ports.

The pharmaceutical compositions in an osmotic controlled-release dosage form may further comprise additional conventional excipients as described herein to promote performance or processing of the formulation.

The osmotic controlled-release dosage forms can be prepared according to conventional methods and techniques known to those skilled in the art (see, Remington: *The Science and Practice of Pharmacy*, supra; Santus and Baker, *J. Controlled Release* 1995, 35, 1-21; Verma et al., *Drug Development and Industrial Pharmacy* 2000,26, 695-708; Verma et al., *J. Controlled Release* 2002, 79, 7-27).

In certain embodiments, the pharmaceutical compositions provided herein are formulated as AMT controlled-release dosage form, which comprises an asymmetric osmotic membrane that coats a core comprising the active ingredient(s) and other pharmaceutically acceptable excipients. See, U.S. Pat. No. 5,612,059 and WO 2002/17918. The AMT controlled-release dosage forms can be prepared according to conventional methods and techniques known to those skilled in the art, including direct compression, dry granulation, wet granulation, and a dip-coating method.

In certain embodiment, the pharmaceutical compositions provided herein are formulated as ESC controlled-release dosage form, which comprises an osmotic membrane that coats a core comprising the active ingredient(s), hydroxylethyl cellulose, and other pharmaceutically acceptable excipients.

Multiparticulate Controlled Release Devices

The pharmaceutical compositions provided herein in a modified release dosage form may be fabricated a multiparticulate controlled release device, which comprises a multiplicity of particles, granules, or pellets, ranging from about 10 μm to about 3 mm, about 50 μm to about 2.5 mm, or from about 100 μm to 1 mm in diameter. Such multiparticulates may be made by the processes know to those skilled in the art, including wet- and dry-granulation, extrusion/spheronization, roller-compaction, melt-congealing, and by spray-coating seed cores. See, for example, *Multiparticulate Oral Drug Delivery*; Marcel Dekker: 1994; and *Pharmaceutical Pelletization Technology*; Marcel Dekker: 1989.

Other excipients as described herein may be blended with the pharmaceutical compositions to aid in processing and forming the multiparticulates. The resulting particles may themselves constitute the multiparticulate device or may be coated by various film forming materials, such as enteric polymers, water-swellable, and water-soluble polymers. The multiparticulates can be further processed as a capsule or a tablet.

Targeted Delivery

The pharmaceutical compositions provided herein may also be formulated to be targeted to a particular tissue, receptor, or other area of the body of the subject to be treated, including liposome-, resealed erythrocyte-, and antibody-based delivery systems. Examples include, but are not limited to, U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542; and 5,709,874.

Method of Use

In one embodiment, provided herein is a method for the treatment, prevention, or amelioration of one or more symptoms associated with inhibition of human vesicular monoamine transporter isoform 2 (VMAT2), comprising administering to a subject a therapeutically effective amount of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) in an amorphous form, or crystalline Form I, IL, III, IV, V, or VI; or an isotopic variant thereof, or solvate thereof.

In another embodiment, provided herein is a method for the treatment, prevention, or amelioration of one or more symptoms of hyperkinetic disorders, comprising administering to a subject a therapeutically effective amount of (S)-(2R,3R,1bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I)

in an amorphous form, or crystalline Form I, IL, III, IV, V, or VI; or an isotopic variant thereof; or solvate thereof.

In one embodiment, provided herein is a method for the treatment, prevention, or amelioration of one or more symptoms associated with inhibition of human vesicular monoamine transporter isoform 2 (VMAT2), comprising administering to a subject a therapeutically effective amount of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride (Formula II) in an amorphous form, or crystalline Form I, or II; or an isotopic variant thereof, or solvate thereof.

In another embodiment, provided herein is a method for the treatment, prevention, or amelioration of one or more symptoms of hyperkinetic disorders, comprising administering to a subject a therapeutically effective amount of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride (Formula II) in an amorphous form, or crystalline Form I, or II; or an isotopic variant thereof; or solvate thereof.

In one embodiment, conditions which may be treated by compounds described herein include, but are not limited to, hyperkinetic disorders such as Huntington's disease, tardive dyskinesia, Tourette syndrome, dystonia, hemiballismus, chorea, senile chorea, or tics. In some embodiments, conditions which may be treated by compounds described herein include, but are not limited to tardive dyskinesia in subjects with schizophrenia, schizoaffective disorder or mood disorder. In one embodiment, conditions which may be treated by compounds described herein include, but are not limited to neurological disorders or diseases such as bipolar disorder, major depressive disorder, anxiety, attention-deficit hyperactivity disorder, dementia, depression, insomnia, psychosis, post-traumatic stress disorder, substance abuse, Parkinson's disease levodopa-induced dyskinesia, movement disorders, or oppositional defiant disorder.

Movement disorders include, but are not limited to, ataxia, corticobasal degeneration, dyskinesias (paroxysmal), dystonia (general, segmental, focal) including blepharospasm, spasmodic torticollis (cervical dystonia), writer's cramp (limb dystonia), laryngeal dystonia (spasmodic dysphonia), and oromandibular dystonia, essential tremor, hereditary spastic paraplegia, Huntington's disease, multiple system atrophy (Shy Drager Syndrome), myoclonus, Parkinson's Disease, progressive supranuclear palsy, restless legs syndrome, Rett Syndrome, spasticity due to stroke, cerebral palsy, multiple sclerosis, spinal cord or brain injury, Sydenham's Chorea, tardive dyskinesia/dystonia, tics, Tourette's Syndrome, and Wilson's Disease.

Depending on the disease to be treated and the subject's condition, the compositions provided herein may be administered by oral, parenteral (e.g., intramuscular, intraperitoneal, intravenous, ICV, intracisternal injection or infusion, subcutaneous injection, or implant), inhalation, nasal, vaginal, rectal, sublingual, or topical (e.g., transdermal or local) routes of administration and may be formulated, alone or together, in suitable dosage unit with pharmaceutically acceptable carriers, adjuvants and vehicles appropriate for each route of administration. Also provided is administration of the particulates provided herein in a depot formulation, in which the active ingredient is released over a predefined time period.

In the treatment, prevention, or amelioration of one or more symptoms of hyperkinetic disorder or other conditions, disorders or diseases associated with VMAT2 inhibition, an appropriate dosage level generally is about 0.001 to 100 mg per kg patient body weight per day (mg/kg per day), about 0.01 to about 80 mg/kg per day, about 0.1 to about 50 mg/kg per day, about 0.5 to about 25 mg/kg per day, or about 1 to about 20 mg/kg per day, which may be administered in single or multiple doses. Within this range the dosage may be 0.005 to 0.05, 0.05 to 0.5, or 0.5 to 5.0, 1 to 15, 1 to 20, or 1 to 50 mg/kg per day. In certain embodiments, the dosage level is about 0.001 to 100 mg/kg per day. In certain embodiments, the dosage level is about 0.01 to about 40 mg/kg per day. In certain embodiments, the dosage level is about 0.1 to about 80 mg/kg per day. In certain embodiments, the dosage level is about 0.1 to about 50 mg/kg per day. In certain embodiments, the dosage level is about 0.1 to about 40 mg/kg per day. In certain embodiments, the dosage level is about 0.5 to about 80 mg/kg per day. In certain embodiments, the dosage level is about 0.5 to about 40 mg/kg per day. In certain embodiments, the dosage level is about 0.5 to about 25 mg/kg per day. In certain embodiments, the dosage level is about 1 to about 80 mg/kg per day. In certain embodiments, the dosage level is about 1 to about 40 mg/kg per day. In certain embodiments, the dosage level is about 1 to about 25 mg/kg per day.

For oral administration, the pharmaceutical compositions can be provided in the form of tablets containing 1.0 to 1,000 mg of the active ingredient, particularly about 1, about 5, about 10, about 15, about 20, about 25, about 30, about 40, about 45, about 50, about 75, about 80, about 100, about 150, about 200, about 250, about 300, about 400, about 500, about 600, about 750, about 800, about 900, and about 1,000 mg of the active ingredient for the symptomatic adjustment of the dosage to the patient to be treated. In certain embodiments, the pharmaceutical compositions can be provided in the form of tablets containing about 100 mg of the active ingredient. In certain embodiments, the pharmaceutical compositions can be provided in the form of tablets containing about 80 mg of the active ingredient. In certain embodiments, the pharmaceutical compositions can be provided in the form of tablets containing about 50 mg of the active ingredient. In certain embodiments, the pharmaceutical compositions can be provided in the form of tablets containing about 40 mg of the active ingredient. In certain embodiments, the pharmaceutical compositions can be provided in the form of tablets containing about 25 mg of the active ingredient. The compositions may be administered on a regimen of 1 to 4 times per day, including once, twice, three times, and four times per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Also provided herein are methods of modulating VMAT2 activity, comprising contacting the transporter with the compounds in one or more solid forms as provided herein. In one embodiment, the transporter is expressed by a cell.

The compounds provided herein may also be combined or used in combination with other agents useful in the treatment, prevention, or amelioration of one or more symptoms of the diseases or conditions for which the compounds provided herein are useful, including Huntington's disease, tardive dyskinesia, Tourette's syndrome or tics noted above. In one embodiment, the compounds provided herein may also be combined or used in combination with other agents useful in the treatment, prevention, or amelioration of one or more symptoms of the diseases or conditions associated with schizophrenia, schizoaffective disorder, bipolar disease, major depressive disorder and other conditions commonly treated with antipsychotic medication.

Such other agents, or drugs, may be administered, by a route and in an amount commonly used thereof, simultaneously or sequentially with the compounds provided herein. When an the particulates provided herein are used contemporaneously with one or more other drugs, a pharmaceutical composition containing such other drugs in addition to the compounds provided herein may be utilized, but is not required. Accordingly, the pharmaceutical compositions provided herein include those that also contain one or more other active ingredients or therapeutic agents, in addition to the compounds provided herein.

The weight ratio of the compounds provided herein to the second active ingredient may be varied, and will depend upon the effective dose of each ingredient. Generally, an effective dose of each will be used. Thus, for example, when the compounds provided herein are used in combination with the second drug, or a pharmaceutical composition containing such other drug, the weight ratio of the particulates to the second drug may range from about 1,000:1 to about 1:1,000, or about 200:1 to about 1:200. Combinations of the particulates provided herein and other active ingredients will generally also be within the aforementioned range, but in each case, an effective dose of each active ingredient should be used.

EXAMPLES

The crystalline compounds of Formula I and/or Formula II in the following examples were characterized with X-ray powder diffractometry (XRPD), differential scanning calorimetry (DSC), thermogravimetry (TGA), gravimetric vapour sorption (GVS), scanning electron microscopy (SEM), and Ion Chromatography (IC).

X-Ray Powder Diffraction patterns were collected on a Bruker AXS C2 GADDS diffractometer using Cu Kα radiation (40 kV, 40 mA), θ-2θ goniometer, and divergence of V4 and receiving slits, a Ge monochromator and a Lynxeye detector. Samples were run at room temperature as flat plate specimens using powdered material. The sample was gently packed into a cavity cut into polished, zero-background (510) silicon wafer. The sample was rotated in its own plane during analysis. The data were collected from 2 to 42 degrees two-theta at 0.05 degrees two-theta per step and 0.5 seconds per step.

Differential scanning calorimetry was carried out using a Mettler DSC 823E equipped with a 34 position auto-sampler. Typically 0.5-3 mg of each sample, in a pin-holed aluminium pan, was heated at 10° C./min from 25° C. up to 250° C. A nitrogen purge at 50 ml/min was maintained over the sample.

The thermogravimetric analysis was carried out on a Mettler TGA/SDTA 851e equipped with a 34 position auto-sampler. The instrument was temperature calibrated using certified indium. Typically 5-30 mg of each sample was loaded onto a pre-weighed aluminum crucible and was heated at 10° C./min from ambient temperature to 350° C. A nitrogen purge at 50 ml/min was maintained over the sample.

The Gravimetric sorption isotherms were obtained using a Hiden IGASorp moisture sorption analyser, controlled by CFRSorp software. The sample temperature was maintained at 25° C. by a Huber re-circulating water bath. The humidity was controlled by mixing streams of dry and wet nitrogen, with a total flow rate of 250 ml/min. The relative humidity (RH) was measured by a calibrated Vaisala RH probe (dynamic range of 0-95% RH), located near the sample. The weight change, (mass relaxation) of the sample as a function of % RH was constantly monitored by the microbalance (accuracy ±0.001 mg). Typically 10-20 mg of sample was placed in a tared mesh stainless steel basket at room temperature. The sample was loaded and unloaded at 40% RH and 25° C. (typical room conditions). The standard isotherm was performed at 25° C. at 10% RH intervals over a 0-90% RH range.

Scanning Electron Micrographs (SEM) were produced by coating the desired material with a thin layer of gold (sputter coating) and examining it using a FEI-Philips XL30 scanning electron microscope. The acceleration voltage of the electrons used for the analysis was 2.0 KV. All images were captured with a computer controlled CCD camera attachment.

Ion Chromatography (IC) was performed on a Metrohm 861 Advanced Compact IC sing IC Net software v2.3. Accurately weighed samples were prepared as stock solutions in an appropriate dissolving solution and diluted appropriately prior to testing. Quantification was achieved by comparison with standard solutions of known concentration of the ion being analyzed.

The water content of each sample was performed by Karl Fisher Titration measured on a Mettler Toledo DL39 Coulometer using Hydranal Coulomat AG reagent and an argon purge. Weighed solid samples were introduced into the vessel on a platinum TGA pan which was connected to a subaseal to avoid water ingress. Approx 10 mg of sample was used per titration and duplicate determinations were made.

Thermodynamic Aqueous solubility was determined by suspending sufficient compound in water to give a maximum final concentration of ≥10 mg/ml of the parent free-form of the compound. The suspension was equilibrated at 25° C. for 24 hours then the pH was measured. The suspension was then filtered through a glass fibre C filter. The filtrate was then diluted by an appropriate factor e.g. 101. Quantitation was done by HPLC with reference to a standard solution of approximately 0.25 mg/ml in DMSO. Different volumes of the standard, diluted and undiluted sample solutions were injected. The solubility was calculated using the peak areas determined by integration of the peak found at the same retention time as the principal peak in the standard injection.

Example 1

Determination of solubility of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate)

Solubility studies of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) in the solvents listed in Table 1 were carried out from Form I, at both 5° C. and 10° C. above the reflux temperature of each solvent. Form I was slurried for at least 2 hours before filtration. The solubility was calculated by gravimetric analysis after evaporation of the mother liquors collected.

Example 2

Preparation of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate), Form I 537 mg of (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester free base was weighed into a glass vial and dissolved in 5 mL MIBK. 2.56 mL (2.0 eq) of a 1M solution of p-toluenesulfonic acid in ethanol was then added, giving a clear solution. This solution was seeded with ca. 2 mg of bistosylate salt isolated from the screen, inducing immediate crystallization. The resulting suspension was incubated for 16 h, cycling between ambient and 50° C. at 4 h intervals. After this time, the solid present was isolated by filtration and dried under vacuum for 3 h, giving 675 mg (69%) of fine white solid.

Figure 4A:
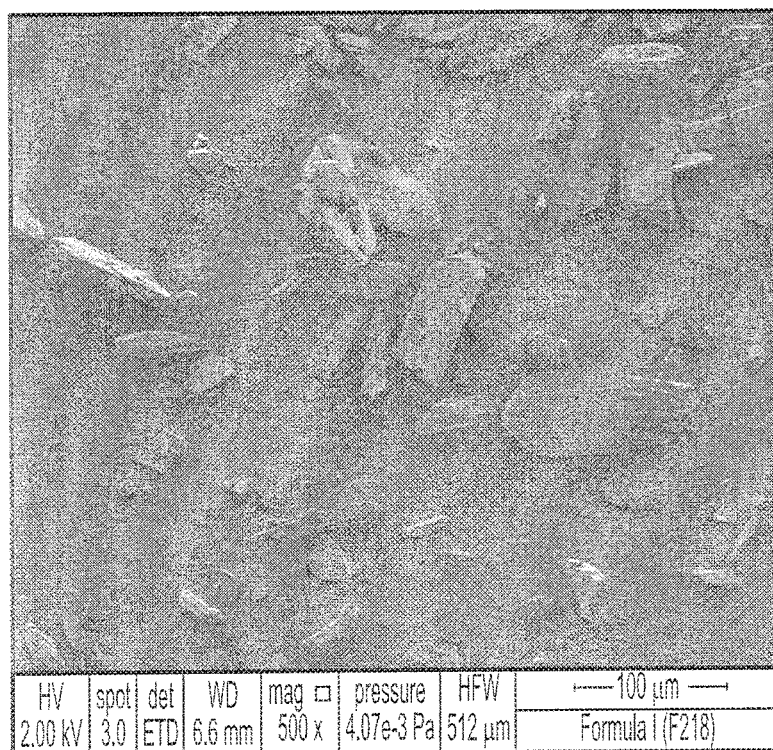
FIG. 4A depicts a scanning electron microscopic (SEM) photograph of the particulates of a sample of Formula I in Form I at magnification of 500.
Figure 4B:
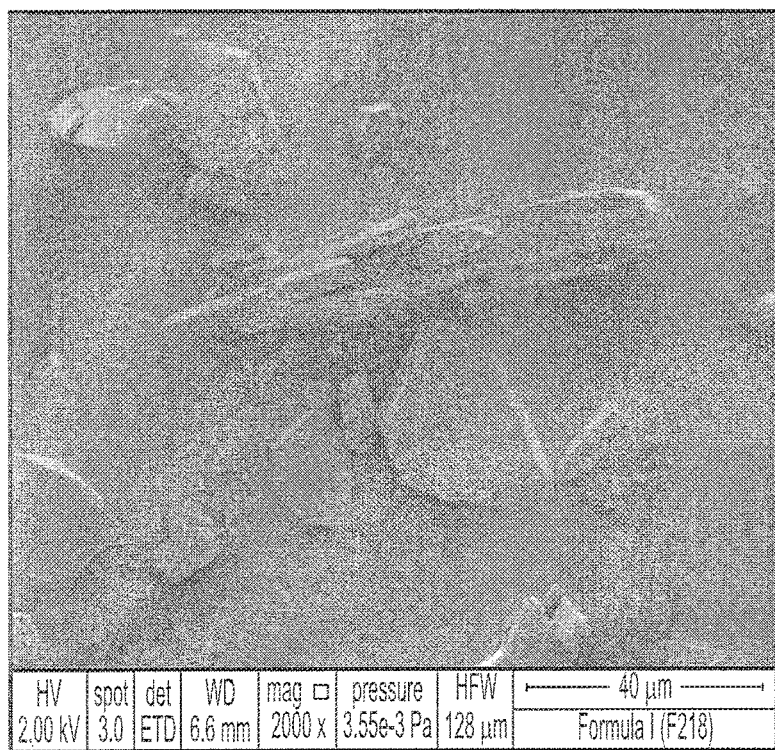
FIG. 4B depicts a scanning electron microscopic (SEM) photograph of the particulates of a sample of Formula I in Form I at magnification of 2,000.
Figure 4C:
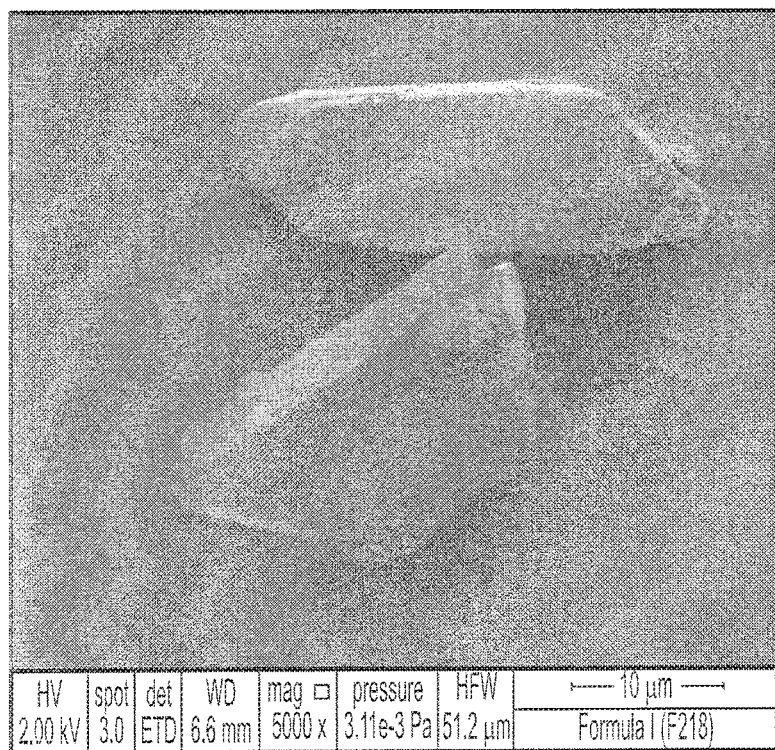
FIG. 4C depicts a scanning electron microscopic (SEM) photograph of the particulates of a sample of Formula I in Form I at magnification of 5,000.

The X-ray powder diffraction pattern of Form I is illustrated in FIG. 1. Form I has characteristic XRP diffraction peaks expressed in two-theta at approximately at 6.3, 17.9, and 19.7°, suggesting that the compound is crystalline. As shown in FIG. 4, the particles are of regular shaped and plate-like morphology.

The differential scanning calorimetric thermogram of Form I is illustrated in FIG. 2. Form I exhibit an endothermic event with an onset temperature of about 240° C. with a peak temperature of 243° C.

The thermogravimetric analysis thermogram of Form I is shown in FIG. 2. Form I is very stable and shows less than about 0.4% weight loss when heated from about 25° C. to about 140° C.

The gravimetric vapour sorption system plot of Form I is shown in FIG. 3. Form I exhibit a mass increase of less than about 1% when subjected to a an increase in relative humidity from about 0% to about 95% relative humidity.

Example 3

Recrystallization Studies of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate), Form I To 24.10 g of Form I was added 24 ml of acetonitrile/3% water (v/v). The suspension was heated to 76° C., a clear solution was observed which was then cooled at 0.2° C./min down to 5° C. without seeding. The solid was filtered and dried in a vacuum oven for 2.5 days at 50° C. to yield 72% of Form I with the characteristic XRPD of FIG. 1.

In another experiment, to 1.50 g of Form I was added 8 ml of 1-propanol (5.3 vol.). The suspension was heated at 88° C., a clear solution was observed which was then cooled at 0.5° C./min down to 5° C. without seeding. The solid was filtered and dried in a vacuum oven for 2.5 days at 50° C. to yield 88% Form I with the characteristic XRPD of FIG. 1.

In general, Form I can be recrystallized successfully using 10 volumes of acetonitrile/3% water (v/v) or 1-propanol. The quantity of water is critical when using acetonitrile: 3% of water is needed to get a good solubility of the material, but 4% water may lead to Form IV.

Example 4

Solubility of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate), Form I, in Aqueous solutions and in Organic solvents 100 mg of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate), Form I was weighed into a glass vial, and 1 ml of the relevant aqueous media was added. The vials were shaken. After 1 hr, a sample (~0.5 ml) was removed via syringe, and filtered through a syringe filter (0.2 micron) into a second vial. 200 µl of each solution was then transferred into an HPLC vial and made up to 1 ml by adding 800 µl of diluent. These samples were analyzed directly by HPLC, and the response was outside the linearity range. Therefore a second dilution was performed, taking 0.1 ml of each sample and making up to 2 ml with diluent. The samples were re-analyzed by HPLC. Then after shaking the suspensions for 18 hours in total, a second sample was taken as above. All samples were then diluted and analyzed by HPLC, as above. The temperature was noted (22° C.), and no gelling was observed.

Form I shows quite consistent and quite high solubility over the range of pHs tested (1.2-6.8). It is slightly higher at pH 1.2 and pH 6.8.

The above procedure was repeated but using 8 different organic solvents in place of the aqueous media (analysis only after 18 hrs). Solvents used were acetonitrile, diethyl ether, ethanol, ethyl acetate, isopropanol, methanol, heptane and THF. All solvents gave suspensions at 100 mg/ml, except methanol which dissolved at 100 mg in 0.3 ml. Therefore, an extra 70 mg of Form I was added to the methanol vial to result in a suspension. These experiments were sampled once after 18 hours of slurrying. The results are reported in Table 3.

Example 5

Particle size Measurement of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate), Form I The average particle size and particle size distribution of the particulates in Form I were measured using Malvern Mastersizer MicroPlus Analyzer (Malvern Instruments, UK) using isooctane as dispersant for the experiment. The equipment was left to warm up for about 1 hour and approximately 100 ml of the dispersant was added to the sample dispersion unit. Backgrounds were first measured using the dispersant. A fresh sample was prepared by adding ~100 mg of Form I into 2 ml of the dispersant and this was sonicated for ~5 mins. The sample was added drop-wise into the sample dispersion unit while stirring the dispersant until a suitable obscuration value (i.e., 16-25%) was achieved and the particle size distribution could be measured. A minimum of three measurements were made for each sample.

The Particle Size Distribution (PSD) results for (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate), Form I, may be found in the Table 4. These are selected values from the repeat measurements.

Example 6

Stability Studies of (S)-(2R,3R,11bR)-3-isobutyl-9, 10-dimethoxy-2,3,4,6,7,11b-hexahydro-1H-pyrido[2, 1-a]isoquinolin-2-yl 2-amino-3-methylbutanoate di(4-methylbenzenesulfonate), Form I Two lots of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate), Form I, have been placed on stability for 60 months duration at the long-term and intermediate storage conditions and for 6 months duration at the accelerated storage condition. The storage conditions include the long-term storage condition of 25±2° C./60±5% RH, the intermediate storage condition of 30±2° C./65±5% RH, and the accelerated storage condition of 40±2° C./75±5% RH. Stability results are reported in Table 5.

Up to 3 months of stability data are presented in Table 5 for two lots of Form I. The results of accelerated and long-term stability studies for these lots demonstrate the chemical and physical stability of Form I when stored for up to 3 months at the long-term storage condition of 25° C./60%/RH and 3 months at the accelerated storage condition of 40° C./75% RH.

TABLE 1

Solubility of Formula I, in Form I, at 5° and 10° C. below reflux for each solvent.

| Solvent | Boiling Point | Solubility at high temperature (mg/ml) | Solubility at 5° C. temperature (mg/ml) |
|---|---|---|---|
| Ethyl Acetate | 77 | 2 | 1 |
| Isopropyl Acetate | 89 | 4 | 4 |
| IPA | 89 | 22 | 5 |
| THF | 66 | 6 | 4 |
| MIBK | 117 | 5 | 6 |
| MEK | 80 | 4 | 3 |
| Acetone | 56 | Could not be filtered | 5 |
| Acetonitrile | 81 | 48 | 17 |
| MeOH | 65 | >250 | >250 |
| EtOH | 78 | 212 | 24 |
| 1-propanol | 98 | 160 | 8 |

TABLE 2

Aqueous solubility of Form I.

| Aqueous pH | SOLUBILITY (mg/ml) | |
|---|---|---|
| | 1 hr | 18 hrs |
| 1.2 | 31.61 | 33.17 |
| 3 | 28.45 | 27.97 |
| 4 | 28.06 | 27.75 |
| 5 | 18.58 | 27.87 |
| 6.8 | 33.98 | 35.35 |

TABLE 3

Solubility of Form I in organic solvents.

| Solvent | Solubility (mg/ml) – 18 hrs |
|---|---|
| Water | 28.2 |
| Methanol | 480.8 |
| Ethanol | 35.5 |
| Isopropanol | 1.15 |
| Ethyl acetate | 0.04 |
| Acetonitrile | 1.36 |
| THF | 0.05 |
| Diethyl ether | 0.01 |
| Heptane | 0.003 |

TABLE 4

Particle size distribution of Form I.

| Form | Treatment | Particle size parameter (microns) | | | | |
|---|---|---|---|---|---|---|
| | | D10 | D20 | D50 | D80 | D90 |
| Form I | Suspended in iso-octane and sonicated 5 min | 10.29 | 17.84 | 34.72 | 56.22 | 69.39 |

TABLE 5

Stability data for three lots of Form I.

| Lot | Storage Condition | Stability Data Available |
|---|---|---|
| 1 | 25° C./60% RH | 3 months |
| | 40° C./75% RH | 3 months |
| 2 | 25° C./60% RH | 3 months |
| | 40° C./75% RH | 3 months |
| 3 | 25° C./60% RH | 24 months |
| | 40° C./75% RH | 6 months |

TABLE 6

Recrystallization Studies of Form I.

| Recrystallization | XRPD | NMR | Purity HPLC | Yield |
|---|---|---|---|---|
| — | Crystalline-Form I | No residual solvent –2.0 eq. of acid | 100% | — |
| Acetonitrile/3% water | Crystalline-Form I | No residual solvent –2.0 eq. of acid | 100% | 72% |
| 1-propanol | Crystalline-Form I | No residual solvent –1.9 eq. of acid | 97.4% | 88% |

Example 7

Preparation of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate), Form II 186 mg of amorphous (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) was slurried in 3 volumes of water overnight (4 h heat/cool cycle between RT and 50° C.). A white crystalline material was obtained and dried in a vacuum oven at 40° C. for 4 h.

The X-ray powder diffraction pattern of Form II is illustrated in FIG. 5. Form II has characteristic XRP diffraction peaks expressed in two-theta at approximately 5.7, 15.3, and 22.5°, suggesting that the compound is in a crystalline form (Form II) that is different from Form I.

The differential scanning calorimetric thermogram of Form II is illustrated in FIG. 6. Form II exhibit an endothermic event with an onset temperature of about 143° C. with a peak temperature of 155° C.

Example 8

Preparation of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate), Form III Maturation of 100 mg of amorphous (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) in 95:5 1,4-dioxane/water for 72 h, cycling between ambient and 50° C. every 4 h gave a solid. The solid was isolated by filtration and dried under vacuum for 3 h.

The X-ray powder diffraction pattern of Form III is illustrated in FIG. 8. Form III has characteristic XRP diffraction peaks expressed in two-theta at approximately 6.3, 18.3, 18.9, 19.8, and 20.4°, suggesting that the compound is in a crystalline form (Form III) that is different from Form I, or II.

The differential scanning calorimetric thermogram of Form III is illustrated in FIG. 9. Form III exhibit an endothermic events temperatures of about 93° C., about 158° C., and about 230° C.

Example 9

Preparation of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate), Form IV (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) (500 mg) was dissolved in 1.0 ml acetonitrile/10% water at 71° C. The clear solution was then cooled down at 10° C./hr down to 5° C. The solid was filtered and dried at 30° C. under vacuum for 1.5 hour.

The X-ray powder diffraction pattern of Form IV is illustrated in FIG. 10. Form IV has characteristic XRP diffraction peaks expressed in two-theta at approximately 6.2, 10.4, 17.9, 19.2, 19.9, and 20.2°, suggesting that the compound is in a crystalline form (Form IV) that is different from Form I, IL, or III.

The differential scanning calorimetric thermogram of Form IV is illustrated in FIG. 11. Form IV exhibit an endothermic events temperatures of about 128° C., about 159° C., and about 237° C.

Example 10

Preparation of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate), Form V 1.41 g of amorphous (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) was slurried in 5 ml of water for 4 hours. A white crystalline material was filtered and dried. The mother liquors were kept. Crystalline needles precipitated from the mother liquors after 48 h. The particles were dried in a vacuum oven at RT for 2 h.

The X-ray powder diffraction pattern of Form V is illustrated in FIG. 13. Form V has characteristic XRP diffraction peaks expressed in two-theta at approximately 6.7, 7.9, 10.7, 12.8, 17.1, and 23.7°, suggesting that the compound is in a crystalline form (Form V) that is different from either Form I, II, III, or IV.

The differential scanning calorimetric thermogram of Form V is illustrated in FIG. 14. Form V exhibit an endothermic events temperatures of about 113° C., and about 181° C.

Example 11

Preparation of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate), Form VI 1.41 g of amorphous (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) was slurried in 5 ml of water for 4 hours. A white crystalline material was filtered and dried in a vacuum oven at 40° C. overnight.

The X-ray powder diffraction pattern of Form VI is illustrated in FIG. 16. Form VI has characteristic XRP diffraction peaks expressed in two-theta at approximately 6.8, 8.0, 16.3, and 17.5°, suggesting that the compound is in a crystalline form (Form VI) that is different from either Form I, IL, III, IV, or V.

The differential scanning calorimetric thermogram of Form VI is illustrated in FIG. 17. Form VI exhibit an endothermic events temperatures of about 175° C., and about 238° C.

Example 12

Phase Equilibration Between Form I, IL, and IV of Formula I

Form I (80 mg), Form II (50 mg) and Form IV (20 mg) were mixed together. About 10 mg of the mixture was then slurried in 200 µl of pre-saturated solvent at the desired temperatures for 13 days. The solids were then quickly filtered and analyzed by XRPD.

Form IV was found to be the thermodynamic product at 5° C. for mixture of acetonitrile/water >2%. At 25° C., only Form I was observed. The results are summarized in Table 7.

Example 13

Phase Equilibration Between Form I and IV of Formula I

The suspensions of Form I and IV from the equilibration studies were taken to 25° C. Form IV did not convert after overnight stirring. The samples were then heated to 30° C. for 2 days, the conversion to Form I was then complete. The results are reported in Table 8.

TABLE 6

Equilibration studies between Form I, II, and IV.

| Solvent | 5° C. | 25° C. | 50° C. |
|---|---|---|---|
| Acetonitrile | Form I | Form I | Form I |
| Acetonitrile/2% water | Form I-Poorly crystalline | Form I | Form I |
| Acetonitrile/5% water | Form IV | Form I | Form I |
| Acetonitrile/10% water | Form IV | Form I | Form I |

TABLE 7

Equilibration studies between Form I and IV of Formula I.

| Observation after heating at 30° C. (overnight) | XRPD results | Observation after heating at 30° C. (2 days) | XRPD results |
|---|---|---|---|
| White precipitate | Form IV + trace of Form I | White precipitate | Form I |
| White precipitate | Form IV | White precipitate | Form I |
| White precipitate | Form IV | White precipitate | Form I |
| White precipitate | Form IV | White precipitate | Form I |
| White precipitate | Form IV | White precipitate | Form I |

TABLE 8

X-Ray Powder Diffraction of Form I of Formula I.

| Angle 2-Theta ° | Intensity % |
|---|---|
| 5.4 | 5 |
| 6.3 | 100 |
| 8.5 | 3 |
| 9.8 | 3 |
| 10.8 | 3 |
| 11.4 | 3 |
| 11.5 | 4 |
| 12.6 | 4 |
| 12.8 | 5 |
| 13.8 | 5 |
| 15.6 | 12 |
| 16.2 | 4 |
| 16.6 | 12 |
| 16.9 | 5 |
| 17.1 | 7 |
| 17.9 | 13 |
| 18.4 | 10 |
| 19.7 | 46 |
| 20.0 | 11 |
| 20.6 | 6 |
| 20.9 | 5 |
| 22.1 | 6 |
| 22.7 | 13 |
| 23.1 | 9 |
| 24.4 | 7 |
| 24.6 | 8 |
| 25.3 | 7 |
| 25.7 | 4 |
| 26.3 | 4 |
| 30.4 | 4 |
| 35.4 | 4 |

TABLE 9

X-Ray Powder Diffraction of Form II of Formula I.

| Angle 2-Theta ° | Intensity % |
|---|---|
| 5.7 | 100 |
| 7.1 | 5 |
| 7.6 | 5 |
| 10.2 | 4 |
| 10.4 | 4 |
| 11.5 | 6 |
| 14.2 | 12 |
| 15.3 | 26 |
| 15.9 | 12 |
| 16.5 | 4 |
| 16.9 | 6 |
| 17.5 | 5 |
| 17.9 | 5 |
| 18.6 | 10 |
| 19.9 | 4 |
| 20.3 | 6 |
| 20.5 | 8 |
| 20.8 | 8 |
| 21.7 | 4 |
| 22.5 | 15 |
| 22.8 | 6 |
| 23.1 | 6 |
| 23.5 | 5 |
| 24.6 | 4 |
| 27.0 | 6 |
| 27.6 | 6 |
| 28.6 | 5 |
| 28.9 | 6 |
| 30.2 | 4 |
| 40.3 | 4 |

TABLE 10

X-Ray Powder Diffraction of Form III of Formula I.

| Angle 2-Theta ° | Intensity % |
|---|---|
| 6.3 | 100 |
| 7.1 | 4 |
| 11.7 | 4 |
| 12.2 | 8 |
| 13.2 | 5 |
| 14.1 | 8 |
| 14.3 | 11 |

TABLE 10-continued

X-Ray Powder Diffraction of Form III of Formula I.

| Angle 2-Theta ° | Intensity % |
|---|---|
| 14.8 | 4 |
| 15.3 | 14 |
| 15.6 | 3 |
| 16.3 | 9 |
| 16.6 | 5 |
| 16.9 | 9 |
| 17.4 | 9 |
| 18.3 | 29 |
| 18.9 | 21 |
| 19.8 | 35 |
| 20.4 | 25 |
| 21.2 | 10 |
| 21.3 | 9 |
| 22.3 | 4 |
| 22.8 | 7 |
| 23.5 | 6 |
| 24.1 | 13 |
| 24.3 | 7 |
| 24.5 | 5 |
| 24.8 | 5 |
| 29.7 | 6 |
| 29.9 | 7 |

TABLE 11

X-Ray Powder Diffraction of Form IV of Formula I.

| Angle 2-Theta ° | Intensity % |
|---|---|
| 3.7 | 4 |
| 5.0 | 4 |
| 6.2 | 100 |
| 9.0 | 9 |
| 9.9 | 3 |
| 10.4 | 10 |
| 10.7 | 3 |
| 11.1 | 7 |
| 11.5 | 3 |
| 12.5 | 6 |
| 12.7 | 5 |
| 14.6 | 6 |
| 16.0 | 8 |
| 16.9 | 9 |
| 17.3 | 9 |
| 17.9 | 10 |
| 18.5 | 5 |
| 18.8 | 8 |
| 19.2 | 11 |
| 19.9 | 10 |
| 20.2 | 19 |
| 21.0 | 9 |
| 21.6 | 7 |
| 22.6 | 6 |
| 24.8 | 4 |
| 25.7 | 6 |
| 27.2 | 7 |

TABLE 12

X-Ray Powder Diffraction of Form V of Formula I.

| Angle 2-Theta ° | Intensity % |
|---|---|
| 5.4 | 24 |
| 6.7 | 100 |
| 7.9 | 70 |
| 8.3 | 5 |
| 10.7 | 24 |
| 12.8 | 18 |
| 13.1 | 17 |
| 13.5 | 15 |
| 14.1 | 6 |
| 14.3 | 5 |
| 14.7 | 4 |
| 15.4 | 4 |
| 15.8 | 29 |
| 16.0 | 26 |
| 17.1 | 30 |
| 17.8 | 5 |
| 18.4 | 16 |
| 19.4 | 11 |
| 19.9 | 11 |
| 20.2 | 13 |
| 20.4 | 10 |
| 20.6 | 11 |
| 20.9 | 11 |
| 21.5 | 27 |
| 21.8 | 9 |
| 22.7 | 9 |
| 23.7 | 31 |
| 24.0 | 13 |
| 24.2 | 14 |
| 24.5 | 5 |
| 24.8 | 7 |
| 25.1 | 7 |
| 25.8 | 6 |
| 26.3 | 6 |
| 26.5 | 7 |
| 26.9 | 5 |
| 27.5 | 11 |
| 28.3 | 8 |
| 29.5 | 8 |
| 29.8 | 13 |
| 30.7 | 5 |
| 31.6 | 7 |
| 33.0 | 5 |
| 37.1 | 6 |
| 39.6 | 9 |
| 41.2 | 5 |

TABLE 13

X-Ray Powder Diffraction of Form VI of Formula I.

| Angle 2-Theta ° | Intensity % |
|---|---|
| 5.4 | 29 |
| 6.8 | 100 |
| 8.0 | 48 |
| 8.4 | 4 |
| 11.1 | 6 |
| 11.6 | 5 |
| 13.6 | 8 |
| 14.2 | 6 |
| 16.3 | 15 |
| 16.8 | 6 |
| 17.5 | 20 |
| 17.8 | 12 |
| 18.7 | 14 |
| 19.0 | 8 |
| 19.4 | 5 |
| 19.7 | 10 |

TABLE 13-continued

X-Ray Powder Diffraction of Form VI of Formula I.

| Angle 2-Theta ° | Intensity % |
| --- | --- |
| 20.1 | 8 |
| 20.9 | 12 |
| 21.3 | 12 |
| 21.5 | 12 |
| 22.1 | 13 |
| 22.5 | 11 |
| 23.5 | 6 |
| 24.2 | 7 |
| 25.4 | 6 |
| 27.1 | 6 |
| 27.4 | 6 |

Example 14

Preparation of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride (Formula II), Form I To a suspension of (2R,3R,11bR)-3-isobutyl-9,10-dimethoxy-2,3,4,6,7,11b-hexahydro-1H-pyrido[2,1-a]isoquinolin-2-ol salt (32.3 g, 58.54 mmol) in dichloromethane (300 mL) was added 0.5 M aq. NaOH solution (150 mL). The organic layer was separated and washed with water (50 mL) and then dried over $Na_2SO_4$. The organic layer was filtered and to the resulting mixture was added DMAP (1.79 g, 0.25 equiv., 14.63 mmol) and Boc-L-Val-OH (15.26 g, 1.2 equiv., 70.25 mmol). The reaction mixture was cooled to −10° C., EDC (16.83 g, 1.5 equiv., 87.81 mmol) was added and the resulting mixture was stirred for 3 hrs. To the mixture was added 0.2 equiv. of Boc-L-Val-OH (2.54 g) and 0.25 equiv. of EDC (2.8 g). After 1.5 hrs of stirring, water was added (50 mL), the organic layer was separated and washed with aq. 5% citric acid solution (2×100 mL). The combined organic extracts were washed with water (100 mL) and then dried over $Na_2SO_4$. The organic layer was filtered and dried.

The crude was taken in dichloromethane and cooled to 5° C. To the mixture was added 4M HCl solution in dioxane (64.37 mL, 4.4 equiv., 257.50 mmol). Additional 20 mL of 4M HCl solution in dioxane was added. After 5 hrs the reaction mixture was cooled to 10° C. and 8% aq. $NaHCO_3$ solution (700 mL) was added. The organic layer was separated and the aqueous layer was extracted with dichloromethane (100 mL). The combined organic extracts were washed with water and then dried over $Na_2SO_4$, filtered and concentrated under vacuum to give a residue. To the residue was added acetonitrile and the resulting mixture was treated with 2.1 equiv. of 3.5 N HCl in IPA solution at 5° C. The reaction mixture was warmed to room temperature. EtOAc was added and the mixture heated to 50° C. and seeded with 165 mg of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride. After 30 min stirring at 50° C. was added more EtOAc and the mixture was refluxed for 1 h. The heating was removed and the mixture was allowed to reach room temperature. Solids were removed by filtration and washed with EtOAc to give 15.4 g of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride.

The X-ray powder diffraction pattern of Form I is illustrated in FIG. 20. Form I has characteristic XRP diffraction peaks expressed in two-theta at approximately 7.2, 9.2, and 18.0°, suggesting that the compound is in a crystalline form (Form I). Thermal analysis exhibit a mass increase of about 14% when subjected to a an increase in relative humidity from about 0% to about 90% relative humidity. Storage at 25° C./92% RH and 40° C./75% RH for seven days both induced a change of form. Aqueous solubility was assessed as >90 mg/mL free form equivalent at pH 4.1.

Example 15

Preparation of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride (Formula II), Form II Form II was prepared by spreading 200 mg of (S)-(2R,3R,1bR)-3-isobutyl-9,10-dimethoxy-2,3,4,6,7,11b-hexahydro-1H-pyrido[2,1-a]isoquinolin-2-yl 2-amino-3-methylbutanoate dihydrochloride (Formula II), in Form I, in a thin layer in an eating dish and exposing the sample to an environment of 25° C./75% RH for 72 h.

The X-ray powder diffraction pattern of Form II is illustrated in FIG. 24. Form II has characteristic XRP diffraction peaks expressed in two-theta at approximately 4.8, 13.3, and 24.9°, suggesting that the compound is in a crystalline form (Form II) that is different from that of Form I. Thermal analysis showed a 10.4% mass loss, while Karl Fisher analysis gave the water content as 13.9% m/m. Aqueous solubility was assessed as >67 mg/mL free form equivalent at pH 4.1.

A VT-XRPD study showed no conversion to Form I on heating; the material becoming amorphous at temperatures above about 160° C. with no subsequent crystallization upon cooling. GVS analysis showed the material to lose ca. 12% of its mass when the RH is lowered to 0%. It is not clear whether a form change accompanies this loss of water, as the water is readily taken back up when the sample is returned to ambient RH.

TABLE 14

X-Ray Powder Diffraction of Form I of Formula II.

| Angle 2-Theta ° | Intensity % |
| --- | --- |
| 6.9 | 22 |
| 7.2 | 100 |
| 7.2 | 100 |
| 8.2 | 13 |
| 9.2 | 37 |
| 10.7 | 13 |
| 12.7 | 14 |
| 14.0 | 8 |
| 15.1 | 11 |
| 16.4 | 7 |
| 17.4 | 10 |
| 18.0 | 34 |
| 18.4 | 13 |
| 20.0 | 12 |
| 20.8 | 24 |
| 22.5 | 18 |
| 23.3 | 10 |
| 23.7 | 8 |
| 24.0 | 13 |
| 24.2 | 7 |
| 25.3 | 7 |
| 25.7 | 8 |
| 25.9 | 19 |
| 27.7 | 6 |
| 29.0 | 7 |
| 29.6 | 8 |
| 30.3 | 7 |
| 31.0 | 8 |

TABLE 14-continued

X-Ray Powder Diffraction of Form I of Formula II.

| Angle 2-Theta ° | Intensity % |
|---|---|
| 33.2 | 8 |
| 36.6 | 9 |

TABLE 15

X-Ray Powder Diffraction of Form II of Formula II.

| Angle 2-Theta ° | Intensity % |
|---|---|
| 4.3 | 52 |
| 4.8 | 100 |
| 7.2 | 18 |
| 7.6 | 20 |
| 8.4 | 44 |
| 8.7 | 45 |
| 9.5 | 36 |
| 10.6 | 20 |
| 10.9 | 24 |
| 11.5 | 19 |
| 12.4 | 15 |
| 12.8 | 16 |
| 13.3 | 69 |
| 14.1 | 53 |
| 14.6 | 40 |
| 15.3 | 21 |
| 16.3 | 13 |
| 16.6 | 18 |
| 17.1 | 18 |
| 18.4 | 47 |
| 19.0 | 13 |
| 20.0 | 22 |
| 20.3 | 16 |
| 21.1 | 29 |
| 21.3 | 21 |
| 22.1 | 16 |
| 23.7 | 15 |
| 24.5 | 16 |
| 24.9 | 72 |
| 25.3 | 39 |
| 25.7 | 26 |
| 26.1 | 24 |
| 26.5 | 36 |
| 26.7 | 39 |
| 27.2 | 18 |
| 27.5 | 17 |
| 27.9 | 17 |
| 28.1 | 16 |
| 28.4 | 17 |
| 28.8 | 20 |
| 29.2 | 18 |
| 30.5 | 18 |

Example 16

Preparation of Amorphous (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) and (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride (Formula II)

About 15 mg of (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) and (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride (Formula II) were each taken up in 2 mL of 2:1 tBuOH:water. The resulting clear solutions were flash frozen in a dry-ice/acetone bath and lyophilized to fluffy white solids. XRPD analysis showed the freeze dried material to be amorphous in each case, and $^1$H NMR confirmed that the respective counter-ions were still present.

Example 17

Maturation Array of Amorphous (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate di(4-methylbenzenesulfonate) (Formula I) and (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochloride (Formula II)

About 50 mg of amorphous (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbenzenesulfonate) (Formula I) and (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate dihydrochoride (Formula II) was weighed into each of 48 vials. Enough of the specified solvent was added to form mobile slurry and the vials we incubated for 72 h, cycling between ambient and 50° C. every 4 h. Any solids present at this point were isolated by filtration and analysed by XRPD. Experiments without solid were uncapped and allowed to nucleate; none of these furnished any crystalline material, all giving sticky gums. Results are shown on Table 16.

TABLE 16

Maturation array on amorphous salts of Formula I and Formula II.

| | | Bis-Tosylate | | | Bis-Hydrochloride | |
|---|---|---|---|---|---|---|
| Details Solvent | Volume (µL) | Solid isolated after | XRPD | Volume (µL) | Solid isolated after | XRPD |
| Heptane | 500 | maturation | Form I | 500 | maturation | amorphous |
| Dioxane | 250 | maturation | Possible mixture | 500 | maturation | Form I |

TABLE 16-continued

Maturation array on amorphous salts of Formula I and Formula II.

| | Bis-Tosylate | | | Bis-Hydrochloride | | |
|---|---|---|---|---|---|---|
| Details Solvent | Volume (µL) | Solid isolated after | XRPD | Volume (µL) | Solid isolated after | XRPD |
| Toluene | 500 | maturation | New Pattern (2) | 500 | maturation | partially crystalline Form II |
| Cumene | 500 | maturation | New Pattern (2) | 500 | maturation | partially crystalline Form II |
| TBME | 500 | maturation | Form I | 500 | maturation | amorphous |
| Tetraline | 500 | gum after evap | n/a | 500 | gum after evap | n/a |
| DIPE | 500 | maturation | Form I | 500 | maturation | amorphous |
| Anisole | 250 | maturation | New Pattern (2) | 500 | gum after evap | n/a |
| Isobutyl acetate | 250 | maturation | New Pattern (2) | 500 | maturation | amorphous |
| Ethyl actetate | 500 | maturation | Form I | 500 | maturation | Form I |
| Isopropyl acetate | 500 | maturation | Form I | 500 | maturation | amorphous |
| Methyl acetate | 500 | maturation | Possible mixture | 500 | maturation | Form I |
| IPA | 250 | maturation | Form I | 500 | gum after evap | n/a |
| Ethyl formate | 250 | maturation | Form I | 500 | maturation | new pattern (3) |
| THF | 250 | maturation | Form I | 500 | maturation | Form I |
| DCE | 250 | maturation | Poorly crystalline | 500 | gum after evap | n/a |
| MIBK | 500 | maturation | Form I | 500 | maturation | amorphous |
| MEK | 250 | maturation | Form I | 500 | maturation | Form I |
| Acetone | 250 | maturation | Form I | 500 | maturation | Form I |
| Methanol | 250 | gum after evap | n/a | 500 | gum after evap | n/a |
| Ethanol | 250 | gum after evap | n/a | 500 | gum after evap | n/a |
| Acetonitrile | 250 | maturation | Form I | 500 | gum after evap | n/a |
| Nitromethane | 250 | maturation | Form I | 500 | gum after evap | n/a |
| Water | 250 | maturation | New Pattern (2) | 500 | gum after evap | n/a |

Example 18

Counter-ion screen of (S)-2-amino-3-methyl-butyric acid (2R,3R,1bR)-3-isobutyl-9,10-dimethoxy-1,3,4,6,7,11b-hexahydro-2H-pyrido[2,1-a]isoquinolin-2-yl ester About 50 mg (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester free base was weighed into each of 54 HPLC vials 500 µL of the relevant solvent was then added to each and the vials shaken at room temperature for 1 h, giving clear solutions in all cases. 2.0 eq of the relevant acid was then added to each experiment. The vials were then placed in an incubator for 16 h, cycling between ambient and 50° C. every 4 h. Any visible solids were filtered off and analyzed by XRPD. Any vials containing gums were incubated for a further 60 h, after which point any solids were isolated by filtration and characterized by XRPD.

Example 19

Anti-Solvent Mediated Counter-Ion Screen of (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester About 50 mg of (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester free base was weighed into each of 27 reaction tubes. To 18 of these was added 500 µL of acetonitrile, to the other nine was added 500 µL of 99:1 acetonitrile/water. 2.1 eq of the relevant acid was then added, in the most concentrated form available. Enough ethyl acetate was added to each tube to induce cloudiness and the tubes were heated to 50° C. for 1 h before being allowed to cool to RT, with constant stirring. Any solids present were filtered off and analyzed by XRPD. In addition to reproducing the crystalline salt forms of tosic acid and oxalic acid isolated in Example 18, new crystalline hydrobromide and methanesulfonate salts were identified, as well as a benzenesulfonate salt with a different diffraction pattern to that observed previously. DSC analysis of this new besylate form showed an early endothermic event followed by an apparent re-crystallization and subsequent melt. Results are shown in Tables 17.

TABLE 17

Results from anti-solvent mediated counter-ion screen.

| Experimental Details | | MeCN (no added water) - A | | MeCN (1% added water) - A | |
| --- | --- | --- | --- | --- | --- |
| Acid | Added as | observations | XRPD | observations | XRPD |
| Hydrobromic acid | 48% aq. solution | oil (xtal on standing) | crystalline | oil | |
| Hydrochloric acid | 4M dioxane solution | fine solid | deliquesced | oil | |
| Sulphuric acid | 97.50% | Oil | | oil | |
| 1,2-ethanedisulphonic acid | solid | Gum | | oil | |
| p-Toluene sulphonic acid | solid (monohydrate) | fine solid | crystalline | fine solid | crystalline |
| Methane sulphonic acid | solid | oil (xta on standing) | crystalline | fine solid | crystalline |
| Benzene sulphonic acid | solid | fine solid | crystalline | fine solid | crystalline |
| Oxalic acid | solid | fine solid | partially crystalline | fine solid | partially crystalline |
| Maleic acid | solid | Oil | | oil | |
| Phosphoric acid | 85% aq. Solution | fine solid | deliquesced | experiment not performed | |
| L-Tartaric acid | solid | Gum | | experiment not performed | |
| Fumaric acid | solid | unfilterable gel | | experiment not performed | |
| Citric acid | solid | fine solid | deliquesced | experiment not performed | |
| L-Malic acid | solid | Gum | | experiment not performed | |
| Hippuric acid | solid | fine solid | input acid | experiment not performed | |
| D-gluconic acid | 45% wt. in water | Oil | | experiment not performed | |
| L-lactic acid | solid | Oil | | experiment not performed | |
| Succinic acid | solid | Oil | | experiment not performed | |

Example 20

Polymorphic Assessment of Salts from Anti-Solvent Mediated Counter-Ion Screen of (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester About 10 mg of the relevant salt form was suspended in 100 μL of the specified solvent. The suspensions were then incubated for 72 h, cycling between ambient and 50° C. every 4 h. After cooling to RT, any solids present were filtered off and analyzed by XRPD. The results are shown on Table 18.

TABLE 18

Results of polymorphism assessment.

| Details Solvent | A - Tosylate Pattern | B - Oxalate Pattern | C - Mesylate Pattern | D - Besylate Pattern | E - Hydrobromide Pattern |
| --- | --- | --- | --- | --- | --- |
| MeOH | n/a | n/a | n/a | n/a | n/a |
| MeCN | possible new pattern (1) | amorphous | possible new pattern (1) | largely amorphous | form one |
| IPA | form one | form one | form one | possible new pattern (1) | form one |
| MEK | possible new pattern (2) | possible new pattern (1) | form one | possible new pattern (2) | possible new pattern (1) |

TABLE 18-continued

Results of polymorphism assessment.

| Details Solvent | A - Tosylate Pattern | B - Oxalate Pattern | C - Mesylate Pattern | D - Besylate Pattern | E - Hydrobromide Pattern |
|---|---|---|---|---|---|
| MIBK | form one | possible new pattern (2) | form one | form one | new pattern (2) |
| DCM | form one | possible new pattern (3) | form one | form one | new pattern (2) |
| THF | form one | largely amorphous | form one pattern (1) | possible new | form one |
| IPAc | form one | form one | form one | form one | form one |
| DIPE | form one | form one | form one | form one | form one |
| TBME | form one | form one | largely amorphous | form one | form one |

While diffraction patterns with extra peaks were noted for all the salts (labelled as possible new patterns in the table above), a new form w a s conclusively identified for the hydrobromide salt, isolated from MIBK and DCM. In the other cases, the material was mostly of the same form put into the experiments, with some additional peaks present.

TABLE 19

Summary of salts formed.

| | Synthetic details | | Characterization | | | Aqueous solubility | | Stability to humidity | | |
|---|---|---|---|---|---|---|---|---|---|---|
| | | | Eq | | mp onset | mg/mL | | 40° C./75% | 25° C./92% | GVS |
| Salt form | Yield | Purity | counterion | XRPD | (° C.) | free form | pH | RH | RPH | uptake |
| tosylate | 69% | 99.1% | 2.1 by NMR | crystalline | 239 | 15.00 | 5.24 | unchanged | unchanged | 1.0% |
| oxalate | 74% | 98.2% | 2.1 by IC | crystalline | 200 | >50 | 2.43 | unchanged | unchanged | 0.8% |
| mesylate | 85% | 98.4% | 2.1 by NMR | crystalline | 177 | >70 | 3.97 | unchanged | deliquesced | 3.4% |
| besylate | 86% | 99.1% | 2.0 by NMR | crystalline | 239 | 25.1 | 4.74 | unchanged | unchanged | 3.7% |
| hydrobromide | 61% | 98.7% | 2.0 by IC | crystalline | 158, 248 | 85.3 | 3.38 | form change | form change | >3.9% |
| hydrochloride | n/a | 99.0% | 2.1 by IC | crystalline | 244 | >90 | 4.09 | form change | form change | 15.2% (form change) |

All the salts formed showed bis stoichiometry and purity comparable to the input material.

The examples set forth above are provided to give those of ordinary skill in the art with a complete disclosure and description of how to make and use the embodiments, and are not intended to limit the scope of the disclosure. Modifications of the above-described modes for carrying out the disclosure that are obvious to persons of skill in the art are intended to be within the scope of the following claims. All publications, patents, and patent applications cited in this specification are incorporated herein by reference as if each such publication, patent, or patent application were specifically and individually indicated to be incorporated herein by reference.

What is claimed is:

1. A crystalline form of (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester tosylate salt having a differential scanning calorimetric (DSC) onset temperature within 2% of 240° C.

2. The crystalline form of claim 1, wherein the DSC onset temperature is within 1% of 240° C.

3. The crystalline form of claim 1, wherein the DSC onset temperature is within 0.5% of 240° C.

4. The crystalline form of claim 1, wherein the crystalline form has an X-ray powder diffraction (XRPD) pattern comprising a peak at a two-theta angle of 6.3°±0.2°.

5. The crystalline form of claim 1, wherein the crystalline form has an X-ray powder diffraction (XRPD) pattern comprising a peak at a two-theta angle of 17.9°±0.2°.

6. The crystalline form of claim 1, wherein the crystalline form has an X-ray powder diffraction (XRPD) pattern comprising a peak at a two-theta angle of 19.7°±0.2°.

7. The crystalline form of claim 1, wherein the crystalline form is stable upon exposure to about 25° C. and about 60% relative humidity.

8. The crystalline form of claim 1, wherein the crystalline form has a D90 particle size of about 70 μM in length.

9. The crystalline form of claim 1, wherein the crystalline form has a D10 particle size of about 10 μM in length.

10. The crystalline form of claim 1, wherein the crystalline form has a purity of no less than 97% by weight of (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester tosylate salt.

11. The crystalline form of claim 1, wherein the crystalline form has a purity of no less than 98% by weight of (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester tosylate salt.

12. The crystalline form of claim 1, wherein the crystalline form has a purity of no less than 97% by weight of (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester tosylate salt; and has an X-ray powder diffraction (XRPD) pattern comprising peaks at two-theta angles of 6.3°±0.2°, 17.9°±0.2°, and 19.7°±0.2°.

13. The crystalline form of claim 1, wherein the (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester tosylate salt is:

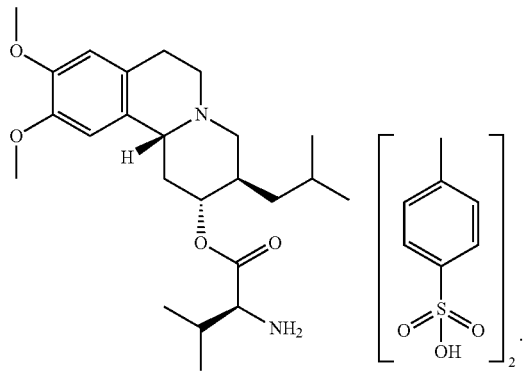

14. A pharmaceutical composition comprising the crystalline form of claim 1 and a pharmaceutically acceptable carrier.

15. The pharmaceutical composition of claim 14, wherein the composition is formulated for oral administration.

16. The pharmaceutical composition of claim 14, wherein the pharmaceutical composition is a unit dosage form.

17. The pharmaceutical composition of claim 14, wherein the pharmaceutical composition is in the form of a capsule.

18. A pharmaceutical composition comprising the crystalline form of claim 12 and a pharmaceutically acceptable carrier.

19. The pharmaceutical composition of claim 18, wherein the composition is formulated for oral administration.

20. The pharmaceutical composition of claim 18, wherein the pharmaceutical composition is a unit dosage form.

21. The pharmaceutical composition of claim 18, wherein the pharmaceutical composition is in the form of a capsule.

22. A pharmaceutical composition comprising the crystalline form of claim 13 and a pharmaceutically acceptable carrier.

23. The pharmaceutical composition of claim 22, wherein the composition is formulated for oral administration.

24. The pharmaceutical composition of claim 22, wherein the pharmaceutical composition is a unit dosage form.

25. The pharmaceutical composition of claim 22, wherein the pharmaceutical composition is in the form of a capsule.

26. A method of treating a hyperkinetic movement disorder comprising administering the crystalline form of claim 1, wherein the treating is ameliorating one or more symptoms of the hyperkinetic movement disorder.

27. The method of claim 26, wherein the hyperkinetic movement disorder is tardive dyskinesia.

* * * * *